United States Patent
Kobayashi et al.

(10) Patent No.: US 9,828,357 B2
(45) Date of Patent: *Nov. 28, 2017

(54) CYCLIC COMPOUNDS

(71) Applicant: Takeda Pharmaceutical Company Limited, Chuo-ku, Osaka-shi, Osaka (JP)

(72) Inventors: Toshitake Kobayashi, Kanagawa (JP); Morihisa Saitoh, Kanagawa (JP); Yasufumi Wada, Kanagawa (JP); Hiroshi Nara, Kanagawa (JP); Nobuyuki Negoro, Kanagawa (JP); Taisuke Katoh, Kanagawa (JP); Masashi Yamasaki, Kanagawa (JP); Takahiro Tanaka, Kanagawa (JP); Naomi Kitamoto, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/356,906

(22) Filed: Nov. 21, 2016

(65) Prior Publication Data

US 2017/0066737 A1    Mar. 9, 2017

Related U.S. Application Data

(63) Continuation of application No. 15/175,292, filed on Jun. 7, 2016, now Pat. No. 9,533,966, which is a continuation of application No. 15/148,210, filed on May 6, 2016.

(30) Foreign Application Priority Data

May 8, 2015    (JP) ................. 2015-095817

(51) Int. Cl.
| | |
|---|---|
| *C07D 317/72* | (2006.01) |
| *C07C 317/12* | (2006.01) |
| *C07D 309/28* | (2006.01) |
| *C07C 317/44* | (2006.01) |
| *C07C 317/46* | (2006.01) |

(52) U.S. Cl.
CPC .......... *C07D 317/72* (2013.01); *C07C 317/12* (2013.01); *C07C 317/44* (2013.01); *C07C 317/46* (2013.01); *C07D 309/28* (2013.01); *C07C 2601/16* (2017.05); *C07C 2602/08* (2017.05)

(58) Field of Classification Search
USPC ........................ 514/278, 409, 462
See application file for complete search history.

(56) References Cited

U.S. PATENT DOCUMENTS

| | | | |
|---|---|---|---|
| 6,495,604 B1 | 12/2002 | Ichimori et al. | |
| 7,078,540 B1 | 7/2006 | Tamura et al. | |
| RE43,858 E | 12/2012 | Kimura et al. | |
| 9,533,966 B2 * | 1/2017 | Kobayashi | C07D 317/72 |
| 2005/0176783 A1 | 8/2005 | Tamura et al. | |
| 2006/0058288 A1 | 3/2006 | Ii et al. | |
| 2009/0233952 A1 | 9/2009 | Kimura et al. | |
| 2011/0184034 A1 | 7/2011 | Ii et al. | |

FOREIGN PATENT DOCUMENTS

| | | |
|---|---|---|
| JP | 2008-260760 A | 10/2008 |
| WO | WO 99/46242 A1 | 9/1999 |
| WO | WO 01/10826 A1 | 2/2001 |
| WO | WO 2007/032362 A1 | 3/2007 |

OTHER PUBLICATIONS

Chong et al., "Toll-like receptor 4 mediates ischemia/reperfusion injury of the heart," The Journal of Thoracic and Cardiovascular Surgery, Aug. 2004, 128(2):170-179.

Dhillon et al., "A single nucleotide polymorphism of Toll-like receptor 4 identifies the risk of developing graft failure after liver transplantation," J. Hepatol., Jul. 2010, 53(1):67-72.

Ilmakunnas et al., "High Mobility Group Box 1 Protein as a Marker of Hepatocellular Injury in Human Liver Transplantation," Liver Transplantation, Oct. 2008, 14(10):1517-1525.

Li et al., "Toll-Like Receptor 4 Signaling Contributes to Paclitaxel-induced Peripheral Neuropathy," The Journal of Pain, Jul. 2014, 15(7):712-725.

* cited by examiner

*Primary Examiner* — Pancham Bakshi
(74) *Attorney, Agent, or Firm* — Foley & Lardner LLP

(57) ABSTRACT

The present invention provides compounds having a Toll-like receptor 4 (TLR4) signaling inhibitory action useful as preventive and therapeutic drugs of inflammatory disease and/or central nervous system disease or diseases such as chemotherapy-induced peripheral neuropathy (CIPN), chemotherapy-induced neuropathic pain (CINP), liver injury, ischemia-reperfusion injury (IRI) and the like. The present invention relates to a compound represented by formula (I) and a salt thereof:

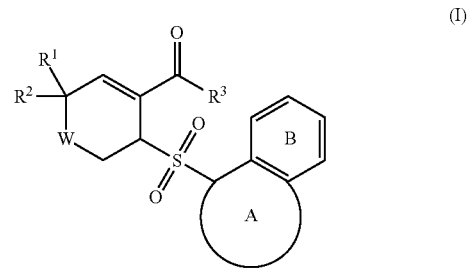

wherein, each symbol is explained in greater detail in the specification.

4 Claims, No Drawings

CYCLIC COMPOUNDS

CROSS-REFERENCE TO RELATED PATENT APPLICATIONS

This application is a Continuation of U.S. application Ser. No. 15/175,292, filed Jun. 7, 2016, which is a Continuation of U.S. application Ser. No. 15/148,210, filed May 6, 2016, which claims priority from Japanese Application No. 2015-095817, filed May 8, 2015, the contents of which are incorporated in full herein.

TECHNICAL FIELD

The present invention relates to novel cyclic compounds having a Toll-like receptor 4 (TLR4) signal inhibitory action useful as preventive and therapeutic drugs of autoimmune disease and/or inflammatory disease or diseases such as chemotherapy-induced peripheral neuropathy (CIPN), chemotherapy-induced neuropathic pain (CINP), liver injury, ischemia-reperfusion injury (IRI) and the like, and use thereof.

BACKGROUND OF THE INVENTION

TLR4 was initially discovered as a receptor which recognizes lipopolysaccharide of Gram negative bacteria and activates the natural immunity system. However, in recent years, it has been elucidated that not only does TLR4 activate such natural immunity reactions for preventing infections, but also recognizes various endogenous ligands produced in said various diseases and activates various cells playing central roles in the said diseases. Moreover, it has been reported that expression of TLR4 is accentuated in lesions of various diseases and that onset and progression of diseases in disease model animals are markedly suppressed in TLR4 knockout mouse and mutant mouse. Accordingly, it is suggested that TLR4 plays an important role in autoimmune disease and/or inflammatory disease, and diseases such as cardiac disease, renal disease, liver disease, central nervous system disease, infectious disease, malignant tumor, sepsis, septic shock and the like.

In addition to such diseases, the relationship to ischemia-reperfusion injury (ischemia reperfusion injury: IRI) caused by reperfusion of blood flow to organs and tissues in ischemic condition upon organ transplantation and the like, is also reported. High Mobility Group Box 1 (HMGB-1), which is one of TLR4 endogenous ligands, increases in transplanted organ. Moreover, the transplanted organ derived from donor with genetically impaired TLR4 function shows resistance to IRI-associated dysfunction. From such publicly known knowledge, it is suggested that TLR4 signal due to HMGB-1 plays an important role in IRI (Non-Patent Document 1, Non-Patent Document 2).

As a result, TLR4 signaling inhibitors (may also be called "TLR4 inhibitors") are anticipated to be preventive and therapeutic drugs of autoimmune disease and/or inflammatory disease or diseases such as cardiac disease, renal disease, liver disease, central nervous system disease, infectious disease, malignant tumor, sepsis, septic shock, etc.

In Patent Document 1 the following compound

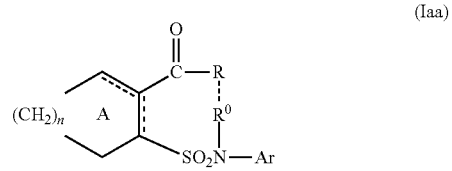

(Iaa)

(wherein, each symbol is described in the description in the said literature) is reported as a TLR4 signaling inhibitor.

In Patent Document 2 the following compound

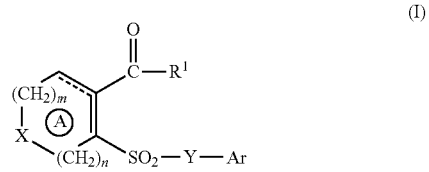

(I)

(wherein, each symbol is described in the description in the said literature) is reported as a TLR4 signaling inhibitor.

In Patent Documents 3 and 4 the following compound

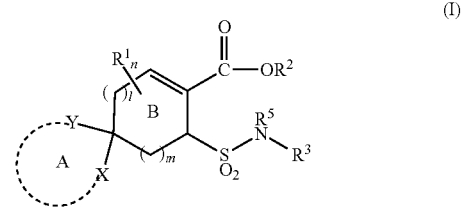

(I)

(wherein, each symbol is described in the description in the said literature) is reported as TLR4 signaling inhibitor.

DOCUMENT LIST

Patent Document

[Patent Document 1] WO 99/46242
[Patent Document 2] WO 2001/010826
[Patent Document 3] WO 2007/032362
[Patent Document 4] JP 2008-260760

Non-Patent Document

[Non-Patent Document 1] Liver Transpl. 2008 October, 14(10), 1517-25
[Non-Patent Document 2] J. Hepatol. 2010 July 53(1), 67-72

SUMMARY OF THE INVENTION

Problems to be Solved by the Invention

The object of the present invention is to provide a compound having excellent TLR4 signaling inhibitory action, which is useful as a drug in the treatment and prevention autoimmune disease and/or inflammatory disease, and diseases such as chemotherapy-induced peripheral neuropathy (CIPN), chemotherapy-induced neuropathic pain (CINP), liver injury, ischemia-reperfusion injury (IRI) and the like.

Means of Solving the Problems

These inventors made assiduous investigations in order to achieve a solution to said problem, and as a result, it was discovered that the compounds represented by the following formula (I) have excellent TLR4 signaling inhibitory action. The present invention was completed on the basis of this discovery.

In other words, the present invention is as follows.
(1) A compound represented by the following formula (I) or a salt thereof (hereinafter, abbreviated to compound (I):

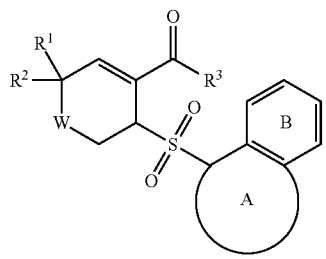

(wherein,
Ring A is an optionally substituted 5 or 6 membered ring;
Ring B is an optionally substituted benzene ring;
$R^1$ and $R^2$ are independently a hydrogen atom or a substituent, or $R^1$ and $R^2$ may bond together to form an optionally substituted ring;
W is $CH_2$, NH or O; and
$R^3$ is a substituent).
(2) The compound or salt according to the above-mentioned (1), wherein Ring A is cyclopentene or cyclohexene.
(3) The compound or salt according to the above-mentioned (1), wherein Ring B is a benzene ring optionally substituted by 1 to 3 substituent(s) selected from a halogen atom and a $C_{1-6}$ alkyl group.
(4) The compound or salt according to the above-mentioned (1), wherein as to $R^1$ and $R^2$, (1) $R^1$ and $R^2$ are both hydrogen atoms, or (2) one of $R^1$ and $R^2$ is a hydrogen atom, and the other is a hydroxy group, or $R^1$ and $R^2$ may bond together to form a 3- to 8-membered monocyclic non-aromatic heterocycle optionally substituted by 1 to 3 $C_{1-6}$ alkyl group(s) optionally substituted by 1 to 3 substituent(s) selected from a hydroxy group and a $C_{1-6}$ alkoxy group.
(5) The compound or salt according to the above-mentioned (1), wherein W is $CH_2$ or O.
(6) The compound or salt according to the above-mentioned (1), wherein $R^3$ is a $C_{1-6}$ alkoxy group optionally substituted by 1 to 3 $C_{3-10}$ cycloalkyl group(s) optionally substituted by 1 to 3 $C_{1-6}$ alkyl group(s).
(7) The compound or salt according to the above-mentioned (1), wherein
Ring A is cyclopentene or cyclohexene;
Ring B is a benzene ring optionally substituted by 1 to 3 substituent(s) selected from a halogen atom and a $C_{1-6}$ alkyl group;
as to $R^1$ and $R^2$, (1) $R^1$ and $R^2$ are both hydrogen atoms, or (2) one of $R^1$ and $R^2$ is a hydrogen atom, and the other is a hydroxy group, or $R^1$ and $R^2$ may bond together to form a 3- to 8-membered monocyclic non-aromatic heterocycle, which is optionally substituted by 1 to 3 $C_{1-6}$ alkyl group(s) optionally substituted by 1 to 3 substituent(s) selected from a hydroxy group and a $C_{1-6}$ alkoxy group;
W is $CH_2$ or O; and
$R^3$ is a $C_{1-6}$ alkoxy group optionally substituted by 1 to 3 $C_{3-10}$ cycloalkyl group(s) optionally substituted by 1 to 3 $C_{1-6}$ alkyl group(s).
(8) Ethyl (2R,3R,8R)-8-(((1S)-7-chloro-2,3-dihydro-1H-inden-1-yl)sulfonyl)-2,3-bis(hydroxymethyl)-1,4-dioxaspiro[4.5]dec-6-ene-7-carboxylate.
(9) Ethyl (2R,3R,8R)-8-(((1S)-7-chloro-5-fluoro-2,3-dihydro-1H-inden-1-yl)sulfonyl)-2,3-bis(hydroxymethyl)-1,4-dioxaspiro[4.5]dec-6-ene-7-carboxylate.
(10) Ethyl (2R,3R,8R)-8-(((1S)-7-chloro-2,3-dihydro-1H-inden-1-yl)sulfonyl)-2,3-bis(methoxymethyl)-1,4-dioxaspiro[4.5]dec-6-ene-7-carboxylate.
(11) A medicament comprising the compound or salt according to the above-mentioned (1).
(12) The medicament according to the above-mentioned (11), which is a toll-like receptor 4 inhibitor.
(13) The medicament according to the above-mentioned (11), which is an agent for the prophylaxis or treatment of autoimmune disease and/or inflammatory disease.
(14) The medicament according to the above-mentioned (11), which is an agent for the prophylaxis or treatment of chemotherapy-induced peripheral neuropathy (CIPN), chemotherapy-induced neuropathic pain (CINP), liver injury and/or ischemia-reperfusion injury (IRI).
(15) The compound or salt according to the above-mentioned (1) for use in the prophylaxis or treatment of autoimmune disease and/or inflammatory disease.
(16) The compound or salt according to the above-mentioned (1) for use in the prophylaxis or treatment of chemotherapy-induced peripheral neuropathy (CIPN), chemotherapy-induced neuropathic pain (CINP), liver injury and/or ischemia-reperfusion injury (IRI).
(17) A method of inhibiting toll-like receptor 4 in a mammal, which comprises administering an effective amount of the compound or salt according to the above-mentioned (1) to the mammal.
(18) A method for the prophylaxis or treatment of autoimmune disease and/or inflammatory disease in a mammal, which comprises administering an effective amount of the compound or salt according to the above-mentioned (1) to the mammal.
(19) A method for the prophylaxis or treatment of chemotherapy-induced peripheral neuropathy (CIPN), chemotherapy-induced neuropathic pain (CINP), liver injury and/or ischemia-reperfusion injury (IRI) in a mammal, which comprises administering an effective amount of the compound or salt according to the above-mentioned (1) to the mammal.
(20) Use of the compound or salt according to the above-mentioned (1) for the production of an agent for the prophylaxis or treatment of autoimmune disease and/or inflammatory disease.
(21) Use of the compound or salt according to the above-mentioned (1) for the production of an agent for the prophylaxis or treatment of chemotherapy-induced peripheral neuropathy (CIPN), chemotherapy-induced neuropathic pain (CINP), liver injury and/or ischemia-reperfusion injury (IRI).

Effect of the Invention

The compound of the present invention has TLR4 signaling inhibitory action and is useful as a preventive and therapeutic drug of autoimmune disease and/or inflammatory disease or disease such as chemotherapy-induced peripheral neuropathy (CIPN), chemotherapy-induced neuropathic pain (CINP), liver injury, ischemia-reperfusion injury (IRI), etc.

DETAILED DESCRIPTION OF THE INVENTION

The present invention will now be described in detail.

The definition of each substituent used in this specification will now be described in detail. Each substituent has the following definitions unless otherwise specifically stated to the contrary.

In this specification, for example, as "halogen atom", fluorine, chlorine, bromine, iodine and the like may be proposed.

In this specification, for example, as "$C_{1-6}$ alkyl group", methyl, ethyl, propyl, isopropyl, butyl, isobutyl, sec-butyl, tert-butyl, pentyl, isopentyl, neopentyl, 1-ethyl propyl, hexyl, isohexyl, 1,1-dimethylbutyl, 2,2-dimethylbutyl, 3,3-dimethylbutyl, 2-ethyl butyl and the like may be proposed.

In this specification, for example, as "optionally halogenated $C_{1-6}$ alkyl group", $C_{1-6}$ alkyl group which may have 1 to 7, preferably 1 to 5 halogen atoms and the like may be proposed. Specific examples comprise methyl, chloromethyl, difluoromethyl, trichloromethyl, trifluoromethyl, ethyl, 2-bromoethyl, 2, 2, 2-trifluoroethyl, tetrafluoroethyl, pentafluoroethyl, propyl, 2,2-difluoropropyl, 3, 3, 3-trifluoropropyl, isopropyl, butyl, 4, 4, 4-trifluorobutyl, isobutyl, sec-butyl, tert-butyl, pentyl, isopentyl, neopentyl, 5, 5, 5-trifluoropentyl, hexyl, and 6, 6, 6-trifluoro hexyl.

In this specification, for example, as "$C_{2-6}$ alkenyl group", ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like may be proposed.

In this specification, for example, as "$C_{2-6}$ alkynyl group", ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 4-methyl-2-pentynyl and the like may be proposed.

In this specification, for example, as "$C_{3-10}$ cycloalkyl group", cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, adamantyl and the like may be proposed.

In this specification, for example, as "optionally halogenated $C_{3-10}$ cycloalkyl group", $C_{3-10}$ cycloalkyl group which may have 1 to 7, preferably 1 to 5 halogen atoms and the like may be proposed. Specific examples comprise cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In this specification, for example, as "$C_{3-10}$ cycloalkenyl group", cyclopropenyl, cyclobutenyl, cyclopentenyl, cyclohexenyl, cycloheptenyl, cyclooctenyl and the like may be proposed.

In this specification, for example, as "$C_{6-14}$ aryl group", phenyl, 1-naphthyl, 2-naphthyl, 1-anthryl, 2-anthryl, 9-anthryl and the like may be proposed.

In this specification, for example, as "$C_{7-16}$ aralkyl group", benzyl, phenethyl, naphthylmethyl, phenylpropyl and the like may be proposed.

In this specification, for example, as "$C_{1-6}$ alkoxy group", methoxy, ethoxy, propoxy, isopropoxy, butoxy, isobutoxy, sec-butoxy, tert-butoxy, pentyloxy, hexyloxy and the like may be proposed.

In this specification, for example, as "optionally halogenated $C_{1-6}$ alkoxy group", $C_{1-6}$ alkoxy group which may have 1 to 7, preferably 1 to 5 halogen atoms and the like may be proposed. Specific examples comprise methoxy, difluoromethoxy, trifluoromethoxy, ethoxy, 2, 2, 2-trifluoroethoxy, propoxy, isopropoxy, butoxy, 4,4,4-trifluorobutoxy, isobutoxy, sec-butoxy, pentyloxy and hexyloxy.

In this specification, for example, as "$C_{3-10}$ cycloalkyloxy group", cyclopropyloxy, cyclobutyloxy, cyclopentyloxy, cyclohexyloxy, cycloheptyloxy, cyclooctyloxy and the like may be proposed.

In this specification, for example, as "$C_{1-6}$ alkylthio group", methylthio, ethylthio, propylthio, isopropylthio, butylthio, sec-butylthio, tert-butylthio, pentylthio, hexylthio and the like may be proposed.

In this specification, for example, as "optionally halogenated $C_{1-6}$ alkylthio group", $C_{1-6}$ alkylthio group which may have 1 to 7, preferably 1 to 5 halogen atoms and the like may be proposed. Specific examples comprise methylthio, difluoromethylthio, trifluoromethylthio, ethylthio, propylthio, isopropylthio, butylthio, 4,4,4-trifluorobutylthio, pentylthio and hexylthio.

In this specification, for example, as "$C_{1-6}$ alkyl-carbonyl group", acetyl, propanoyl, butanoyl, 2-methylpropanoyl, pentanoyl, 3-methylbutanoyl, 2-methylbutanoyl, 2,2-dimethylpropanoyl, hexanoyl, heptanoyl and the like may be proposed.

In this specification, for example, as "optionally halogenated $C_{1-6}$ alkyl-carbonyl group", $C_{1-6}$ alkyl-carbonyl group which may have 1 to 7, preferably 1 to 5 halogen atoms and the like may be proposed. Specific examples comprise acetyl, chloroacetyl, trifluoroacetyl, trichloroacetyl, propanoyl, butanoyl, pentanoyl and hexanoyl.

In this specification, for example, as "$C_{1-6}$ alkoxy-carbonyl group", methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like may be proposed.

In this specification, for example, as "$C_{6-14}$ aryl-carbonyl group", benzoyl, 1-naphthoyl, 2-naphthoyl and the like may be proposed.

In this specification, for example, as "$C_{7-16}$ aralkyl-carbonyl group", phenylacetyl, phenyl propionyl and the like may be proposed.

In this specification, for example, as "5 to 14 membered aromatic heterocyclyl-carbonyl group", nicotinoyl, isonicotinoyl, thenoyl, furoyl may be proposed.

In this specification, for example, as "3 to 14 membered non-aromatic heterocyclyl-carbonyl group", morpholinyl carbonyl, piperidinylcarbonyl, pyrrolidinylcarbonyl may be proposed.

In this specification, for example, as "mono- or di-$C_{1-6}$ alkyl-carbamoyl group", methylcarbamoyl, ethylcarbamoyl, dimethylcarbamoyl, diethylcarbamoyl, N-ethyl-N-methyl-carbamoyl may be proposed.

In this specification, for example, as "mono- or di-$C_{7-16}$ aralkyl-carbamoyl group", benzylcarbamoyl, phenethylcarbamoyl may be proposed.

In this specification, for example, as "$C_{1-6}$ alkylsulfonyl group", methylsulfonyl, ethylsulfonyl, propylsulfonyl, isopropylsulfonyl, butylsulfonyl, sec-butylsulfonyl, tert-butylsulfonyl and the like may be proposed.

In this specification, for example, as "optionally halogenated $C_{1-6}$ alkylsulfonyl group", $C_{1-6}$ alkylsulfonyl group which may have 1 to 7, preferably 1 to 5 halogen atoms and the like may be proposed. Specific examples comprise methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In this specification, for example, as "$C_{6-14}$ arylsulfonyl group", phenylsulfonyl, 1-naphthylsulfonyl, 2-naphthylsulfonyl and the like may be proposed.

In this specification, for example, as "substituent", halogen atom, cyano group, nitro group, optionally substituted hydrocarbon group, optionally substituted heterocyclic group, acyl group, optionally substituted amino group, optionally substituted carbamoyl group, optionally substituted thiocarbamoyl group, optionally substituted sulfamoyl group, optionally substituted hydroxy group, optionally substituted sulfanyl (SH) group, optionally substituted silyl group and the like may be proposed.

In this specification, for example as "hydrocarbon group" (including "hydrocarbon group" in "in optionally substituted hydrocarbon group"), $C_{1-6}$ alkyl group, $C_{2-6}$ alkenyl group, $C_{2-6}$ alkynyl group, $C_{3-10}$ cycloalkyl group, $C_{3-10}$ cycloalkenyl group, $C_{6-14}$ aryl group and $C_{7-16}$ aralkyl group may be proposed.

In this specification, for example, as "optionally substituted hydrocarbon group", optionally substituted hydrocarbon group selected from the following substituent group A may be proposed.

Substituent Group A
(1) Halogen atom,
(2) Nitro group,
(3) Cyano group,
(4) Oxo group,
(5) Hydroxy group,
(6) Optionally halogenated $C_{1-6}$ alkoxy group,
(7) $C_{6-14}$ aryloxy group (for example, phenoxy, naphthoxy),
(8) $C_{7-16}$ aralkyloxy group (for example, benzyloxy),
(9) 5 to 14 membered aromatic heterocyclyl-oxy group (for example, pyridyloxy),
(10) 3 to 14 membered non-aromatic heterocyclyl-oxy group (for example, morpholinyloxy, piperidinyloxy),
(11) $C_{1-6}$ alkyl-carbonyloxy group (for example, acetoxy, propanoyloxy),
(12) $C_{6-14}$ aryl-carbonyloxy group (for example benzoyloxy, 1-naphthoyloxy, 2-naphthoyloxy),
(13) $C_{1-6}$ alkoxy-carbonyloxy group (for example, methoxycarbonyloxy, ethoxycarbonyloxy, propoxy carbonyloxy, butoxycarbonyloxy),
(14) Mono- or di-$C_{1-6}$ alkyl-carbamoyloxy group (for example, methylcarbamoyloxy, ethylcarbamoyloxy, dimethylcarbamoyloxy, diethylcarbamoyloxy),
(15) $C_{6-14}$ aryl-carbamoyloxy group (for example, phenylcarbamoyloxy, naphthylcarbamoyloxy),
(16) 5 to 14 membered aromatic heterocyclyl-carbonyloxy group (for example, nicotinoyloxy),
(17) 3 to 14 membered non-aromatic heterocyclyl-carbonyloxy group (for example, morpholinylcarbonyloxy, piperidinylcarbonyloxy),
(18) Optionally halogenated $C_{1-6}$ alkylsulfonyloxy group (for example, methylsulfonyloxy, trifluoromethylsulfonyloxy),
(19) $C_{6-14}$ arylsulfonyloxy group (for example, phenylsulfonyloxy, toluenesulfonyloxy) optionally substituted by $C_{1-6}$ alkyl group,
(20) Optionally halogenated $C_{1-6}$ alkylthio group,
(21) 5 to 14 membered aromatic heterocyclic group,
(22) 3 to 14 membered non-aromatic heterocyclic group,
(23) Formyl group,
(24) Carboxy group,
(25) Optionally halogenated $C_{1-6}$ alkyl-carbonyl group,
(26) $C_{6-14}$ aryl-carbonyl group,
(27) 5 to 14 membered aromatic heterocyclyl-carbonyl group,
(28) 3 to 14 membered non-aromatic heterocyclyl-carbonyl group,
(29) $C_{1-6}$ alkoxy-carbonyl group,
(30) $C_{6-14}$ aryloxy-carbonyl group (for example phenyloxycarbonyl, 1-naphthyloxycarbonyl, 2-naphthyloxycarbonyl),
(31) $C_{7-16}$ aralkyloxy-carbonyl group (for example benzyloxycarbonyl, phenethyloxycarbonyl),
(32) Carbamoyl group,
(33) Thiocarbamoyl group,
(34) Mono- or di-$C_{1-6}$ alkyl-carbamoyl group,
(35) $C_{6-14}$ aryl-carbamoyl group (for example, phenylcarbamoyl),
(36) 5 to 14 membered aromatic heterocyclyl-carbamoyl group (for example, pyridylcarbamoyl, thienylcarbamoyl),
(37) 3 to 14 membered non-aromatic heterocyclyl-carbamoyl group (for example, morpholinylcarbamoyl, piperidinylcarbamoyl),
(38) Optionally halogenated $C_{1-6}$ alkylsulfonyl group,
(39) $C_{6-14}$ arylsulfonyl group,
(40) 5 to 14 membered aromatic heterocyclylsulfonyl group (for example, pyridyl sulfonyl, thienyl sulfonyl),
(41) Optionally halogenated $C_{1-6}$ alkylsulfinyl group,
(42) $C_{6-14}$ arylsulfinyl group (for example phenylsulfinyl, 1-naphthyl sulfinyl, 2-naphthyl sulfinyl),
(43) 5 to 14 membered aromatic heterocyclyl-sulfinyl group (for example, pyridyl sulfinyl, thienyl sulfinyl),
(44) Amino group,
(45) Mono- or di-$C_{1-6}$ alkylamino group (for example methylamino, ethylamino, propylamino, isopropylamino, butylamino, dimethylamino, diethylamino, dipropylamino, dibutylamino, N-ethyl-N-methylamino),
(46) Mono- or di-$C_{6-14}$ arylamino group (for example, phenylamino),
(47) 5 to 14 membered aromatic heterocyclyl-amino group (for example, pyridylamino),
(48) $C_{7-16}$ aralkylamino group (for example, benzylamino),
(49) Formylamino group,
(50) $C_{1-6}$ alkyl-carbonylamino group (for example, acetylamino, propanoylamino, butanoylamino),
(51) ($C_{1-6}$ alkyl) ($C_{1-6}$ alkyl-carbonyl) amino group (for example N-acetyl-N-methylamino),
(52) $C_{6-14}$ aryl-carbonylamino group (for example, phenyl carbonylamino, naphthyl carbonylamino),
(53) $C_{1-6}$ alkoxy-carbonylamino group (for example methoxycarbonylamino, ethoxycarbonylamino, propoxycarbonylamino, butoxycarbonylamino, tert-butoxycarbonylamino),
(54) $C_{7-16}$ aralkyloxy-carbonylamino group (for example benzyloxycarbonylamino),
(55) $C_{1-6}$ alkylsulfonylamino group (for example, methylsulfonylamino, ethylsulfonylamino),
(56) $C_{6-14}$ arylsulfonylamino group (for example, phenylsulfonylamino, toluenesulfonylamino) optionally substituted by $C_{1-6}$ alkyl group,
(57) Optionally halogenated $C_{1-6}$ alkyl group,
(58) $C_{2-6}$ alkenyl group,
(59) $C_{2-6}$ alkynyl group,
(60) $C_{3-10}$ cycloalkyl group,

(61) $C_{3-10}$ cycloalkenyl group, and,

(62) $C_{6-14}$ aryl group.

For example, in "optionally substituted hydrocarbon group", said number of substituents is 1 to 5, preferably 1 to 3. When the number of substituents is 2 or more, each substituent may be the same or different.

In this specification, as "heterocyclic group" (including "heterocyclic group" in "optionally substituted heterocyclic group"), for example (i) aromatic heterocyclic group, (ii) non-aromatic heterocyclic group and (iii) 7-10 membered bridged heterocyclic group, each containing respectively 1 to 4 heteroatoms selected from oxygen, sulfur and nitrogen atoms in addition to the carbon atom content as ring atoms, may be proposed.

In this specification, as "aromatic heterocyclic group" (including "5-14 membered aromatic heterocyclic group", 5 to 14 membered (preferably 5 to 10 membered) aromatic heterocyclic group containing 1 to 4 heteroatoms selected from nitrogen atom, sulfur atom and oxygen atom in addition to the carbon atom content as ring atoms, may be proposed.

As ideal examples of said "aromatic heterocyclic group", 5 to 6 membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl etc.;

8 to 14 membered condensed polycyclic (preferably bicyclic or tricyclic) aromatic heterocyclic group such as benzothiophenyl, benzofuranyl, benzimidazolyl, benzoxazolyl, benzoisoxazolyl, benzothiazolyl, benzoisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathienyl, indolyl, isoindolyl, 1H-indazolyl, purinyl, isoquinolyl, quinolyl, phthalidinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl, etc. may be proposed.

In this specification, for example, as "non-aromatic heterocyclic group" (including "3 to 14 membered non-aromatic heterocyclic group"), 3 to 14 membered (preferably 4 to 10 membered) non-aromatic heterocyclic group, containing 1 to 4 heteroatoms selected from nitrogen atom, sulfur atom and oxygen atom in addition to the carbon atom content as ring atoms, may be proposed.

As ideal example of said "non-aromatic heterocyclic group", 3 to 8 membered monocyclic non-aromatic heterocyclic group such as aziridinyl, oxiranyl, thiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl, etc.;

9 to 14 membered condensed polycyclic (preferably bicyclic or tricyclic) non-aromatic heterocyclic group such as dihydrobenzofuranyl, dihydrobenzoimidazolyl, dihydrobenzooxazolyl, dihydrobenzothiazolyl, dihydrobenzoisothiazolyl, dihydronaphtho[2,3-b]thienyl, tetrahydroisoquinolyl, tetrahydroquinolyl, 4H-quinolidinyl, indolinyl, isoindolinyl, tetrahydrothieno[2,3-c]pyridinyl, tetrahydrobenzoazepinyl, tetrahydroquinoxalinyl, tetrahydrophenanthridinyl, hexahydrophenothiazinyl, hexahydrophenoxazinyl, tetrahydrophthalidinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanethenyl, octahydroisoquinolyl, etc. may be proposed.

In this specification, as ideal example of "7 to 10 membered bridged heterocyclic group", quinuclidinyl and 7-azabicyclo[2.2.1]heptanyl may be proposed.

In this specification, as "nitrogen-containing heterocyclic group", those groups among "heterocyclic groups" that contain at least one nitrogen atom as ring atom content may be proposed.

In this specification, for example, as "optionally substituted heterocyclic group", heterocyclic groups optionally substituted by substituent(s) selected from said substituent group A may be proposed.

The number of substituents in "optionally substituted heterocyclic group" is for example 1 to 3. When the number of substituents is 2 or more, each substituent may be the same or different.

In this specification, as "acyl group", for example, formyl group, carboxy group, carbamoyl group, thiocarbamoyl group, sulfino group, sulfo group, sulfamoyl group and phosphono group, each respectively optionally substituted by "1 or 2 substituents selected from $C_{1-6}$ alkyl group, $C_{2-6}$ alkenyl group, $C_{3-10}$ cycloalkyl group, $C_{3-10}$ cycloalkenyl group, $C_{6-14}$ aryl group, $C_{7-16}$ aralkyl group, 5 to 14 membered aromatic heterocyclic group and 3 to 14 membered non-aromatic heterocyclic group, which may each further have 1 to 3 substituent(s) selected from halogen atoms, optionally halogenated $C_{1-6}$ alkoxy group, hydroxy group, nitro group, cyano group, amino group and carbamoyl group", may be proposed.

Moreover, as "acyl group", hydrocarbon-sulfonyl group, heterocyclyl-sulfonyl group, hydrocarbon-sulfinyl group, heterocyclyl-sulfinyl group may also be proposed.

Wherein, as hydrocarbon-sulfonyl group, a sulfonyl group bonded with a hydrocarbon group; as heterocyclyl-sulfonyl group, a sulfonyl group bonded with a heterocyclic group; as hydrocarbon-sulfinyl group, a sulfinyl group bonded with a hydrocarbon group; as heterocyclyl-sulfinyl group, a sulfinyl group bonded with a heterocyclic group are respectively denoted.

Ideal examples of "acyl group" include formyl group, carboxy group, $C_{1-6}$ alkyl-carbonyl group, $C_{2-6}$ alkenyl-carbonyl group (for example, crotonoyl), $C_{3-10}$ cycloalkyl-carbonyl group (for example cyclobutanecarbonyl, cyclopentanecarbonyl, cyclohexanecarbonyl, cycloheptanecarbonyl), $C_{3-10}$ cycloalkenyl-carbonyl group (for example 2-cyclohexenecarbonyl), $C_{6-14}$ aryl-carbonyl group, $C_{7-16}$ aralkyl-carbonyl group, 5 to 14 membered aromatic heterocyclyl-carbonyl group, 3 to 14 membered non-aromatic heterocyclyl-carbonyl group, $C_{1-6}$ alkoxy-carbonyl group, $C_{6-14}$ aryloxy-carbonyl group (for example, phenyloxycarbonyl, naphthyloxycarbonyl), $C_{7-16}$ aralkyloxy-carbonyl group (for example, benzyloxycarbonyl, phenethyloxycarbonyl), carbamoyl group, mono- or di-$C_{1-6}$ alkyl-carbamoyl group, mono- or di-$C_{2-6}$ alkenyl-carbamoyl group (for example, diallylcarbamoyl), mono- or di-$C_{3-10}$ cycloalkyl-carbamoyl group (for example, cyclopropylcarbamoyl), mono- or di-$C_{6-14}$ aryl-carbamoyl group (for example, phenylcarbamoyl), mono- or di-$C_{7-16}$ aralkyl-carbamoyl group, 5 to 14 membered aromatic heterocyclyl-carbamoyl group (for example, pyridylcarbamoyl), thiocarbamoyl group, mono- or di-$C_{1-6}$ alkyl-thiocarbamoyl group (for example methylthiocarbamoyl, N-ethyl-N-methylthiocarbamoyl), mono- or di-$C_{2-6}$ alkenyl-thiocarbamoyl group (for example, diallylthiocarbamoyl), mono- or di-$C_{3-10}$ cycloalkyl-thiocarbamoyl group (for example, cyclopropylthiocarbamoyl, cyclohexylthiocarbamoyl), mono- or di-$C_{6-14}$ aryl-thiocarbamoyl group (for example, phenylthiocarbamoyl), mono- or di-$C_{7-16}$ aralkyl-thiocarbamoyl group (for example, benzylthiocarbamoyl, phenethylthiocarbamoyl), 5 to 14 membered aromatic heterocyclyl-thiocarbamoyl group (for example, pyridylthiocarbamoyl), sulfino group, $C_{1-6}$ alkylsulfinyl group (for example, methylsulfinyl, ethyl sulfinyl), sulfo group, $C_{1-6}$ alkylsulfonyl group, $C_{6-14}$ aryl sulfonyl group, phosphono group, mono- or di-$C_{1-6}$ alkyl phosphono group (for example, dimethylphosphone, diethylphosphone, diisopropylphosphone and dibutylphosphono) may be proposed.

In this specification, for example, as "optionally substituted amino group", an amino group which may have "1 or 2 substituents selected from $C_{1-6}$ alkyl group, $C_{2-6}$ alkenyl group, $C_{3-10}$ cycloalkyl group, $C_{6-14}$ aryl group, $C_{7-16}$ aralkyl group, $C_{1-6}$ alkyl-carbonyl group, $C_{6-14}$ aryl-carbonyl group, $C_{7-16}$ aralkyl-carbonyl group, 5 to 14 membered aromatic heterocyclyl-carbonyl group, 3 to 14 membered non-aromatic heterocyclyl-carbonyl group, $C_{1-6}$ alkoxy-carbonyl group, 5 to 14 membered aromatic heterocyclic groups, carbamoyl group, mono- or di-$C_{1-6}$ alkyl-carbamoyl group, mono- or di-$C_{7-16}$ aralkyl-carbamoyl group, $C_{1-6}$ alkylsulfonyl group and $C_{6-14}$ aryl sulfonyl group, which substituents may each respectively be substituted by 1-3 substituents selected from substituent group A" may be proposed.

As ideal examples of an optionally substituted amino group, an amino group, mono- or di-(optionally halogenated $C_{1-6}$ alkyl) amino group (for example, methylamino, trifluoromethylamino, dimethylamino, ethylamino, diethylamino, propylamino, dibutylamino), mono- or di-$C_{2-6}$ alkenylamino group (for example, diallylamino), mono- or di-$C_{3-10}$ cycloalkylamino group (for example, cyclopropylamino, cyclohexylamino), mono- or di-$C_{6-14}$ arylamino group (for example, phenylamino), mono- or di-$C_{7-16}$ aralkylamino group (for example, benzylamino, dibenzylamino), mono- or di-(optionally halogenated $C_{1-6}$ alkyl)-carbonylamino group (for example, acetylamino, propionylamino), mono- or di-$C_{6-14}$ aryl-carbonylamino group (for example, benzoylamino), mono- or di-$C_{7-16}$ aralkyl-carbonylamino group (for example, benzylcarbonylamino), mono- or di-5 to 14 membered aromatic heterocyclyl-carbonylamino group (for example, nicotinoylamino, isonicotinoylamino), mono- or di-3 to 14 membered non-aromatic heterocyclyl-carbonylamino group (for example, piperidinyl carbonylamino), mono- or di-$C_{1-6}$ alkoxy-carbonylamino group (for example tert-butoxycarbonylamino), 5 to 14 membered aromatic heterocyclyl-amino group (for example, pyridylamino), carbamoylamino group, (mono- or di-$C_{1-6}$ alkyl-carbamoyl) amino group (for example, methylcarbamoylamino), (mono- or di-$C_{7-16}$ aralkyl-carbamoyl)amino group (for example, benzylcarbamoylamino), $C_{1-6}$ alkylsulfonylamino group (for example, methylsulfonylamino, ethylsulfonylamino), $C_{6-14}$ arylsulfonylamino group (for example, phenylsulfonylamino), ($C_{1-6}$ alkyl) ($C_{1-6}$ alkyl-carbonyl) amino group (for example N-acetyl-N-methylamino), ($C_{1-6}$ alkyl) ($C_{6-14}$ aryl-carbonyl) amino group (for example N-benzoyl-N-methylamino) may be proposed.

In this specification, as "optionally substituted carbamoyl group", for example, a carbamoyl group optionally substituted by "1 or 2 substituent(s) selected from $C_{1-6}$ alkyl group, $C_{2-6}$ alkenyl group, $C_{3-10}$ cycloalkyl group, $C_{6-14}$ aryl group, $C_{7-16}$ aralkyl group, $C_{1-6}$ alkyl-carbonyl group, $C_{6-14}$ aryl-carbonyl group, $C_{7-16}$ aralkyl-carbonyl group, 5 to 14 membered aromatic heterocyclyl-carbonyl group, 3 to 14 membered non-aromatic heterocyclyl-carbonyl group, $C_{1-6}$ alkoxy-carbonyl group, 5 to 14 membered aromatic heterocyclic group, carbamoyl group, mono- or di-$C_{1-6}$ alkyl-carbamoyl group and mono- or di-$C_{7-16}$ aralkyl-carbamoyl group, each of which substituents may be optionally substituted by 1 to 3 substituent(s) selected from substituent group A" may be proposed.

As ideal examples of optionally substituted carbamoyl group, carbamoyl group, mono- or di-$C_{1-6}$ alkyl-carbamoyl group, mono- or di-$C_{2-6}$ alkenyl-carbamoyl group (for example, diallylcarbamoyl), mono- or di-$C_{3-10}$ cycloalkyl-carbamoyl group (for example, cyclopropylcarbamoyl, cyclohexylcarbamoyl), mono- or di-$C_{6-14}$ aryl-carbamoyl group (for example, phenylcarbamoyl), mono- or di-$C_{7-16}$ aralkyl-carbamoyl group, mono- or di-$C_{1-6}$ alkyl-carbonyl-carbamoyl group (for example, acetylcarbamoyl, propionylcarbamoyl), mono- or di-$C_{6-14}$ aryl-carbonyl-carbamoyl group (for example, benzoylcarbamoyl), and 5 to 14 membered aromatic heterocyclyl-carbamoyl group (for example, pyridylcarbamoyl) may be proposed.

In this specification, as "optionally substituted thiocarbamoyl group", for example, a thiocarbamoyl group which may have "1 or 2 substituent(s) selected from $C_{1-6}$ alkyl group, $C_{2-6}$ alkenyl group, $C_{3-10}$ cycloalkyl group, $C_{6-14}$ aryl group, $C_{7-16}$ aralkyl group, $C_{1-6}$ alkyl-carbonyl group, $C_{6-14}$ aryl-carbonyl group, $C_{7-16}$ aralkyl-carbonyl group, 5 to 14 membered aromatic heterocyclyl-carbonyl group, 3 to 14 membered non-aromatic heterocyclyl-carbonyl groups, $C_{1-6}$ alkoxy-carbonyl group, 5 to 14 membered aromatic heterocyclic group, carbamoyl group, mono- or di-$C_{1-6}$ alkyl-carbamoyl group and mono- or di-$C_{7-16}$ aralkyl-carbamoyl group", wherein each of such substituents may respectively have 1 to 3 substituent(s) selected from substituent group A" and may be proposed.

Ideal examples of optionally substituted thiocarbamoyl group comprise a thiocarbamoyl group, mono- or di-$C_{1-6}$ alkyl-thiocarbamoyl group (for example, methylthiocarbamoyl, ethylthiocarbamoyl, dimethylthiocarbamoyl, diethylthiocarbamoyl, N-ethyl-N-methylthiocarbamoyl), mono- or di-$C_{2-6}$ alkenyl-thiocarbamoyl group (for example, diallylthiocarbamoyl), mono- or di-$C_{3-10}$ cycloalkyl-thiocarbamoyl group (for example, cyclopropylthiocarbamoyl, cyclohexylthiocarbamoyl), mono- or di-$C_{6-14}$ aryl-thiocarbamoyl group (for example, phenylthiocarbamoyl), mono- or di-$C_{7-16}$ aralkyl-thiocarbamoyl group (for example, benzylthiocarbamoyl, phenethylthiocarbamoyl), mono- or di-$C_{1-6}$ alkyl-carbonyl-thiocarbamoyl group (for example, acetylthiocarbamoyl, propionylthiocarbamoyl), mono- or di-$C_{6-14}$ aryl-carbonyl-thiocarbamoyl group (for example, benzoylthiocarbamoyl), and 5 to 14 membered aromatic heterocyclyl-thiocarbamoyl group (for example, pyridylthiocarbamoyl).

In this specification, as "optionally substituted sulfamoyl group", a sulfamoyl group which may have 1 or 2 substituent(s) selected from $C_{1-6}$ alkyl group, $C_{2-6}$ alkenyl group, $C_{3-10}$ cycloalkyl group, $C_{6-14}$ aryl group, $C_{7-16}$ aralkyl group, $C_{1-6}$ alkyl-carbonyl group, $C_{6-14}$ aryl-carbonyl group, $C_{7-16}$ aralkyl-carbonyl group, 5 to 14 membered aromatic heterocyclyl-carbonyl group, 3 to 14 membered non-aromatic heterocyclyl-carbonyl group, $C_{1-6}$ alkoxy-carbonyl group, 5 to 14 membered aromatic heterocyclic group, carbamoyl group, mono- or di-$C_{1-6}$ alkyl-carbamoyl group and monoor di-$C_{7-16}$ aralkyl-carbamoyl group, wherein each of such substituents may respectively have 1 to 3 substituent(s) selected from substituent group A" may be proposed.

Ideal examples of optionally substituted sulfamoyl group comprise a sulfamoyl group, mono- or di-$C_{1-6}$ alkyl-sulfamoyl group (for example, methylsulfamoyl, ethylsulfamoyl, dimethylsulfamoyl, diethylsulfamoyl, N-ethyl-N-methylsulfamoyl), mono- or di-$C_{2-6}$ alkenyl-sulfamoyl group (for example, diallylsulfamoyl), mono- or di-$C_{3-10}$ cycloalkyl-sulfamoyl group (for example, cyclopropylsulfamoyl, cyclohexylsulfamoyl), mono- or di-$C_{6-14}$ aryl-sulfamoyl group (for example, phenylsulfamoyl), mono- or di-$C_{7-16}$ aralkyl-sulfamoyl group (for example, benzylsulfamoyl, phenethylsulfamoyl), mono- or di-$C_{1-6}$ alkyl-carbonyl-sulfamoyl group (for example, acetylsulfamoyl, propionylsulfamoyl), mono- or di-$C_{6-14}$ aryl-carbonyl-sulfamoyl group (for example, benzoylsulfamoyl) and 5 to 14 membered aromatic heterocyclyl-sulfamoyl group (for example, pyridylsulfamoyl).

In this specification, as "optionally substituted hydroxy group", an hydroxy group which may have "a substituent selected from $C_{1-6}$ alkyl group, $C_{2-6}$ alkenyl group, $C_{3-10}$ cycloalkyl group, $C_{6-14}$ aryl group, $C_{7-16}$ aralkyl group, $C_{1-6}$ alkyl-carbonyl group, $C_{6-14}$ aryl-carbonyl group, $C_{7-16}$ aralkyl-carbonyl group, 5 to 14 membered aromatic heterocyclyl-carbonyl group, 3 to 14 membered non-aromatic heterocyclyl-carbonyl group, $C_{1-6}$ alkoxy-carbonyl group, 5 to 14 membered aromatic heterocyclic group, carbamoyl group, mono- or di-$C_{1-6}$ alkyl-carbamoyl group, mono- or di-$C_{7-16}$ aralkyl-carbamoyl group, $C_{1-6}$ alkylsulfonyl group and $C_{6-14}$ aryl sulfonyl group, wherein each of such substituent may respectively have 1 to 3 substituent(s) selected from substituent group A" may be proposed.

Ideal examples of optionally substituted hydroxy group comprise a hydroxy group, $C_{1-6}$ alkoxy group, $C_{2-6}$ alkenyloxy group (for example, allyloxy, 2-butenyloxy, 2-pentenyloxy, 3-hexenyloxy), $C_{3-10}$ cycloalkyloxy group (for example, cyclohexyloxy), $C_{6-14}$ aryloxy group (for example, phenoxy, naphthyloxy), $C_{7-16}$ aralkyloxy group (for example, benzyloxy, phenethyloxy), $C_{1-6}$ alkyl-carbonyloxy group (for example, acetyloxy, propionyloxy, butyryloxy, isobutyryloxy, pivaloyloxy), $C_{6-14}$ aryl-carbonyloxy group (for example, benzoyloxy), $C_{7-16}$ aralkyl-carbonyloxy group (for example, benzylcarbonyloxy), 5 to 14 membered aromatic heterocyclyl-carbonyloxy group (for example, nicotinoyloxy), 3 to 14 membered non-aromatic heterocyclyl-carbonyloxy group (for example, piperidinylcarbonyloxy), $C_{1-6}$ alkoxy-carbonyloxy group (for example tert-butoxycarbonyloxy). 5 to 14 membered aromatic heterocyclyl-oxy group (for example, pyridyloxy), carbamoyloxy group, $C_{1-6}$ alkyl-carbamoyloxy group (for example, methylcarbamoyloxy), $C_{7-16}$ aralkyl-carbamoyloxy group (for example, benzylcarbamoyloxy), $C_{1-6}$ alkylsulfonyloxy group (for example, methylsulfonyloxy, ethylsulfonyloxy) and $C_{6-14}$ arylsulfonyloxy group (for example, phenylsulfonyloxy).

In this specification, as "optionally substituted sulfanyl group", for example, sulfanyl group which may have "a substituent selected from $C_{1-6}$ alkyl group, $C_{2-6}$ alkenyl group, $C_{3-10}$ cycloalkyl group, $C_{6-14}$ aryl group, $C_{7-16}$ aralkyl group, $C_{1-6}$ alkyl-carbonyl group, $C_{6-14}$ aryl-carbonyl group and 5 to 14 membered aromatic heterocyclic group, wherein each of such substituents may respectively have 1 to 3 substituents selected from substituent group A" and halogenated sulfanyl group may be proposed.

Ideal examples of optionally substituted sulfanyl group comprise a sulfanyl (—SH) group, $C_{1-6}$ alkylthio group, $C_{2-6}$ alkenylthio group (for example allylthio, 2-butenylthio, 2-pentenylthio, 3-hexenylthio), $C_{3-10}$ cycloalkylthio group (for example, cyclohexylthio), $C_{6-14}$ arylthio group (for example, phenylthio, naphthylthio), $C_{7-16}$ aralkylthio group (for example, benzylthio, phenethylthio), $C_{1-6}$ alkyl-carbonylthio group (for example, acetylthio, propionylthio, butyrylthio, isobutyrylthio, pivaloylthio), $C_{6-14}$ aryl-carbonylthio group (for example, benzoylthio), 5 to 14 membered aromatic heterocyclyl-thio group (for example, pyridylthio) and halogenated thio group (for example, pentafluorothio).

In this specification, as "optionally substituted silyl group", for example, a silyl group which may have "1 to 3 substituent(s) selected from $C_{1-6}$ alkyl group, $C_{2-6}$ alkenyl group, $C_{3-10}$ cycloalkyl group, $C_{6-14}$ aryl group and $C_{7-16}$ aralkyl group, which respectively may have 1 to 3 substituent(s) selected from substituent group A" may be proposed.

As ideal examples of optionally substituted silyl group, a tri-$C_{1-6}$ alkyl silyl group (for example trimethylsilyl and tert-butyl(dimethyl)silyl) may be proposed.

In this specification, as "$C_{1-6}$ alkylene group", for example, —$CH_2$—, —$(CH_2)_2$—, —$(CH_2)_3$—, —$(CH_2)_4$—, —$(CH_2)_5$—, —$(CH_2)_6$—, —$CH(CH_3)$—, —$(CCH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2$—$C(CH_3)_2$—, —$C(CH_3)_2$—$CH_2$—, —$CH_2$—$CH_2$—$CH_2$—$C(CH_3)_2$—, —$C(CH_3)_2$—$CH_2$—$CH_2$—$CH_2$— may be proposed.

In this specification, as "$C_{2-6}$ alkenylene group", for example, —CH=CH—, —$CH_2$—CH=CH—, —CH=CH—$CH_2$—, —$C(CH_3)_2$—CH=CH—, —CH=CH—$C(CH_3)_2$—, —$CH_2$—CH=CH—$CH_2$—, —$CH_2$—$CH_2$—CH=CH—, —CH=CH—$CH_2$—$CH_2$—, —CH=CH—CH=CH—, —CH=CH—$CH_2$—$CH_2$—$CH_2$—, —$CH_2$—$CH_2$—$CH_2$—CH=CH— may be proposed.

In this specification, as "$C_{2-6}$ alkynylene group", for example, —C≡C—, —$CH_2$—C≡C—, —C≡C—$CH_2$—, —$(CCH_3)_2$—C≡C—, —C≡C—$(CH_3)_2$—, —$CH_2$—C≡C—$CH_2$—, —$CH_2$—$CH_2$—C≡C—, —C≡C—$CH_2$—$CH_2$—, —C≡C—C≡C—, —C≡C—$CH_2$—$CH_2$—$CH_2$—, —$CH_2$—$CH_2$—$CH_2$—C≡C— may be proposed.

In this specification, as "hydrocarbon ring", for example, $C_{6-14}$ aromatic hydrocarbon ring, $C_{3-10}$ cycloalkane and $C_{3-10}$ cycloalkene may be proposed.

In this specification, as "$C_{6-14}$ aromatic hydrocarbon ring", for example, benzene and naphthalene may be proposed.

In this specification, as "$C_{3-10}$ cycloalkane", for example, cyclopropane, cyclobutane, cyclopentane, cyclohexane, cycloheptane and cyclooctane may be proposed.

In this specification, as "$C_{3-10}$ cycloalkene", for example, cyclopropene, cyclobutene, cyclopentene, cyclohexene, cycloheptene and cyclooctene may be proposed.

In this specification, as "heterocycle", for example, aromatic heterocycles and non-aromatic heterocycles respectively containing 1 to 4 heteroatom(s) selected from nitrogen atom, sulfur atom and oxygen atom in addition to the carbon atom content as ring atoms may be proposed.

In this specification, as "aromatic heterocycle", for example 5 to 14 membered (preferably 5 to 10 membered) aromatic heterocycles containing 1 to 4 heteroatom(s) selected from nitrogen atom, sulfur atom and oxygen atom in addition to the carbon atom content as ring atoms may be proposed. Ideal examples of said "aromatic heterocycle" comprise 5 to 6 membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine, etc.;
and 8 to 14 membered condensed polycyclic (preferably bi- or tri-cyclic) aromatic heterocycles such as benzothiophene, benzofuran, benzimidazole, benzoxazole, benzoisoxazole, benzothiazole, benzoisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2, 3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine, etc. may be proposed.

In this specification, as "non-aromatic heterocycle", for example, 3 to 14 membered (preferably 4 to 10 membered) non-aromatic heterocycles containing 1 to 4 heteroatom(s) selected from nitrogen atom, sulfur atom and oxygen atom in addition to the carbon atom content as ring atoms may be proposed. As ideal examples of said "non-aromatic heterocycle", 3 to 8 membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane, etc., and, 9 to 14 membered condensed polycyclic (preferably bi- or tri-cyclic) non-aromatic heterocycles such as dihydrobenzofuran, dihydrobenzoimidazole, dihydrobenzoxazole, dihydrobenzothiazole, dihydrobenzoisothiazole, dihydronaphtho[2, 3-b]thiophene, tetrahydroisoquinoline, tetrahydroquinoline, 4H-quinolidine, indoline, isoindoline, tetrahydrothieno[2, 3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbozole, tetrahydro-β-carboline, tetrahydroacridine, tetrahydrophenazine, tetrahydrothioxanthene, octahydroisoquinoline, etc. may be proposed.

In this specification, as "nitrogen-containing heterocycle", among "heterocycle", those containing at least 1 nitrogen atom as ring atoms may be proposed.

In this specification, as represented in the following formulae, when a non-aromatic ring Q condensed with an aromatic ring Q' is present, the non-aromatic ring Q forms a ring in which the bond $C^1C^2$ is a double bond.

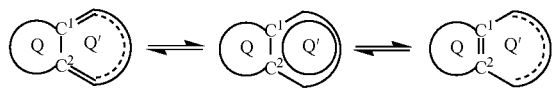

For example, when said condensed ring QQ' is an indane ring, a depiction is used whereby the non-aromatic ring Q is cyclopentene ring, and the aromatic ring Q' is benzene.

The definition of each symbol in formula (I) will now be described in detail.

Ring A is an optionally substituted 5 or 6 membered ring.
As "5 or 6 membered ring" of "optionally further substituted 5 or 6 membered ring" represented by Ring A, a benzene ring, $C_{5-6}$ cycloalkene, 5 or 6 membered monocyclic aromatic heterocycle and 5 to 6 membered monocyclic non-aromatic heterocycle may be proposed.

As said $C_{5-6}$ cycloalkene, a 5 or 6 membered cycloalkene among said "$C_{3-10}$ cycloalkene" may be proposed.

As far as said 5 to 6 membered monocyclic aromatic heterocycle is concerned, 5 to 6 membered monocycle of said "aromatic heterocycle" may be proposed.

As far as said 5-6 membered monocyclic non-aromatic heterocycle is concerned, 5 to 6 membered monocycle of said "non-aromatic heterocycle" may be proposed.

The "5 or 6 membered ring" of "optionally further substituted 5 or 6 membered ring" represented by Ring A may be further substituted by substituent selected from, for example, said substituent group A, wherein the number of substituents is, for example, 1 to 3. When the number of substituents is 2 or more, each substituent may be the same or different.

Ring A is preferably optionally further substituted $C_{5-6}$ cycloalkene (for example, cyclopentene, cyclohexene).

Ring A is more preferably $C_{5-6}$ cycloalkene (for example cyclopentene, cyclohexene).

Ring A is still more preferably cyclopentene or cyclohexene.

Ring A is particularly preferably cyclopentene.

Ring B is an optionally substituted benzene ring.
The "benzene ring" of "optionally substituted benzene ring" represented by Ring B, for example, may be substituted by substituent or substituents selected from said substituent group A, wherein the number of substituents is for example 1 to 3. When the number of substituents is 2 or more, each substituent may be the same or different.

Ring B is preferably a benzene ring optionally substituted by 1 to 3 substituent(s) selected from (1) a halogen atom (for example, fluorine atom, chlorine atom, bromine atom), and, (2) a $C_{1-6}$ alkyl group (for example, methyl).

Ring B is more preferably a benzene ring optionally substituted by 1 to 3 halogen atom(s) (for example fluorine atom, chlorine atom).

$R^1$ and $R^2$ are independently a hydrogen atom or a substituent, or $R^1$ and $R^2$ may bond together to form an optionally substituted ring.

As the "ring" of "optionally substituted ring" formed by $R^1$ and $R^2$ bonding together, non-aromatic hydrocarbon ring ($C_{3-10}$ cycloalkane, $C_{3-10}$ cycloalkene) and non-aromatic heterocycle may be proposed.

The "ring" of "optionally substituted ring" formed by $R^1$ and $R^2$ bonding together, for example, may be substituted by substituent or substituents selected from said substituent group A, wherein the number of substituents is for example 1 to 3. When the number of substituents is 2 or more, each substituent may be the same or different. Moreover, said substituent group A may also be substituted by substituent or substituents selected from substituent group A, wherein the number of substituents is for example 1 to 3. When the number of substituents is 2 or more, each substituent may be the same or different.

The "ring" of "optionally substituted ring" formed by $R^1$ and $R^2$ bonding together is preferably a 3 to 14 membered (preferably 4 to 10 membered) non-aromatic heterocycle, more preferably a 3 to 8 membered monocyclic non-aromatic heterocycle (for example, dioxolane).

$R^1$ and $R^2$ are preferably independently a hydrogen atom or an optionally substituted hydroxy group or $R^1$ and $R^2$ may bond together to form an optionally substituted 3-14 membered (preferably 4-10 membered) non-aromatic heterocycle, preferably a 3-8 membered monocyclic non-aromatic heterocycle (for example, dioxolane).

$R^1$ and $R^2$ are more preferably independently, a hydrogen atom or a hydroxy group (preferably, both are hydrogen atoms, or the one is a hydrogen atom and the other is a hydroxy group) or $R^1$ and $R^2$ may bond together to form a 3 to 14 membered (preferably 4 to 10 membered) non-aromatic heterocycle, preferably a 3 to 8 membered monocyclic non-aromatic heterocycle (for example, dioxolane), which is optionally substituted by 1 to 3 $C_{1-6}$ alkyl group(s) (for example, methyl), optionally substituted by 1 to 3 substituent(s) selected from a hydroxy group and a $C_{1-6}$ alkoxy group (for example, methoxy).

Still more preferably, (1) $R^1$ and $R^2$ are both hydrogen atoms, or (2) one of $R^1$ and $R^2$ is a hydrogen atom, and the other is a hydroxy group, or $R^1$ and $R^2$ may bond together to form a 3 to 8 membered monocyclic non-aromatic heterocycle (for example, dioxolane), which is optionally substituted by 1 to 3 $C_{1-6}$ alkyl group(s) (for example, methyl), optionally substituted by 1 to 3 substituent(s) selected from a hydroxy group and a $C_{1-6}$ alkoxy group (for example, methoxy).

Particularly preferably, $R^1$ and $R^2$ may bond together to form a 3 to 14 membered (preferably 4 to 10 membered) non-aromatic heterocycle (preferably 3 to 8 membered monocyclic non-aromatic heterocycle (for example, dioxolane)), which is optionally substituted by 1 to 3 $C_{1-6}$ alkyl group(s) (for example, methyl), optionally substituted by 1 to 3 substituent(s) selected from a hydroxy group and a $C_{1-6}$ alkoxy group (for example, methoxy).

W is $CH_2$, NH or O.

W is preferably $CH_2$ or O.

W is more preferably $CH_2$.

$R^3$ is a substituent.

$R^3$ is preferably an optionally substituted hydroxy group. Substituent (substituent group A) on the optionally substituted hydroxy group may also be substituted by substituent selected from substituent group A, wherein the number of substituents is, for example, 1 to 3. When the number of substituents is 2 or more, each substituent may be the same or different.

$R^3$ is more preferably an optionally substituted $C_{1-6}$ alkoxy group (for example, methoxy, ethoxy).

$R^3$ is further more preferably a $C_{1-6}$ alkoxy group (for example, methoxy, ethoxy) optionally substituted by 1 to 3 $C_{3-10}$ cycloalkyl group(s) (for example, cyclopropyl) optionally substituted by 1 to 3 $C_{1-6}$ alkyl group(s) (for example, methyl).

$R^3$ is still more preferably a $C_{1-6}$ alkoxy group (for example, ethoxy).

The following compounds may be proposed as ideal compounds (I).

Compound A
Compound (I),
wherein,
Ring A is $C_{5-6}$ cycloalkene (for example, cyclopentene, cyclohexene) which may be further substituted,
Ring B is optionally substituted benzene ring,
$R^1$ and $R^2$ are independently hydrogen atom or optionally substituted hydroxy group, or $R^1$ and $R^2$ may bond together to form an optionally substituted 3 to 14 membered (preferably 4 to 10 membered) non-aromatic heterocycle, preferably a 3 to 8 membered monocyclic non-aromatic heterocycle (for example, dioxolane), W is $CH_2$ or O, and, $R^3$ is an optionally substituted $C_{1-6}$ alkoxy group (for example, methoxy, ethoxy).

Compound B
Compound (I),
wherein,
Ring A is $C_{5-6}$ cycloalkene (for example cyclopentene, cyclohexene),
Ring B is a benzene ring optionally substituted by 1 to 3 substituent(s) selected from
(1) a halogen atom (for example, fluorine atom, chlorine atom, bromine atom), and,
(2) a $C_{1-6}$ alkyl group (for example, methyl),
$R^1$ and $R^2$ are independently a hydrogen atom or a hydroxy group (preferably, both are hydrogen atom or the one is a hydrogen atom and the other is a hydroxy group) or $R^1$ and $R^2$ may bond together to form a 3-14 membered (preferably 4-10 members) non-aromatic heterocycle (preferably 3-8 membered monocyclic non-aromatic heterocycle (for example, dioxolane)) optionally substituted by 1 to 3 $C_{1-6}$ alkyl group(s) (for example, methyl), optionally substituted by 1 to 3 substituent(s) selected from a hydroxy group and a $C_{1-6}$ alkoxy group (for example, methoxy), W is $CH_2$ or O, and, $R^3$ is a $C_{1-6}$ alkoxy group (for example, methoxy, ethoxy) optionally substituted by 1 to 3 $C_{3-10}$ cycloalkyl group(s) (for example, cyclopropyl) optionally substituted by 1 to 3 $C_{1-6}$ alkyl group(s) (for example, methyl).

Compound C
Compound (I),
wherein,
Ring A is cyclopentene or cyclohexene,
Ring B is a benzene ring optionally substituted by 1 to 3 substituent(s) selected from
(1) a halogen atom (for example, fluorine atom, chlorine atom, bromine atom), and,
(2) a $C_{1-6}$ alkyl group (for example, methyl),
As to $R^1$ and $R^2$, (1) $R^1$ and $R^2$ are both hydrogen atoms, or (2) one of $R^1$ and $R^2$ is a hydrogen atom, and the other is a hydroxy group, or $R^1$ and $R^2$ may bond together to form a 3 to 8 membered monocyclic non-aromatic heterocycle (for example, dioxolane), which is optionally substituted by 1 to 3 $C_{1-6}$ alkyl group(s) (for example, methyl), optionally substituted by 1 to 3 substituent(s) selected from a hydroxy group and a $C_{1-6}$ alkoxy group (for example, methoxy), W is $CH_2$ or O, and, $R^3$ is a $C_{1-6}$ alkoxy group (for example, methoxy, ethoxy) optionally substituted by 1 to 3 $C_{3-10}$ cycloalkyl group(s) (for example, cyclopropyl) optionally substituted by 1 to 3 $C_{1-6}$ alkyl group(s) (for example, methyl).

Compound D
Compound (I), wherein,
Ring A is $C_{5-6}$ cycloalkene (for example, cyclopentene, cyclohexene),
Ring B is a benzene ring optionally substituted by 1 to 3 halogen atom(s) (for example fluorine atom, chlorine atom),
$R^1$ and $R^2$ may bond together to form a 3 to 14 membered (preferably 4 to 10 membered) non-aromatic heterocycle (preferably 3 to 8 membered monocyclic non-aromatic heterocycle (for example, dioxolane)), optionally substituted by 1 to 3 $C_{1-6}$ alkyl group(s) (for example, methyl) optionally substituted by 1 to 3 substituent(s) selected from a hydroxy group and a $C_{1-6}$ alkoxy group (for example, methoxy), W is CH$_2$, and,
R$^3$ is a C$_{1-6}$ alkoxy group (for example, ethoxy).

The compounds of Example 1-21 may be proposed as specific examples of said compound (I). Among them, ethyl (2R,3R,8R)-8-(((1S)-7-chloro-2,3-dihydro-1H-inden-1-yl)sulfonyl)-2,3-bis(hydroxymethyl)-1,4-dioxaspiro[4.5]dec-6-ene-7-carboxylate (Example 6), ethyl (2R,3R,8R)-8-(((1S)-7-chloro-5-fluoro-2,3-dihydro-1H-inden-1-yl)sulfonyl)-2,3-bis(hydroxymethyl)-1,4-dioxaspiro[4.5]dec-6-ene-7-carboxylate (Example 14), and ethyl (2R,3R,8R)-8-(((1S)-7-chloro-2,3-dihydro-1H-inden-1-yl)sulfonyl)-2,3-bis(methoxymethyl)-1,4-dioxaspiro[4.5]dec-6-ene-7-carboxylate (Example 21) are preferable.

When compound (I) is a salt, as such salts, for example, metal salts, ammonium salts, salts with organic bases, salts with inorganic acids, salts with organic acids, salts with basic or acidic amino acids, etc., may be proposed. Ideal examples of metal salts include alkali metal salts such as sodium salts, potassium salts, etc., alkaline earth metal salts such as calcium salts, magnesium salts, barium salts, etc., aluminum salts, etc. Ideal examples of salts with organic base include salts with, for example, trimethylamine, triethylamine, pyridine, nicotine, 2, 6-lutidine, ethanolamine, diethanolamine, triethanolamine, cyclohexylamine, dicyclohexylamine, N, N'-dibenzylethylenediamine, etc. Ideal examples of salts with inorganic acids, include salts with, for example, hydrochloric acid, hydrobromic acid, nitric acid, sulfuric acid, phosphoric acid, etc. Ideal examples of salts with organic acids, include salts with, for example, formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Ideal examples of salts with basic amino acids, include salts with, for example, arginine, lysine, ornithine, etc., and as ideal examples of salts with acidic amino acids, salts with, for example, aspartic acid, glutamic acid, etc. may be proposed.

Among these, pharmacologically permitted salts are preferred. For example, when the compound has acid functionality, inorganic salts such as alkali metal salts (for example, sodium salt, potassium salt, etc.), alkaline earth metal salts (for example, calcium salt, magnesium salt, etc.), etc. and ammonium salts may be proposed; and when the compound has basic functionality, salts with inorganic acids such as hydrochloric acid, hydrobromic acid, nitric acid, sulfuric acid, phosphoric acid, etc., and salts with organic acids such as acetic acid, phthalic acid, fumaric acid, oxalic acid, tartaric acid, maleic acid, citric acid, succinic acid, methanesulfonic acid, benzenesulfonic acid, p-toluenesulfonic acid, etc. may be proposed.

Processes for Production

Processes for the production of the compounds of the present invention will now be described.

Starting materials and reagents used in any of the steps in the following processes for production and the obtained compounds may be in the form of a respective salt. As examples of such salts, the same kinds of salts as the said salts of the compounds of the present invention may be proposed.

When the compound obtained in any of the steps is the free compound, said free compound can be converted to a target salt using by itself a well-known process. Conversely, when the compound obtained in any of the steps is a salt, said salt can be converted to the free body or another type of intended salt by itself well-known process.

The compound obtained in any of the steps may be used in the following reaction either still in the form of the reaction liquid, or after obtaining the crude product. Alternatively, the compound obtained in each of the steps can be isolated and/or purified from the reaction mixture by a separation means such as concentration, crystallization, recrystallization, distillation, solvent extraction, fractionating, chromatography, etc. in accordance with conventional procedures.

If a raw material or reagent in any of the steps is a marketed, commercial product, then such a product can be used.

In the reactions in any of the steps, the reaction time can differ depending on the reagent and solvent used, but unless otherwise specifically stated, said reaction time is usually 1 min to 48 hours, preferably 10 mins to 8 hours.

In the reactions in any of the steps, the reaction temperature can differ depending on the reagent and solvent used, but unless otherwise specifically stated, said reaction temperature is usually −78° C. to 300° C., preferably −78° to 150° C.

In the reactions in any of the steps, the pressure can differ depending on the reagent and solvent used, but unless otherwise specifically stated, said pressure is usually 1 atmosphere to 20 atmospheres, preferably 1 atmosphere to 3 atmospheres.

In the reactions in any of the steps, for example, a microwave synthesizing apparatus such as an Initiator made by the Biotage Corporation may be used. The reaction temperature can differ depending on the reagents and solvent used, but unless otherwise specifically stated, the reaction temperature is usually room temperature to 300° C., preferably 50° to 250° C. The reaction time can differ depending on the reagents and solvent used, but unless otherwise specifically stated, the reaction time is usually 1 min to 48 hours, preferably 1 min to 8 hours.

In the reactions in any of the steps, unless otherwise specifically stated to the contrary, 0.5 equivalents to 20 equivalents, more preferably 0.8 equivalents to 5 equivalents reagent are used with respect to the substrate. When the reagent is used as a catalyst, 0.001 equivalents to 1 equivalent, more preferably 0.01 equivalents to 0.2 equivalents reagent is used with respect to the substrate. When the reagent serves as the reaction solvent, the reagent is used in the amount of solvent.

In the reactions in any of the steps, unless otherwise specifically stated to the contrary, such reactions may be performed in the absence of solvent or with dissolution or suspension in a suitable solvent. As specific examples, those solvents described later in the Examples, or those given below may be proposed:

Alcohols: methanol, ethanol, tert-butyl alcohol, 2-methoxyethanol, etc.,
Ethers: diethyl ether, diphenyl ether, tetrahydrofuran, 1,2-dimethoxyethane, etc.,
Aromatic hydrocarbons: chlorobenzene, toluene, xylene, etc.,
Saturated hydrocarbons: cyclohexane, hexane, etc.,
Amides: N,N-dimethylformamide, N-methylpyrrolidone, etc.,
Halogenated hydrocarbons: dichloromethane, carbon tetrachloride, etc.,
Nitriles: acetonitrile, etc.,
Sulfoxides: dimethyl sulfoxide, etc.,
Aromatic organic bases types: pyridine, etc.,
Acid anhydrides: acetic anhydride, etc., Organic acids: formic acid, acetic acid, trifluoroacetic acid, etc.,
Inorganic acids: hydrochloric acid, sulfuric acid, etc.,
Esters: ethyl acetate, etc.,
Ketones: acetone, methyl ethyl ketone, etc.,
Water.
Said solvents may be used in a combination of two or more thereof in suitable proportions.

When base is used in the reactions in any of the steps, for example, a base shown below or a base described in the Examples may be used.
Inorganic bases: sodium hydroxide, magnesium hydroxide, sodium carbonate, calcium carbonate, sodium bicarbonate, etc.,
Organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, etc.,
Metal alkoxides: sodium ethoxide, potassium tert-butoxide, etc.,
Alkali metal hydrides: sodium hydride, etc.,
Metallic amides: sodium amide, lithium diisopropylamide, lithium hexamethyl disilazide, etc.,
Organolithiums: n-butyllithium, etc.

When acid or acid catalyst is used in the reactions in any of the steps, for example, an acid or acidic catalyst shown below, or an acid or acidic catalyst described in the Examples, may be used.
Inorganic acids: hydrochloric acid, sulfuric acid, nitric acid, hydrobromic acid, phosphoric acid, etc.,
Organic acids: acetic acid, trifluoroacetic acid, citric acid, p-toluenesulfonic acid, 10-camphor sulfonic acid, etc.,
Lewis acids: Boron trifluoride diethyl ether complex, zinc iodide, anhydrous aluminum chloride, anhydrous zinc chloride lead, anhydrous iron chloride, etc.

The reactions in any of the steps are not restricted unless otherwise specifically stated, and can be performed in accordance with processes that are in themselves well-known, for example, processes as described in the Fifth Series of Experimental Chemistry, Vol. 13 to 19, (The Chemical Society of Japan); New Experimental Chemistry Course, Vol. 14 to 15 (The Chemical Society of Japan); Fine Organic Chemistry, Revised Second Edition (L. F. Tietze, Th. Eicher, Nankodo); Revised Organic Name Reactions, their mechanism and essence (Hideo Togo, Kodansha); ORGANIC SYNTHESES Collective Volume I to VII (John Wiley & Sons Inc); Modern Organic Synthesis in the Laboratory A Collection of Standard Experimental Procedures (Jie Jack Li, OXFORD UNIVERSITY Publication); Comprehensive Heterocyclic Chemistry III, Vol. 1 to Vol. 14 (Elsevier Japan Co. Ltd.); Strategic Applications of Named Reactions in Organic Synthesis (Translation Supervised by Tomioka Kiyoshi, Kagaku Dojin Publication), Comprehensive Organic Transformations (VCH Publishers Inc) 1989, etc., or in accordance with processes as described in the Examples.

In each step, protecting or deprotecting reactions for the functional groups are performed in accordance with processes which are in themselves well-known, for examples, processes described in "Protective Groups in Groups in Organic Synthesis, 4th Ed." (Theodora W. Greene, Peter G. M. Wuts) published by Wiley-Interscience in 2007; or "Protecting Groups 3rd Ed." (P. J. Kocienski) published by Thieme in 2004; or in accordance with processes described in the Examples.

In the case of hydroxy groups of protected alcohols and phenolic hydroxy groups, for example, ether groups such as methoxymethyl ether, benzyl ether, tert-butyldimethylsilyl ether, tetrahydropyranyl ether, etc.; carboxylate ester groups such as acetic acid ester, etc.; sulfonic acid ester groups such as methanesulfonic ester, etc.; carbonic acid ester groups such as tert-butyl carbonate, etc., and the like, may be proposed.

In the case of carbonyl groups of protected aldehydes, for example, acetal groups such as dimethyl acetal, etc.; cyclic acetal groups such as 1,3-dioxane, etc., and the like may be proposed.

In the case of carbonyl groups of protected ketones, for example, ketal groups such as dimethyl ketal, etc., cyclic ketal groups such as 1,3,-dioxane, etc., oxime group such as O-methyloxime, etc., hydrazone groups such as N,N-dimethylhydrazone, etc., and the like, may be proposed.

In the case of protected carboxyl groups, for example, ester groups such as methyl ester, etc., amide groups, etc. such as N,N-dimethyl amide, etc., and the like, may be proposed.

In the case of protected thiols, for example, ether groups such as benzylthio ether, etc., ester groups such as thioacetic acid ester, thiocarbonate, thiocarbamate, etc., and the like may be proposed.

In the case of protected amino groups and aromatic heterocycles such as imidazole, pyrrole, indole, etc., carbamate groups such as benzyl carbamate, etc., amide groups such as acetamide, etc., alkylamine groups such as N-triphenylmethylamine, etc., sulfonamide groups such as methane sulfonamide, etc., and the like, may be proposed.

The elimination of the protecting groups can be carried out using itself well-known process, for example a process using acid, base, UV light, hydrazine, phenylhydrazine, sodium N-methyl dithiocarbamate, tetrabutylammonium fluoride, palladium acetate, trialkylsilyl halide (for example, trimethylsilyl iodide, trimethylsilyl bromide), or reducing method or the like.

When a reducing reaction is performed in any of the steps, the reducing agent used may comprise, for example, a metal hydride such as lithium aluminum hydride, sodium acetoxy borohydride, sodium cyanoborohydride, diisobutylaluminium hydride (DIBAL-H), sodium borohydride, acetoxy borohydride tetramethylammonium, etc., a borane such as borane tetrahydrofuran complex, etc., Raney nickel, Raney cobalt, hydrogen, formic acid, etc. When a carbon-carbon double bond or triple bond is being reduced, a process using a catalyst such as a palladium-carbon catalyst, Lindlar catalyst, etc. may be applied.

When an oxidation reaction is performed in any of the steps, the oxidizing agent used may comprise a peroxy acid such as m-chloroperbenzoic acid (MCPBA), hydrogen peroxide, tert-butylhydroperoxide, etc., a perchlorate salt such as tetrabutylammonium perchlorate, etc., a chlorate salt such as sodium chlorate, etc., a chlorite such as sodium chlorite, etc., a periodate such as sodium periodate, etc., a high atomic valency iodine reagent such as iodosobenzene, etc., a reagent containing manganese such as manganese dioxide, potassium permanganate, etc., a lead compound such as lead tetraacetate, etc., a reagent containing chromium such as pyridinium chlorochromate (PCC), pyridinium dichromate (PDC), Jones reagent, etc., a halogen compound such as N-bromo succinimide (NBS), etc., oxygen, ozone, sulfur trioxide/pyridine complex, osmium tetroxide, selenium dioxide, 2,3-dichloro-5,6-dicyano-1,4-benzoquinone (DDQ), etc.

When a radical cyclization reaction is performed in any of the steps, the radical initiator which is used may comprise an azo compound such as azobisisobutyronitrile (AIBN), etc.;

a water-soluble radical initiator such as 4-4'-azobis-4-cyanopentanoic acid (ACPA), etc.; triethyl boron in the presence of air or of oxygen; benzoyl peroxide, etc. Moreover, as far as the radical reaction reagent used is concerned, tributylstannane, tris trimethylsilyl silane, 1,1,2,2-tetraphenyldisilane, diphenylsilane, samarium iodide, etc. may be proposed.

When a Wittig reaction is performed in any of the steps, an alkylidene phosphorane, etc. may be proposed as the Wittig reagent used. An alkylidene phosphorane can be prepared by itself a well-known process, such as, for example, the reaction of a phosphonium salt with strong base.

In any of the steps, when a Horner-Emmons reaction is performed, the reagent used may comprise a phosphonoacetic acid ester such as methyl dimethylphosphonoacetate, ethyl diethylphosphonoacetate, etc., a base such as an alkali metal hydride, an organolithium, etc.

When a Friedel-Crafts reaction is performed in any of the steps, the reagent used may comprise a combination of Lewis acid and acid chloride or a combination of Lewis acid and alkylating agent (for example alkyl halide, alcohol, olefin, etc.) may be proposed. Alternatively, an organic acid and/or inorganic acid can be used instead of the Lewis acid, and an acid anhydride such as acetic anhydride, etc. can be used instead of the acid chloride.

When an aromatic nucleophilic substitution reaction is performed in any of the steps, as the reagent used a nucleophilic reagent (for example, amine, imidazole, etc.) and base (for example, organic base, etc.) may be used.

In any of the steps, when a nucleophilic addition reaction using a carbanion, a nucleophilic 1,4-addition reaction using a carbanion (Michael addition reaction) or a nucleophilic substitution reaction using a carbanion, is performed, as the base used to generate the carbanion, an organolithium, metal alkoxide, inorganic base, organic base, etc. may be proposed.

When a Grignard reaction is performed in any of the steps, the Grignard reagent may comprise an aryl magnesium halide such as phenylmagnesium bromide, etc., an alkylmagnesium halide such as methyl magnesium bromide, etc. The Grignard reagent can be prepared by itself wellknown process, for example, by reacting metal magnesium with alkyl halide or aryl halide in tetrahydrofuran or ether as solvent.

In any of the steps, when a Knoevenagel condensation reaction is performed, the reagents used may comprise an active methylene compound with two electrophilic groups (for example, malonic acid, diethyl malonate, malonitrile, etc.) and base (for example organic base, metal alkoxide, inorganic base).

When a Vilsmeier-Haack reaction is performed in any of the steps, the reagent used may comprise a phosphorus oxychloride and an amide derivative (for example N,N-dimethylformamide, etc.).

In any of the steps, when an azide forming reaction is performed with an alcohol, alkyl halide or sulfonate, as the azide forming agent which is used, diphenylphosphoryl azide (DPPA), trimethylsilyl azide, sodium azide, etc. may be proposed. For example, when an alcohol is subjected to azide formation, for example, a process using diphenylphosphoryl azide and 1, 8-diazabicyclo[5.4.0]undec-7-ene (DBU) or a process using trimethylsilyl azide and Lewis acid, may be applied.

When a reductive amination reaction is performed in any of the steps, the reducing agent used may comprise sodium acetoxyborohydride, sodium cyanoborohydride, hydrogen, formic acid, etc. When the substrate is as amine compound, as the carbonyl compound used, in addition to paraformaldehyde, an aldehyde such as acetaldehyde, etc., a ketone such as cyclohexanone, etc. may be proposed. When the substrate is a carbonyl compound, as the amine used, ammonia, a primary amine such as methylamine, etc., or a secondary amine such as dimethylamine, etc., or the like may be proposed.

When a Mitsunobu reaction is performed in any of the steps, as the reagent used, azodicarboxylic acid ester (for example, diethyl azodicarboxylate (DEAD), diisopropyl azodicarboxylate (DIAD), etc.) and triphenylphosphine may be used.

In any of the steps, when an esterification reaction, amidation reaction or urea-forming reaction is performed, as the reagent which is used, a halogenated acyl compound such as acid chloride, acid bromide, etc., an activated carboxylic acid compound such as acid anhydride, active ester, sulfate ester, etc. may be proposed. As carboxylic acid activating agent, a carbodiimide-based condensing agent such as 1-ethyl-3-(3-dimethylaminopropyl) carbodiimide hydrochloride (WSCD), etc.; a triazine-based condensing agent such as 4-(4,6-dimethoxy-1,3,5-triazine-2-yl)-4-methyl morpholinium chloride-n-hydrate (DMT-MM); a carbonate ester-based condensing agent such as 1,1-carbonyldiimidazole (CDI), etc.; diphenylphosphorazidate (DPPA); benzotriazol-1-yloxy-tris dimethylamino phosphonium salt (BOP reagent); 2-chloro-1-methyl-pyridinium iodide (Mukaiyama reagent); thionyl chloride, a halo formic acid lower alkyl ester such as ethyl chloroformate, etc.; O-(7-azabenzotriazol-1-yl)-N,N,N',N'-tetramethyluronium hexafluorophosphate (HATU); sulfuric acid; or combinations of these, etc. may be proposed. When a carbodiimide-based condensing agent is used, an additive such as 1-hydroxy benzotriazole (HOBt), N-hydroxy succinimide (HOSu), dimethylaminopyridine (DMAP), etc. may also be added to the reaction.

When a coupling the reaction is performed in any of the steps, as the metal catalyst used, a palladium compound such as palladium (II) acetate, tetrakis(triphenylphosphine)palladium (0), dichlorobis(triphenylphosphine)palladium (II), dichlorobis(triethylphosphine)palladium (II), tris(dibenzylideneacetone)dipalladium (0), 1,1'-bis(diphenylphosphino)ferrocene palladium (II) chloride, palladium (II) acetate, etc.; a nickel compound such as tetrakis(triphenylphosphine)nickel (0), etc.; a rhodium compound such as tris(triphenylphosphine)rhodium (III) chloride, etc.; a cobalt compound; a copper compound such as copper oxide, copper (I) iodide, etc.; a platinum compound, etc. may be proposed. Moreover, base may be added to the reaction, and as such base, inorganic bases, etc. may be proposed.

When a thiocarbonylation reaction is performed in any of the steps, as thiocarbonylation agent, typically phosphorous pentasulfide is used, but other than phosphorous pentasulfide, a reagent having a 1,3,2,4-dithiadiphosphetane-2,4-disulfide structure such as 2, 4-bis(4-methoxyphenyl-1, 3, 2,4-dithiadiphosphetane-2,4-disulfide (Lawesson reagent) may be used.

When a Wohl-Ziegler reaction is performed in any of the steps, the halogenating agent, may comprise N-iodosuccinimide, N-bromosuccinimide (NBS), N-chlorosuccinimide (NCS), bromine, chlorosulfuric acid, etc. Moreover, the reaction can be accelerated by applying heat, light, radical initiator such as benzoyl peroxide, azobisisobutyronitrile, etc. to the reaction.

When a hydroxy group halogenation is performed in any of the steps, the halogenating agent used comprises an acid halide compound of an inorganic acid with hydrohalic acid; specific examples include in the case of chlorination, hydrochloric acid, thionyl chloride, phosphorus oxychloride, etc.; and in the case of bromination, 48% hydrobromic acid, etc. Moreover, a process to obtain alkyl halide from alcohol based on the action of triphenylphosphine and carbon tetrachloride or carbon tetrabromide, etc. may be used. Alternatively, a method via a two stage reaction may be applied, wherein an alcohol is first converted to sulfonic acid ester, and then the alkyl halide synthesized by reaction with lithium bromide, lithium chloride or sodium iodide.

When an Arbuzov reaction is performed in any of the steps, the reagent used may comprise an alkyl halide such as ethyl bromoacetate, etc., a phosphite such as triethyl phosphite or tri(isopropyl) phosphite, etc.

When a sulfonic acid ester forming reaction is performed in any of the steps, examples of sulfonylating agent used include methanesulfonyl chloride, p-toluenesulfonyl chloride, methanesulfonic acid anhydride, p-toluenesulfonic acid anhydride and the like.

When a hydrolysis reaction is performed in any of the steps, an acid or base is used as the reagent. Moreover, when acid hydrolysis of tert-butyl ester is performed, formic acid and/or triethylsilane, etc. can be added in order to trap by-produced tert-butyl cations using reduction.

When a dehydration reaction is performed in any of the steps, as the dehydrating agent used, sulfuric acid, diphosphorous pentoxide, phosphorus oxychloride, N,N-dicyclohexylcarbodiimide, alumina, polyphosphoric acid, etc. may be proposed.

Compound (I) can be produced by the following process from Compound (2).

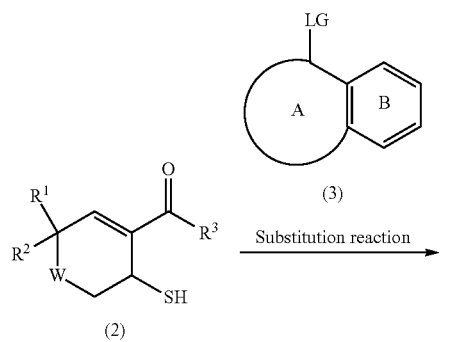

(3)

Substitution reaction

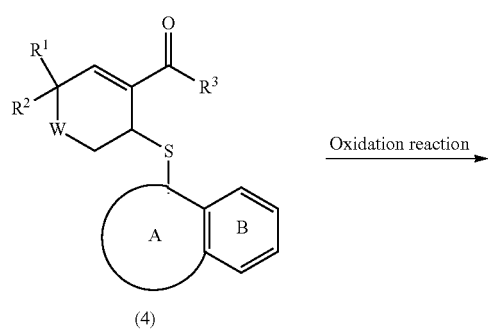

Oxidation reaction (4)

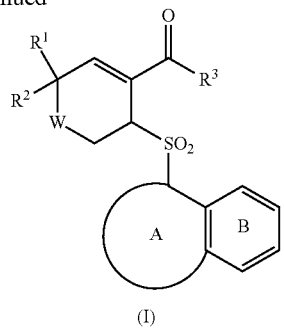

(I)

(wherein, LG is a leaving group, and the other symbols have the same said meanings)

As leaving group represented by LG, for example, a halogen atom (chlorine atom, bromine atom, iodine atom, etc.), substituted sulfonyloxy group ($C_{1-6}$ alkylsulfonyloxy group such as methane sulfonyloxy, ethane sulfonyloxy, etc.; $C_{6-14}$ aryl sulfonyloxy group such as benzene sulfonyloxy, p-toluene sulfonyloxy, etc.; $C_{7-16}$ aralkyl sulfonyloxy group, etc. such as benzyl sulfonyloxy group, etc.), acyloxy group (acetoxy, benzoyloxy, etc.) and the like may be proposed.

Compound (4) can be produced from Compound (2) by performing a substitution reaction using Compound (3) in the presence of base.

Compound (3) can be synthesized by the following process from Compound (5).

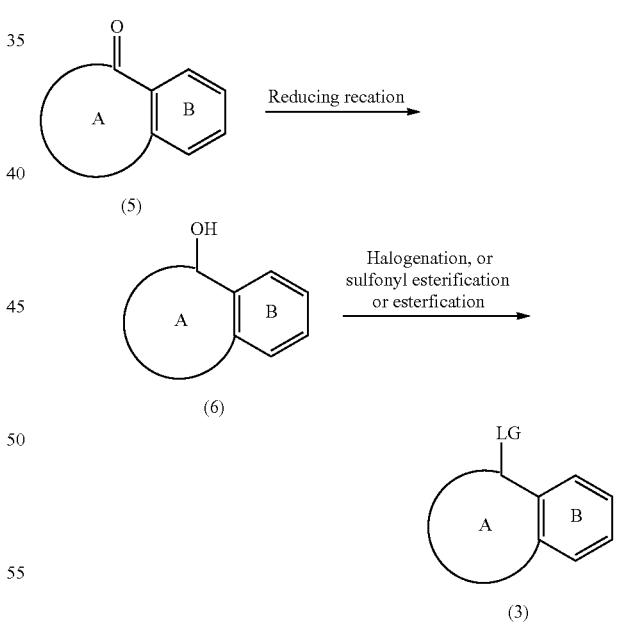

(wherein, LG has the same said meaning)

Compound (5) may be a commercial product, or can be produced by a well-known process or a process based on such a process.

Compound (2) can be synthesized in accordance with itself well-known method; and for example, Compound (2a) can be produced by the following process from Compound (7).

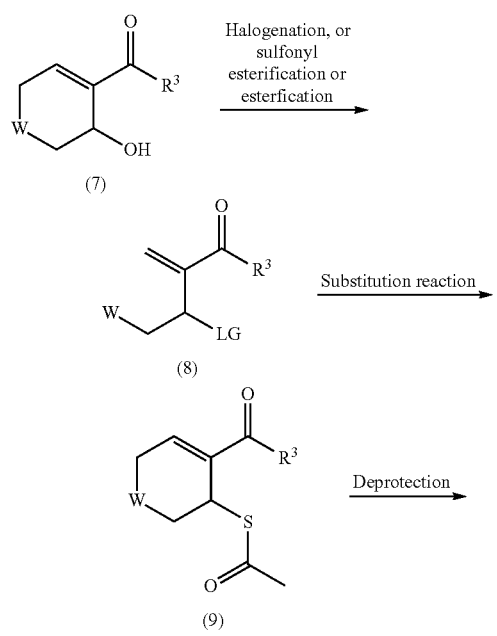

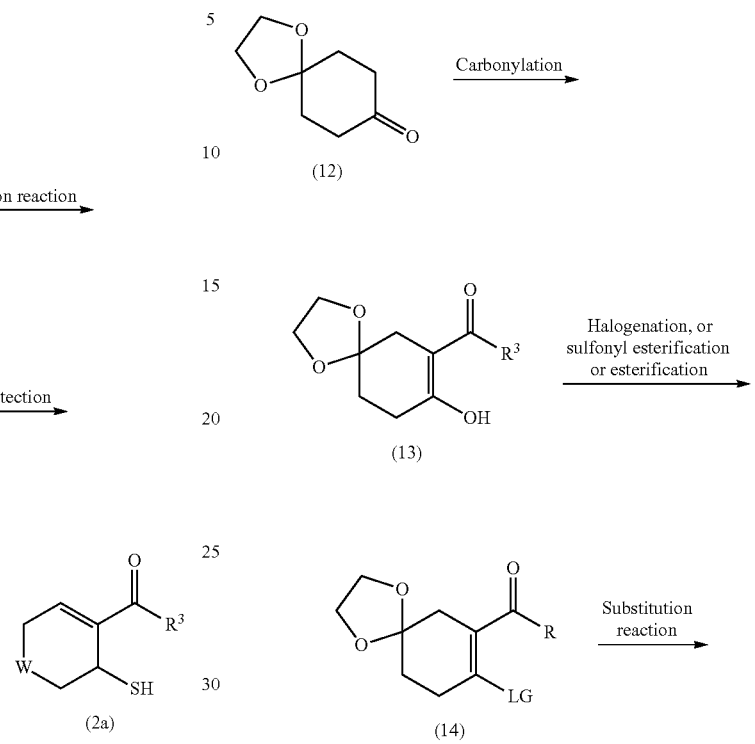

(wherein, each symbol has the same said meaning)

Compound (9) can be produced from Compound (8) by a substitution reaction using thioacetic acid or a thioacetate salt, in the presence of base. As the salt of thioacetic acid, the potassium salt, sodium salt, etc. may be proposed.

Compound (7) can be synthesized in accordance with itself well-known method; and for example, Compound (7a) can be synthesized in accordance with a process which is well-known in the literature (Synthetic Communications, 16(2), 149-156 (1986)).

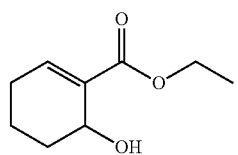

(7a)

Moreover, Compound (7), when Compound (7b), can be synthesized in accordance with a process well-known in the literature (WO2011/093512A1).

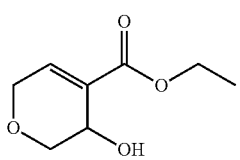

(7b)

Compound (2), when Compound (2b), can be produced by the following process from Compound (12).

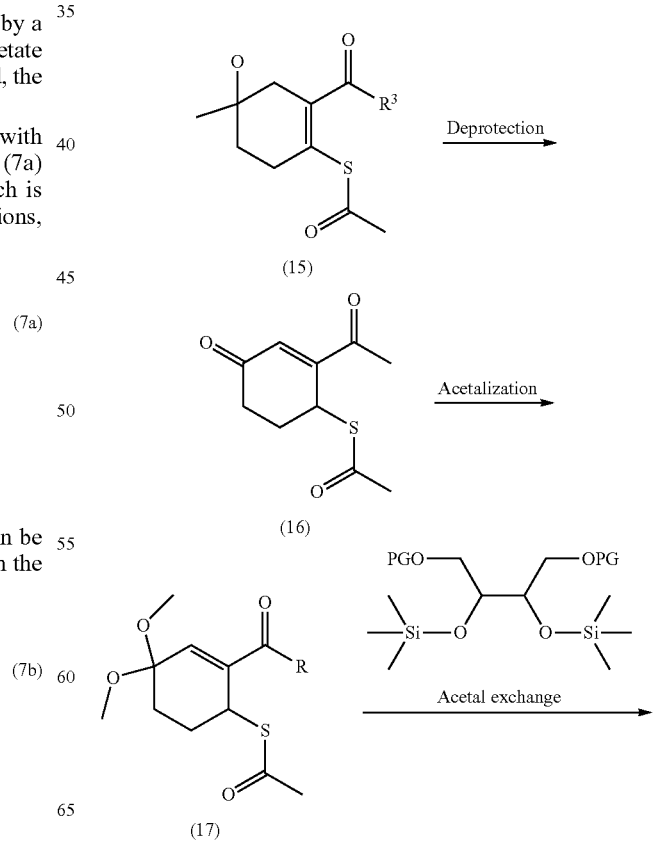

-continued

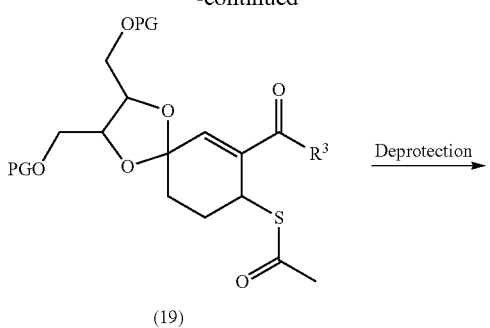

(19)

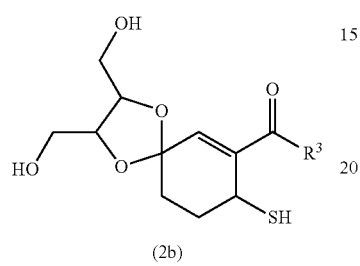

(2b)

(wherein, PG is a protecting group, and the other symbols have the same said meanings)

Compound (13) can be produced from Compound (12) by carbonylation using a carbonylation reagent in the presence of base. As carbonylation reagent, diethyl carbonate, ethyl chloroformate, acetyl chloride, acetic anhydride, N,N-dimethylformamide may be proposed.

Compound (15) can be produced by a substitution reaction of Compound (14) using thioacetic acid or a thioacetate salt, in the presence of base. As the salt of thioacetic acid, the potassium salt, sodium salt, etc. may be proposed.

Compound (19) can be produced from Compound (18) using an acetal-exchange reaction in the presence of acid.

Compound (18) can be synthesized by the following process from Compound (20).

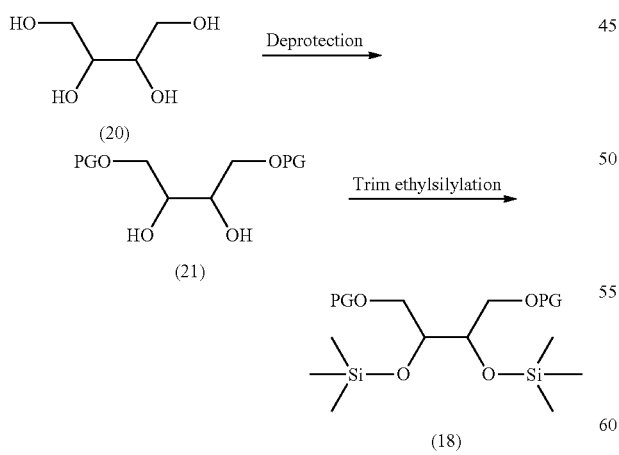

(wherein, each symbol has the same said meaning)

Compound (12) and Compound (20) may be commercial products, or can be produced by well-known processes or processes based on such processes.

Compound (2), when Compound (2c), can be produced by the following process from Compound (16).

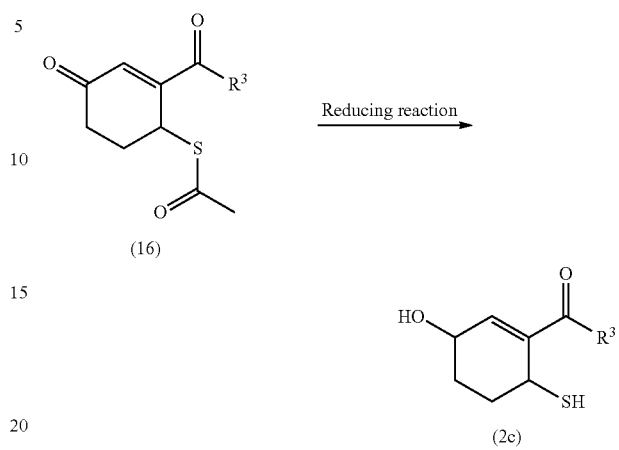

(wherein, each symbol has the same said meaning).

Compound (4), when Compound (4b), can be produced by the following process from Compound (2b).

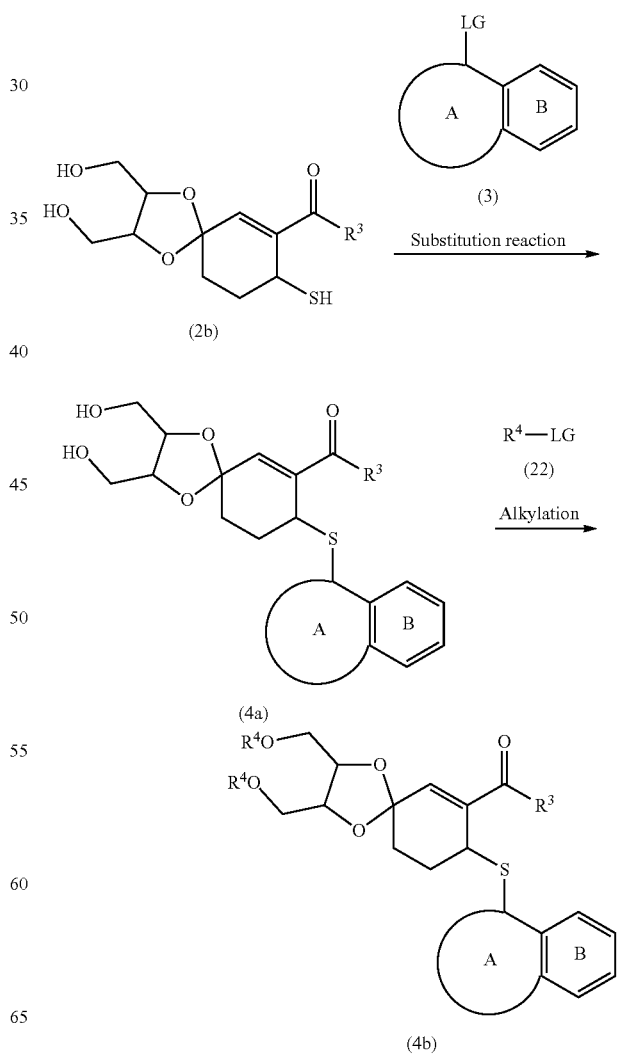

(wherein, $R^4$ is an optionally substituted alkyl group, and the other symbols have the same said meanings)

Compound (4a) can be produced from Compound (2b) by a substitution reaction using Compound (3) in the presence of base.

Compound (4b) can be produced from Compound (4a) by alkylation using Compound (22) in the presence of base.

A marketed product may be used as Compound (22) or it can be prepared by a well-known process or a process based on such a process.

When Compound (I) includes optical isomers, stereoisomers, positional isomers or rotational isomers, these are also included within Compound (I), and also, these can be obtained as respectively isolated products by in themselves well-known synthesis techniques and separational techniques (for example, concentration, solvent extraction, column chromatography, recrystallization, etc.). For example, when optical isomers are present in Compound (I), the optical isomers resolved from said compound are also included within Compound (I).

Optical isomers can be produced using in themselves well-known processes. More specifically, optical isomers may be obtained by using an optically active intermediate or by resolving the final racemate product in accordance with conventional procedures.

As optical resolution method, itself well-known process, for example a fractional crystallization method, chiral column method, diastereomer method, etc. is used.

1) Fractional Crystallization Method

A method wherein a salt is formed between the racemate and an optically active compound (for example, (+)-mandelic acid, (−)-mandelic acid, (+)-tartaric acid, (−)-tartaric acid, (+)-1-phenethyl amine, (−)-1-phenethyl amine, cinchonine, (−)-cinchonidine, brucine, etc.), and this then separated by a fractional crystallization method, and then in accordance with requirements, the free optical isomer is obtained via a neutralization step.

2) Chiral Column Method

A method wherein the racemate or a salt thereof is separated using a column for optical isomer separation (a chiral column). For example, in the case of liquid chromatography, the mixture of optical isomers is added to ENANTIO-OVM (made by Tosoh Corp.) or one of the CHIRAL series (made by Daicel Chemical Industries Ltd.), and development performed with a solution comprising one of, or a mixture of, water, various buffers (for example phosphate-buffer solution, etc.) and organic solvent (for example, ethanol, methanol, 2-propanol, acetonitrile, trifluoroacetic acid, diethylamine, etc.), and the optical isomers thereby separated. Moreover, for example, in the case of gas chromatography, a chiral column such as CP-Chirasil-DeX CB (made by GL Sciences Inc.), etc. may be used to cause separation.

3) Diastereomer Method

A method wherein the racemic mixture is formed into a mixture of diastereomers by a chemical reaction with an optically active reagent, and then this mixture formed into the single substances via conventional separational means (for example, fractional crystallization, chromatography method, etc.), etc., and then the optical isomers obtained by cleaving the optically active reagent position by a chemical treatment such as hydrolysis reaction, etc. For example, when compound (I) contains an hydroxy or a primary or secondary amino within the molecule, the diastereomer of the ester or amide compound is respectively obtained by subjection of said compound to a condensation reaction with an optically active organic acid (for example, MTPA [α-methoxy-α-(trifluoromethyl)phenyl acetic acid], (−)-methoxy acetic acid, etc.). On the other hand, when compound (I) contains a carboxy group, the diastereomer of the ester or amide is respectively obtained by subjection of said compound to a condensation reaction with an optically active amine or alcohol reagent. The separated diastereomer may then be converted into the optical isomer of original compound by subjection to hydrolysis with acid or hydrolysis with hydrolysis.

Compound (I) may be crystalline.

Crystals of compound (I) can be produced by causing crystallization by subjecting compound (I) to itself well-known crystallization process.

Wherein as crystallization method, for example a method of crystallization from solution, a method of crystallization from vapor, a method of crystallization method from a melt, etc., may be proposed.

As said "method of crystallization from solution", a method is generally applied wherein using a factor relating to the solubility of the compound (solvent composition, pH, temperature, ionic strength, redox state, etc.) or the quantity of solvent, a transition from an unsaturated state to a super-saturated state is achieved; specific examples include, for example, a concentration method, slow-cooling method, reaction method (diffusion method, electrolysis method), hydrothermal cultivation method, fusing method, etc. As the solvent which is used, for example, an aromatic hydrocarbon (for example, benzene, toluene, xylene, etc.), halogenated hydrocarbon (for example, dichloromethane, chloroform, etc.), saturated hydrocarbon (for example, hexane, heptane, cyclohexane, etc.), ether (for example, diethyl ether, diisopropyl ether, tetrahydrofuran, dioxane, etc.), nitrile (for example, acetonitrile, etc.), ketone (for example, acetone, etc.), sulfoxide (for example, dimethyl sulfoxide, etc.), acid amide (for example N,N-dimethylformamide, etc.), ester (for example ethyl acetate, etc.), alcohol (for example methanol, ethanol, 2-propanol, etc.), water, etc. may be proposed. These solvents may be used singly or a mixture of two or more thereof in a suitable proportion (for example 1:1 to 1:100 (volume ratio)) may be used. Seed crystals can be used in accordance with requirements.

As said "method of crystallization from vapor", for example, a vaporization method (sealed tube method, gas flow method), gas phase reaction method, chemical transport method and the like methods may be proposed.

As said "method of crystallization from melt", for example, a normal freezing method (pull-up method, temperature gradient method, Bridgman method), zone melting method (zone leveling method, float zone method), special growth method (VLS method, liquid phase epitaxy method), etc. may be proposed.

As ideal example of crystallization method, a method wherein compound (I) is dissolved in a suitable solvent (alcohol, etc., such as methanol, ethanol, etc.) at a temperature of 20 to 120° C., and then the obtained solution is cooled to a temperature below the temperature when it dissolved (for example 0 to 50° C., preferably 0 to 20° C.), etc., may be proposed.

The crystals of the present invention obtained in this way can, for example, be isolated by filtration, etc.

A crystallographic analysis method based on powder X-ray diffraction is generally used as a method of analyzing the obtained crystals. Moreover, as a method of determining the crystal orientation, a mechanical method or optical method or the like method may be proposed.

The crystals of compound (I) obtained by said methods of production have high purity and high quality, have low hygroscopicity, and, their quality does not deteriorate even if stored for a long time under ambient conditions, and they have extremely excellent safety. Moreover, the biological properties (for example pharmacokinetics (absorptivity, distribution, metabolism, excretion), drug efficacy expression, etc.) are excellent; properties which are extremely useful in a drug.

Prodrugs of compound (I) are compounds which are converted to compound (I) by reactions due to gastric acid or enzymes or the like under physiological conditions; namely compounds transformed into compound (I) due to enzymatic oxidation, reduction, hydrolysis, etc., occurring, and compounds transformed into compound (I) due to hydrolysis caused by gastric acid, etc., occurring. Examples of prodrugs of compound (I) include compounds wherein an amino group of compound (I) has been acylated, alkylated or phosphorylated [for example, compounds wherein an amino group of compound (I) has been eicosanoylated, alanylated, pentylaminocarbonylated, (5-methyl-2-oxo-1,3-dioxolen-4-yl) methoxycarbonylated, tetrahydrofuranylated, pyrrolidyl methylated, pivaloyloxymethylated or tert-butylated]; compounds wherein a hydroxy group of compound (I) has been acylated, alkylated, phosphorylated or borylated [for example, compounds wherein a hydroxy group has been acetylated, palmitoylated, propanoylated, pivaloylated, succinylated, fumarylated, alanylated, dimethylaminomethylcarbonylated, etc.]; and compounds wherein a carboxyl group of compound (I) has been formed into an ester or amide [for example, compounds wherein a carboxyl group of compound (I) has been formed into an ethyl ester group, phenyl ester group, carboxymethyl ester group, dimethylaminomethyl ester group, pivaloyloxymethyl ester group, ethoxycarbonyloxyethyl ester group, phthalidyl ester group, (5-methyl-2-oxo-1,3-dioxolen-4-yl) methyl ester group, cyclohexyloxycarbonylethyl ester group, or methylamide group], and the like. These compounds can be produced from compound (I) by well-known processes.

Moreover, the prodrugs of compound (I) may be those that transform into compound (I) under physiological conditions in the same way as described in "Development of Pharmaceuticals" (Hirokawa Publishing, 1990) vol. 7, Molecular Design 163-198

In this specification, the compounds (I) and the prodrugs of compounds (I) may be collectively termed "the compounds of the present invention".

Compound (I) may be any of hydrate, non-hydrate, solvate and non-solvate.

Compounds which are isotopically labeled (for example, with $^3$H, $^{14}$C, $^{35}$S, $^{125}$I, etc.) are also included in compound (I).

Moreover, compounds substituted with heavy hydrogen in which $^1$H has been replaced by $^2$H (D) are also included within compound (I).

Tautomers are also included within compound (I).

Compound (I) may be present as a pharmacologically acceptable co-crystal or co-crystalline salt. Wherein, co-crystal and co-crystalline salt denotes a crystalline substance constructed from at least two unique solids at room temperature having various different physical characteristics (for example, structure, melting point, heat of fusion, hygroscopicity, solubility and stability, etc.). Co-crystals and co-crystalline salts can be produced in accordance with well-known crystallization methods.

Compound (I) may be used as PET tracer.

The compounds of the present invention have excellent TLR4 signaling inhibitory action, and so said compounds are useful as safe drugs based on the said action.

Accordingly, the TLR4 signaling inhibiting substances in the present invention can be used with respect to mammalian organisms (for example, mouse, rat, hamster, rabbit, cat, dog, cow, sheep, monkey, human, or the like) as preventive and/or therapeutic agents of, for example, autoimmune disease and/or inflammatory disease, and diseases such as infectious disease, cardiac disease, central nervous system disease, hypoimmunity and the like; for example, sepsis including serious sepsis, septic shock, septicemia, endotoxic shock, exotoxic shock, systemic inflammatory response syndrome (SIRS), compensatory antiinflammatory reaction syndrome (CARS), burn injury, trauma, postoperative complication, cardiac failure, shock, hypotension, rheumatoid arthritis, osteoarthritis, gastritis, ulcerative colitis, peptic ulcer, stress-induced peptic ulcer, Crohn's disease, autoimmune disease, graft rejection after organ transplantation, ischemia-reperfusion injury (IRI), liver injury (acute liver injury (ALI), ACLF), acute coronary microvascular embolism, shock-induced vascular embolism (disseminated intravascular coagulation (DIC) or the like), ischemic encephalopathy, arteriosclerosis, pernicious anemia, Fanconi anemia, sickle cell anemia, pancreatitis, nephrotic syndrome, acute and chronic nephropathy, nephritis, renal failure, insulin dependent diabetes mellitus, non-insulin dependent diabetes mellitus, hepatic porphyria, alcohol poisoning, Parkinson's disease, chronic leukemia, acute leukemia, tumor, myeloma, infant and adult respiratory distress syndrome, chronic obstructive pulmonary disease, dementia, Alzheimer's disease, multiple sclerosis, optic nerve myelitis, Vitamin E deficiency, ageing, sunburn, muscular dystrophy, myocarditis, cardiomyopathy, myocardial infarction, myocardial infarction sequellae, osteoporosis, pneumonia, hepatitis, psoriasis, pain, cataract, influenza infection, malaria, human immunodeficiency virus (HIV) infection, radiation damage, burn, hypercalcemia, ankylosing spondylitis, osteopenia, Paget's disease, osteomalacia, bone fracture, acute bacterial meningitis, *Helicobacter pylori* infection, invasive *Staphylococcus* infection, tuberculosis, systemic fungal infection, herpes simplex viral infection, varicella-zoster viral infection, human papilloma virus infection, acute viral encephalitis, encephalitis, meningitis, hypoimmunity accompanying infection, bronchial asthma, atopic dermatitis, allergic rhinitis, reflux esophagitis, fever, hypercholesterolemia, hyperglyceridemia, hyperlipidemia, diabetic complications, diabetic nephropathy, diabetic neuropathy, diabetic retinopathy, gout, gastric atony, hemorrhoids, systemic lupus erythematosus, spinal cord injury, insomnia, schizophrenia, epilepsy, cirrhosis, hepatic insufficiency, unstable angina, cardiac valvular disease, thrombocytopenia or hypotension due to dialysis, acute ischemic cerebral apoplexy, acute cerebral thrombosis, cancer metastasis, urinary bladder cancer, breast cancer, uterine cervical cancer, colorectal cancer, gastric cancer, ovarian cancer, prostate cancer, small cell lung cancer, non-small cell lung cancer, malignant melanoma, Hodgkin's disease, non-Hodgkin's lymphoma, side effects due to anticancer agent and immunosuppressant drug administration, chronic obstructive pulmonary disease, cystic fibrosis, pulmonary fibrosis, autoimmune hemolytic anemia, meningitis, inflammatory pulmonary disease (for example, silicosis, pulmonary sarcoidosis, tuberculosis), endometriosis, cachexia (for example, cachexia due to infection, cancerous cachexia, cachexia due to acquired immunodeficiency syndrome), cancer pain, Addison's disease, acute pain due to inflammation, pain due to chronic inflammation, post-operative pain (incision wound pain, deep pain, visceral pain, chronic post-operative pain, or the like), myalgia (myalgia accompanying chronic pain, stiff neck, or the like), arthralgia, toothache, temporomandibular arthralgia, headache (migraine headache, tension headache, headache accompanying pyrexia, headache accompanying hypertension), visceral pain (cardialgia, anginal pain, abdominal pain, kidney pain, urinary tract pain, bladder pain), pain of the obstetric and gynecological area (intermenstrual pain, dysmenorrheal and labour pain), neurogenic pain (spinal disc herniation, nerve root pain, post-herpes zoster neuralgia, trigeminal neuralgia, lumbago, or the like), chemotherapys ((taxane anticancer drugs (for example, paclitaxel (taxol), docetaxel), vinca alkaloid anticancer drugs (for example, vincristine, vinblastine), platinum preparations (for example, cisplatin, carboplatin, oxaliplatin), molecular target drug (for example, bortezomib) or the like))-induced peripheral neuropathy (CIPN) and associated neurological symptoms (chemotherapy-induced neuropathic pain (CINP) (dysesthesia such as numbness and/or pain (for example, muscle pain, nerve pain))), reflex sympathetic atrophy, complex local pain syndrome, pituitary gland abscess, thyroiditis, peritonitis, erythema nodosum), allergic conjunctivitis, pollinosis, metal allergy, exudative otitis media, Meniere's disease, contact dermatitis, anaphylaxis, urticaria, myasthenia gravis, Sjogren's syndrome, Basedow's disease, leukocyte abnormality, renal tubulointerstitial disorder (including fibrillary pathology), acute coronary artery syndrome, atherosclerotic aortic aneurysm, cardiac anaphylaxis, deep vein thrombosis, ophthalmologic diseases (for example, pterygium, spring catarrh, dry eye, or the like), food allergy, NUD (Non Ulcer Dyspepsia), gastric MALT lymphoma, ulcer due to non-steroid anti-inflammatory drug, gastric hyperacidity, gastric hyperacidity and ulcer due to postoperative stress, obesity, edema, granuloma, atopic myelitis, neurofibroma, nasal mucosal hypersensitivity, osteoarthritis, scleroderma, or the like. Moreover, the TLR4 signaling inhibiting substance of the present invention can also be used for increasing efficiency of in vitro fertilization.

Wherein, the "prevention" of said disease means, for example, the administration of a drug containing the compound of the present invention to a patient who has not yet developed the said disease but is thought to be of high risk of onset due to some factor related to the said disease, or to a patient who has developed the disease but without subjective symptoms, or the administration of a drug containing the compound of the present invention to a patient who, following treatment of the said disease, is concerned about recurrence of said disease.

A drug containing the compound of the present invention can be used as a compound of the present invention alone or as pharmaceutical composition of a mixture of a compound of the present invention and pharmacologically acceptable carrier, in accordance with well-known processes for the production of drug preparations (for examples, processes in accordance with Pharmacopeia of Japan). Pharmaceutical compositions containing the compound of the present invention can be safely administered orally or parenterally (example, intravenously, intramuscularly, subcutaneously, by intraorgan administration, intranasally, intracutaneously, by eye drops, intracerebrally, endorectally, intravaginally, intraperitoneally, by intratumor administration, by tumor proximal administration, by administration at the focus of the disease, or the like); for example as a tablet (including sugar coated tablet, film coated tablet, sublingual tablet, oral cavity disintegration tablet, buccal tablet), pill, powder, granules, encapsulated formulation (including soft capsule agent and microcapsule agent), troche agent, syrup, liquid agent (including organ preservation solution and organ perfusion solution), emulsion, suspending agent, controlled release preparation (for example, rapid release preparation, slow release preparation, controlled-release microcapsule agent), aerosol, film agent (for example, oral cavity disintegration film, oral mucosal patch), injectable (for example, subcutaneous injection agent, intravenous injection agent, intramuscular injection agent, intraperitoneal injection agent), drip infusion agent, percutaneous absorption preparation, cream agent, ointment, lotion, patch, suppository (for example, anal suppository, vaginal suppository), pellet, transnasal agent, transpulmonary agent (inhalant), instillation, or the like.

The content of the compound of the present invention in the drug of the present invention is about 0.01 wt. % to about 100 wt. % of the total drug. Said dose differs depending on the administration subject, administration route, disease, or the like, however, for example, with respect to a patient with chemotherapy-induced peripheral neuropathy (CIPN), chemotherapy-induced neuropathic pain (CINP), liver injury and/or ischemia-reperfusion injury (IRI) (about 60 kg in weight), as orally administered agent, about 0.01 mg/kg body weight to about 500 mg/kg body weight, preferably about 0.1 mg/kg body weight to about 50 mg/kg body weight, more preferably about 1 mg/kg body weight to about 30 mg/kg body weight as effective ingredient (compound (I)) per day, may be administered once a day or divided into several times.

As the pharmacologically acceptable carrier which may be used in the production of the drug of the present invention, various conventionally used organic or inorganic carrier substances may be proposed, and for example, excipients, lubricants, binding agents and disintegrating agents in solid preparations; and, solvents, solubilizers, suspending agents, isotonizing agents, buffer agents and analgesics and the like in liquid preparations may be proposed. Furthermore, additives such as conventional preservatives, antioxidant, colorant, sweetener, adsorbent, wetting agent, or the like can be suitably used in a suitable quantity in accordance with requirements.

The dose when the pharmaceutical composition of the present invention is a slow release preparation varies in various ways depending on the kind and content of compound (I), agent form, duration of drug release, administration subject animal (mammalian organism such as mouse, rat, hamster, guinea pig, rabbit, cat, dog, cow, horse, pig, sheep, monkey, human or the like) and object of administration, however, for example, when applied by a parenteral administration route, the administration preparation may be designed so that about 0.1 to about 100 mg of compound (I) is released in a week.

Examples of excipient include lactose, sucrose, D-mannitol, starch, corn starch, crystalline cellulose, light anhydrous silicic acid, etc.

Examples of lubricant include magnesium stearate, calcium stearate, talc, colloidal silica, etc.

Examples of binding agent include crystalline cellulose, sucrose, D-mannitol, dextrin, hydroxypropylcellulose, hydroxypropyl methyl cellulose, polyvinylpyrrolidone, starch, sucrose, gelatin, methyl cellulose, carboxymethylcellulose sodium, etc.

Examples of disintegrating agent include starch, carboxymethylcellulose, carboxymethylcellulose calcium, carboxymethyl starch sodium, L-hydroxypropylcellulose, etc.

Examples of solvent include water used for injection, alcohol, propylene glycol, macrogol, sesame oil, corn oil, olive oil, etc.

Examples of solubilizer include polyethyleneglycol, propylene glycol, D-mannitol, benzyl benzoate, ethanol, tris aminomethane, cholesterol, triethanolamine, sodium carbonate, sodium citrate, etc.

Examples of suspending agent include surfactants such as stearyl triethanolamine, sodium lauryl sulfate, laurylamino propionic acid, lecithin, benzalkonium chloride, benzethonium chloride, glyceryl monostearate, etc., hydrophilic macromolecules such as polyvinyl alcohol, polyvinylpyrrolidone, carboxymethylcellulose sodium, methyl cellulose, hydroxymethyl cellulose, hydroxyethyl cellulose, hydroxypropylcellulose, etc., and the like.

Examples of isotonizing agent include glucose, D-sorbitol, sodium chloride, glycerol, D-mannitol, etc.

Examples of buffer agent include buffers such as phosphates, acetates, carbonates, citrates, etc.

Examples of analgesic include benzyl alcohol, etc.

Examples of preservative include parahydroxybenzoic acid esters, chlorobutanol, benzyl alcohol, phenylethyl alcohol, dehydroacetic acid, sorbic acid, etc.

Examples of anti-oxidant include sulfite, ascorbic acid, α-tocopherol, etc.

During the prevention and/or treatment of various diseases, the compounds of the present invention can be used together with other agents. Hereinafter, drugs which are used when the compounds of the present invention are used concomitantly with other drugs will be referred to as "combined used agents of the present invention".

The TLR4 signaling inhibiting substance can be co-used concomitantly with other drugs. Examples of such co-used drugs include antibacterial agents, antifungal agents, nonsteroidal antiinflammatory drugs, steroid drugs, anticoagulants, antiplatelet drugs, thrombolytic drugs, immunomodulators, antiprotozoal drugs, antitussive-expectorant drugs, sedatives, anesthetic drugs, narcotic antagonists, antiulcer drugs, drugs for treating hyperlipidemia, drugs for treating arteriosclerosis, HDL elevating drugs, unstable plaque stabilization drugs, myocardial protective agents, drugs for treating hypothyroidism, drugs for treating nephrotic syndrome, drugs for treating chronic renal failure, diuretics, antihypertensive drugs, drugs for treating cardiac failure, muscle relaxants, antiepileptic drugs, cardiotonics, vasodilators, vasoconstrictors, drugs for treating arrhythmia, drugs for treating diabetic mellitus, vasopressor, tranquilizer, antipsychotic, drugs for treating Alzheimer's disease, antiparkinsonian agents, drugs for treating amyotrophic lateral sclerosis, nerve nutritional factors, antidepressants, drugs for treating schizophrenia, anticancer drugs, Vitamin drugs, Vitamin derivatives, drugs for treating arthritis, antirheumatics, antiallergic drugs, antiasthmatic drugs, drugs for treating atopic dermatitis, drugs for treating allergic rhinitis, drugs for treating pollakiuria/involuntary micturition, proteolytic drugs, protease inhibitors, anti SIDS drugs, antisepsis drugs, anti septic shock drugs, endotoxin antagonists or antibodies, signal transduction inhibitors, inflammatory mediator action inhibitors, inflammatory mediator action inhibiting antibodies, inflammatory mediator production inhibitors, antiinflammatory mediator action depressant, antiinflammatory mediator action inhibiting antibody, anti-inflammatory mediator production inhibitor, al adrenergic agents, antiemetics, agents for preventing elevated methemoglobin, etc. Among these, anticancer drugs, antibacterial agents, antifungal agents, nonsteroidal antiinflammatory drugs, steroid drugs, anticoagulants, antiemetics, agents for preventing elevated methemoglobin, etc. are preferred. The following comprise specific examples.

(1) Antibacterial Agents (i) Sulfa drugs

Sulfamethizole, sulfisoxazole, sulfamonomethoxine, sulfamethizole, salazosulfapyridine, silver sulfadiazine, etc.

(ii) Quinoline antibacterial agents

Nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin, etc.

(iii) Antitubercular agent

Isoniazid, ethambutol (ethambutol hydrochloride), p-aminosalicylate (calcium p-aminosalicylate), pyrazinamide, ethionamide, protionamide, rifampicin, streptomycin sulphate, kanamycin sulfate, cycloserine, etc.

(iv) Acid fast bacterium drugs

Diaminodiphenylsulfone, rifampicillin, etc.

(v) Antiviral agents

Idoxuridine, acyclovir, vidarabine, ganciclovir, etc.

(vi) Anti HIV drugs

Zidovudine, didanosine, zalcitabine, indinavir sulfate ethanolate, ritonavir, etc.

(vii) Anti-spirochetal drugs (viii) Antibiotics

Tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or salts thereof, griseofulvin, Lankacidin species (J. Antibiotics, 38, 877-885 (1985) and the like.

(2) Antifungal Drugs (i) polyene antibiotics (for example, amphotericin B, nystatin, trichomycin)

(ii) griseofulvin, pyrrolnitrin, etc.

(iii) cytosine metabolism antagonists (for example, flucytosine)

(iv) Imidazole derivatives (for example, econazole, clotrimazole, miconazole nitrate, bifonazole, croconazole)

(v) triazole derivatives (for example, fluconazole, itraconazole, azole compounds (2-((1R,2R)-2-(2, 4-difluorophenyl)-2-hydroxy-1-methyl-3-(1H-1,2,4-triazol-1-yl) propyl)-4-(4-(2,2,3,3-tetrafluoropropoxy)phenyl)-3(2H,4H)-1,2,4-triazolone)

(vi) thiocarbamic acid derivatives (for example, tolnaftate)

(vii) Echinocandin derivatives (for example caspofungin, micafungin, anidulafungin).

(3) Nonsteroidal Antiinflammatory Drugs

Acetaminophen, phenacetin, ethenzamide, sulpyrine, antipyrine, Migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizole, tiaramide hydrochloride, zaltoprofen, gabexate mesilate, camostat mesilate, ulinastatin, colchicine, probenecid, sulfinpyrazone, benzbromarone, allopurinol, sodium aurothiomalate, sodium hyaluronate, sodium salicylate, morphine hydrochloride, salicylic acid, atropine, scopolamine, morphine, pethidine, levorphanol, ketoprofen, naproxen, oxymorphone, meloxicam, celecoxib, rofecoxib and salts thereof, etc.

(4) Steroid Drugs

Dexamethasone, hexestrol, methimazole, betamethasone, triamcinolone, triamcinolone acetonide, fluocinonide, fluocinolone acetonide, prednisolone, methylprednisolone, cortisone acetate, hydrocortisone, fluorometholone, beclomethasone propionate, estriol, etc.

(5) Anticoagulants

Heparin sodium, sodium citrate, activated protein C, tissue factor pathway inhibitors, antithrombin III, dalteparin sodium, warfarin potassium, argatroban, gabexate, sodium citrate, etc.

(6) Antiplatelet Drugs

Ozagrel sodium, ethyl icosapentate, beraprost sodium, alprostadil, ticlopidine hydrochloride, pentoxifylline, dipyridamole, etc.

(7) Thrombolytic Drugs

Tisokinase, urokinase, streptokinase, etc.

(8) Immunomodulators

Cyclosporine, tacrolimus, gusperimus, azathioprine, anti-lymphocyte serum, dried sulfonated immunoglobulin, erythropoietin, colony stimulating factor, interleukin, interferon, etc.

(9) Antiprotozoal Drugs

Metronidazole, tinidazole, diethylcarbamazine citrate, quinine hydrochloride, quinine sulfate, etc.

(10) Antitussive-Expectorant Drugs

Ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlorphedianol, picoperidamine, cloperastine, protokylol, isoproterenol, salbutamol, terbutalin, oxymetebanol, morphine hydrochloride, dextropethorphan hydrobromide, oxycodone hydrochloride, phosphoric acid dimorphan, tipepidine hibenzate, pentoxyverine citrate, clofedanol hydrochloride, benzonatate, guaifenesin, bromhexine hydrochloride, ambroxol hydrochloride, acetylcysteine, cysteine ethyl ester hydrochloride, carbocisteine, etc.

(11) Sedatives

Chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromvalerylurea, chloral hydrate, triclofos sodium, etc.

(12) Anesthetic Drugs (12-1) Local Anesthetics

Cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethylaminobenzoic acid, oxethazaine and the like.

(12-2) General Anesthetics (i) Inhalation anesthetics (for example, ether, halothane, nitrous oxide, influran, enflurane)

(ii) Intravenous anesthetics (for example, ketamine hydrochloride, droperidol, thiopental sodium, thiamylal sodium, pentobarbital) and the like.

(13) Narcotic Antagonists

Levallorphan, nalorphine, naloxone and salts thereof, etc.

(14) Antiulcer Drugs

Metoclopromide, histidine hydrochloride, lansoprazole, metoclopramide, pirenzepine, cimetidine, ranitidine, famotidine, urogastrin, oxethazaine, proglumide, omeprazole, sucralfate, sulpiride, cetraxate, gefarnate, aldioxa, teprenone, prostaglandin, etc.

(15) Drugs for Treating Hyperlipidemia

HMG-Co Reductase inhibitors (for example, fluvastatin, cerivastatin, atorvastatin, etc.), fibrate system agents (for example, simfibrate, aluminum clofibrate, clinofibrate, fenofibrate, etc.), bile acid adsorbents (for example, cholestyramine, etc.), nicotinic acid preparation (for example, nicomol, niceritrol, tocopherol nicotinate, etc.), probucol and derivatives thereof, polyunsaturated fatty acid derivative (for example, ethyl icosapentate, polyene phosphatidylcholine, melinamide, etc.), plant sterols (for example, γoryzanol, soy sterol, etc.), elastase, dextran sulfate sodium, squalene synthase inhibitors, squalene epoxidase inhibitors, CETP inhibitors, 2-chloro-3-(4-(2-methyl-2-phenyl propoxy) phenyl) propionic acid ethyl ester (Chem, Pharm. Bull), 38, 2792-2796 (1990), LDL receptor enhancer, cholesterol absorption inhibitors (Ezetimibe, etc.), MTP inhibitors, ileal bile acid transporter inhibitors, SCAP ligand, FXR ligands, etc.

(16) Drugs for Treating Arteriosclerosis

MMP inhibitors, chymase inhibitors, ACAT inhibitors (Avasimibe, Eflucimibe, etc.), apoAI Milano and analogue thereof, scavenger receptor inhibitors, 15-lipoxygenase inhibitors, phospholipase A2 inhibitors, ABCA1 activator, LXR ligand, sphingomyelinase inhibitors, paraoxonase activator, estrogen receptor agonists, etc.

(17) HDL-Elevating Drugs

Squalene synthase inhibitors, CETP inhibitors, LPL activators, etc.

(18) Unstable Plaque Stabilizing Drugs

MMP inhibitors, chymase inhibitors, ACAT inhibitors, lipid rich plaque retraction agents, etc.

(19) Myocardial Protective Agents

Oral agents for cardiac ATP-K, endothelin antagonists, urotensin antagonists, etc.

(20) Drugs for Treating Hypothyroidism

Desicated thyroid (Chireoido), sodium levothyroxine (Thyradin-S), liothyronine sodium (thyronine, thyromine) and the like.

(21) Drugs for Treating Nephrotic Syndrome

Prednisolone (predonine), prednisolone sodium succinate (predonine), methylprednisolone sodium succinate (Solu-Medrol), betamethasone (Rinderon), and the like.

(22) Agents for Treating Chronic Renal Failure

Diuretics (for example, furosemide (Lasix), bumetanide (Lunetoron), azosemide (Diart)). Antihypertensive agents (for example, ACE inhibitors, enalapril maleate (Renivace), calcium antagonists (manidipine), a receptor blockers, AII antagonists (Candesartan)) and the like.

(23) Diuretics

Thiazide derivative diuretics (benzylhydrochlorothiazide, cyclopenthiazide, ethiazide, hydrochlorothiazide, hydroflumethiazide, methylclothiazide, penfluthiazide, polythiazide, trichlormethiazide, etc.), loop diuretics (chlorthalidone, clofenamide, indapamide, mefruside, meticrane, sotolazone, tripamide, quinethazone, metolazone, furosemide, etc.), potassium sparing diuretics (spironolactone, triamterene, etc.).

(24) Antihypertensive Drugs (i) Sympatholytic agents

α2 agonist (for example, clonidine, guanabenz, guanfacine, methyldopa, etc.), gangliolytic (for example, hexamethonium, trimethaphan, etc.), presynaptic blockers (for example, alseroxylon, dimethylamino reserpinate, rescinnamine, reserpine, syrosingopine, etc.), neuron blockers (for example, betanidine, guanethidine, etc.), al blockers (for example, bunazosin, doxazosin, prazosin, terazosin, urapidil, etc.), β blockers (for example, propranolol, nadolol, timolol, nipradilol, bunitrolol, indenolol, penbutolol, carteolol, carvedilol, pindolol, acebutolol, atenolol, bisoprolol, metoprolol, labetalol, amosulalol, arotinolol, etc.) and the like.

(ii) Vasodilators

Calcium channel antagonists (for example, manidipine, nicardipine, nilvadipine, nisoldipine, nitrendipine, benidipine, amlodipine, aranidipine, etc.), phthalazines (for example, budralazine, cadralazine, ecarazine, hydralazine, todralazine, etc.) and the like.

(iii) ACE inhibitors

Alacepril, captopril, cilazapril, delapril, enalapril, lisinopril, temocapril, trandolapril, quinapril, imidapril, benazepril, perindopril, etc.

(iv) All antagonists

Losartan, Candesartan, valsartan, Telmisartan, Irbesartan, forasartan, etc.

(v) Diuretics (for example, said diuretics, etc.).

(25) Drugs for Treating Cardiac Failure

Cardiotonics (for example, digitoxin, digoxin, methyldigoxin, lanatoside C, proscillaridin, etc.), α, β agonists (for example, epinephrine, norepinephrine, isoproterenol, dopamine, docarpamine, dobutamine, denopamine, etc.), phosphodiesterase inhibitors (for example, amrinone, milrinone, olprinone hydrochloride, etc.) calcium channel sensitizers (for example, pimobendan, etc.), nitrovasodilators (for example, nitroglycerin, isosorbide dinitrate, etc.), ACE inhibitors (for example, said ACE inhibitor, etc.), diuretics (for example, said diuretic, etc.), carperitide, ubidecarenone, vesnarinone, aminophylline, etc.

(26) Muscle Relaxants

Pridinol, tubocurarine, pancuronium, tolperisone hydrochloride, chlorphenesin carbamate, baclofen, chlormezanone, mephenesin, chlorzoxazone, eperisone, tizanidine, etc.

(27) Antiepileptic Drugs

Phenytoin, ethosuximide, acetazolamide, chlordiazepoxide, trimethadione, carbamazepine, phenobarbital, primidone, sultiame, sodium valproate, clonazepam, diazepam, nitrazepam, etc.

(28) Cardiotonics aminophylline, etilefrine, dopamine, dobutamine, denopamine, aminophylline, amrinone, pimobendane, ubidecarenone, digitoxin, digoxin, methyldigoxin, lanatoside C, G-strophanthin, etc.

(29) Vasodilators

Oxyfedrine, diltiazem, tolazoline, hexobendine, bamethan, clonidine, methyldopa, guanabenz, etc.

(30) Vasoconstrictors

Dopamine, dobutamine denopamine, etc.

(31) Drugs for Treating Arrhythmia (i) Sodium channel blockers (for example, quinidine, procainamide, disopyramide, ajmaline, cibenzoline, lidocaine, diphenylhydantoin, mexiletine, propafenone, flecainide, pilsicainide, phenytoin, etc.)

(ii) β blockers (for example, propranolol, alprenolol, bufetolol, oxprenolol, atenolol, acebutolol, metoprolol, bisoprolol, pindolol, carteolol, arotinolol, etc.)

(iii) Potassium channel blockers (for example, amiodarone, etc.)

(iv) Calcium channel blockers (for example, verapamil, diltiazem, etc.), and the like.

(32) Vasopressors

Dopamine, dobutamine, denopamine, digitoxin, digoxin, methyldigoxin, lanatoside C, G-strophanthin, etc.

(33) Drugs for Treating Diabetic Mellitus

Sulfonylurea agents (for example, tolbutamide, chlorpropamide, glyclopyramide, acetohexamide, tolazamide, glibenclamide, glybuzole, etc.), biguanide agents (for example, metformin hydrochloride, bulformin hydrochloride, etc.), α-glucosidase inhibitors (for example, Voglibose, acarbose, etc.), insulin sensitizers (for example, pioglitazone, roziglitazone, troglitazone, etc.), insulin, glucagon, agents for treating diabetes complications (for example, epalrestat, etc.), DPP4 inhibitors (for example, sitagliptin, vildagliptin, Alogliptin, linagliptin, etc.) and the like.

(34) Tranquilizers

Diazepam, lorazepam, oxazepam, chlordiazepoxide, medazepam, oxazolam, cloxazolam, clotiazepam, bromazepam, etizolam, fludiazepam, hydroxyzine, etc.

(35) Antipsychotics

Chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine, etc.

(36) Drug for Treating Alzheimer's Diseases (i) Cholinesterase inhibitors such as donepezil, rivastigmine, galantamine, etc.

(ii) Cerebral function activators, etc. such as idebenone, memantine, vinpocetine, etc.

(37) Antiparkinsonian Agents

L-DOPA, deprenyl, carbidopa+levodopa, pergolide, ropinirole, cabergoline, pramipexole, entacapone, lazabemide, etc.

(38) Drugs for Treating Amyotrophic Lateral Sclerosis

Riluzole, mecasermin, gabapentin, etc.

(39) Antidepressants

Imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride, etc.

(40) Drugs for Treating Schizophrenia

Olanzapine, risperidone, quetiapine, iloperidone, etc.

(41) Anticancer Drugs

6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, Picibanil, lentinan, levamisole, bestatin, azimexon, glycyrrhizin, doxorubicin hydrochloride, aclarubicin hydrochloride, bleomycin hydrochloride, peplomycin sulphate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyl testosterone, testosterone propionate, testosterone enanthate, mepitiostane, fosfestrol, chlormadinone acetate, leuprorelin acetate, buserelin acetate, paclitaxel, docetaxel, oxaliplatin, vincristine, vinblastine, cisplatin, carboplatin, bortezomib, etc.

(42) Vitamin Drugs
(i) Vitamin A types: Vitamin $A_1$, Vitamin $A_2$ and retinol palmitate
(ii) Vitamin D types: Vitamin $D_1$, $D_2$, $D_3$, $D_4$ and $D_5$
(iii) Vitamin E types: α-tocopherol, β-tocopherol, γ-tocopherol, δ-tocopherol, nicotinic acid dl-α-tocopherols
(iv) Vitamin K types: Vitamin $K_1$, $K_2$, $K_3$ and $K_4$
(v) Folic acid (Vitamin M)
(vi) Vitamin B types: Vitamin $B_1$, Vitamin $B_2$, Vitamin $B_3$, Vitamin $B_5$, Vitamin $B_6$ and Vitamin $B_{12}$
(vii) Biotin (Vitamin H), etc.

(43) Vitamin Derivatives
Various vitamin derivatives such as, for example, ascorbic acid, Vitamin D3 derivatives such as 5, 6-trans-cholecalciferol, 2, 5-hydroxycholecalciferol and 1-α-hydroxycholecalciferol, etc., Vitamin $D_2$ derivatives such as 5, 6-trans-ergocalciferol, etc., etc.

(44) Antiallergic Drugs
Diphenhydramine, chlorpheniramine, tripelennamine, clemizole, diphenylpyraline, methoxyphenamine, disodium cromoglycate, tranilast, repirinast, amlexanox, ibudilast, ketotifen, terfenadine, mequitazine, azelastine, epinastine, ozagrel hydrochloride, Pranlukast hydrate, seratrodast, etc.

(45) Antiasthmatic Drugs
Isoprenaline hydrochloride, salbutamol sulphate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, disodium cromoglycate, tranilast, repirinast, ibudilast, ketotifen, terfenadine, mequitazine, azelastine, epinastine, ozagrel hydrochloride, Pranlukast hydrate, seratrodast, dexamethasone, prednisolone, hydrocortisone, beclomethasone proprionate, etc.

(46) Drugs for Treating Atopic Dermatitis
Disodium cromoglycate, etc.

(47) Drugs for treating allergic rhinitis
Disodium cromoglycate, chlorpheniramine maleate, alimemazine tartrate, clemastine fumarate, homochlorcyclizine hydrochloride, terfenadine, mequitazine, etc.

(48) Drugs for Treating Pollakiuria/Involuntary Micturition
Flavoxate hydrochloride, etc.

(49) Antisepsis Drugs
Peptide compounds such rBPI-21 (bactericidal permeability increasing protein), BI-51017 (antithrombin III), SC-59735 (rTFPI), r-PAF acetylhydrolase, LY-203638 (r-activated protein C), anti TNF-α antibody, anti CD14 antibody, CytoFab, alkaline phosphatase (LPS inactivator), etc., non-peptide compounds such as JTE-607, eritoran, S-5920, FR-167653, ONO-1714, ONO-5046 (sivelestat), GW-273629, RWJ-67657, GR-270773, NOX-100, GR-270773, NOX-100, INO-1001, etc. and the like.

(50) Drugs for Improving Prognosis after Coronary Artery Bypass Surgery Eritoran, etc.

(51) Antiemetics
Phenothiazine derivatives, 5-HT3 receptor antagonists, etc.

(52) Agents for Preventing Elevated Methemoglobin
Methylene blue, ascorbic acid, etc.

(53) Anticytokine Agents
(I) Protein Preparations
(i) TNF inhibitors
Etanercept, Infliximab, adalimubab, certolizumab pegol, golimumab, PASSTNF-α, soluble TNF-α receptor, TNF-α binding protein, anti TNF-α antibody, etc.

(ii) Interleukin-1 inhibitors
Anakinra (interleukin-1 receptor antagonists), soluble interleukin-1 receptor, etc.
(iii) Interleukin-6 inhibitors
Tocilizumab (anti interleukin-6 receptor antibody), anti interleukin-6 antibody, etc.
(iv) Interleukin-10 drugs
Interleukin-10, etc.
(v) Interleukin-12/23 inhibitors
Ustekinumab, briakinumab (anti interleukin-12/23 antibody), etc.
(vi) interleukin-17 inhibitors
Secukinumab, ixekizumab, brodalumab, etc.
(II) Non-Protein Preparations
(i) MAPK inhibitors
BMS-582949, etc.
(ii) Gene control drugs
Inhibitors of molecules related to signal transductions such as NF-κ, NF-κB, IKK-1, IKK-2, AP-1, etc.
(iii) Cytokine production inhibitors
Iguratimod, tetomilast, etc.
(iv) TNF-α converting enzyme inhibitors
(v) Interleukin-1β converting enzyme inhibitors
VX-765, etc.
(vi) Interleukin-6 antagonists
HMPL-004, etc.
(vii) Interleukin-8 inhibitors
IL-8 antagonists, CXCR1 & CXCR2 antagonists, cefalexin, etc.
(viii) chemokine antagonists
CCR9 antagonists (CCX-282, CCX-025), MCP-1 antagonists, etc.
(ix) Interleukin-2 receptor antagonists
Denileukin, diftitox, etc.
(x) Therapeutic vaccines
TNF-α vaccine, etc.
(xi) Gene therapy drugs
Gene therapy drugs having the object of elevating expression of genes having antiinflammatory effect such as interleukin-4, interleukin-10, soluble interleukin-1 receptor, soluble TNF-α receptor, etc.
(xii) Antisense compounds
ISIS-104838, etc.
(54) Integrin Inhibitors
Natalizumab, vedolizumab, AJM300, TRK-170, E-6007, etc.
Antidepressant drugs (for example, amitriptyline, imipramine, clomipramine, desipramine, doxepin, nortriptyline, duloxetine, milnacipran, fluoxetine, paroxetine, sertraline, citalopram, etc.)
Anticonvulsants drugs (for example, carbamazepine, pregabalin, gabapentin, lamotrigine, phenytoin, valproic acid, etc.)
Narcotics (for example, morphine, oxycodone, fentanyl, methadone, codeine, tramadol, etc.).
(55) Others
Hydroxycam, diacerein, megestrol acetate, nicergoline, prostaglandins, etc.

During combined use, the times of administration of the compound of the present invention and the co-used drug are not restricted, and compounds of the present invention and co-used drug may be administered at the same or different times with respect to an administration subject. If the dose of the co-used drug is in accordance with the dose used clinically, then the co-used dose can be suitably selected depending on the administration subject, administration route, disease and combination.

The form of the administration of the combination is not restricted in particular, and the compound of the present invention and co-used drug may be combined during administration. As such form of administration, for example, (1) administration of single pharmaceutical preparation obtained by formulating the compound of the present invention and a co-used drug at the same time, (2) administration at the same time and by the same administration route of two kinds of pharmaceutical preparations in which the compound of the present invention and the co-used drug are separately formulated, (3) administration at different times but by the same administration route of two kinds of pharmaceutical preparations in which the compound of the present invention and the co-used drug are separately formulated, (4) administration at the same time but by different administration routes of two kinds of pharmaceutical preparations in which the compound of the present invention and the co-used drug are separately formulated, and (5) administration at different times and by different administration routes of two kinds of pharmaceutical preparations in which the compound of the present invention and the co-used drug are separately formulated, (for example, administration of co-used drug after having administered the compound of the present invention or administration in the reverse order to this), may be proposed.

The compounding ratio of the compound of the present invention and co-used drug in the combined use agent of the present invention can be suitably selected depending on the administration subject, the administration route, the disease, etc.

For example, the content of the compound of the present invention in the combined use agent of the present invention, differs depending on the form of the preparation, however, said content is usually about 0.01 to 100 wt. %, preferably about 0.1 to 50 wt. %, and more preferably about 0.5 to 20 wt. % with respect to the whole pharmaceutical preparation.

The content of co-used drug in the combined use agent of the present invention, differs depending on the form of the preparation, however, said content is usually about 0.01 to 100 wt. %, preferably about 0.1 to 50 wt. %, and more preferably about 0.5 to 20 wt. % with respect to the whole pharmaceutical preparation.

The content of additive such as carrier, etc. in the combined use agent of the present invention, differs depending on the form of the preparation, however said content is usually about 1 to 99.99 wt. %, preferably about 10 to 90 wt. % with respect to the whole pharmaceutical preparation.

Moreover, the compound of the present invention and co-used drug may be contained in similar contents when each are respectively formulated pharmaceutically separately.

The dose differs depending on the type of the compound of the present invention, the administration route, the symptoms and the age of patient, etc., and, for example, when compound (I) is orally administered to a patient (about 60 kg in weight) with chemotherapy-induced peripheral neuropathy (CIPN), chemotherapy-induced neuropathic pain (CINP), liver injury and/or ischemia-reperfusion injury (IRI), about 0.1 mg/kg body weight to about 30 mg/kg body weight, preferably about 1 mg/kg to 20 mg/kg in weight body weight are administered per day, either in one administrative dose or divided several times.

The dose when the drug of the present invention is a slow release preparation varies depending on the kind and the content of compound (I), the agent form, the duration of the drug release, the administered subject animal (for example, mammalian organism such as mouse, rat, hamster, guinea pig, rabbit, cat, dog, cow, horse, pig, sheep, monkey, human, etc.) and the purpose of the administration, but for example when applied by parenteral administration, about 0.1 to 100 mg of compound (I) should be released from the administered pharmaceutical preparation over a week.

The co-used drug can be established in an amount within a range with which adverse reactions are not a problem. The daily dose of the co-used drug varies depending on the severity of the symptoms, the age, gender, body weight and sensitivity of the administration subject, the duration of administration, the interval, the properties, compound and kind of drug preparation and the type of active ingredient; and is not limited in particular, however, usually the dose of drug by oral administration is about 0.001 to 2000 mg, preferably about 0.01 to 500 mg, more preferably about 0.1 to 100 mg per 1 kg body weight of mammalian organism; divided by 1 to 4 times per day.

When a co-used drug of the present invention is administered, the compound of the present invention and co-used drug may be administered over the same time periods, or may be administered over different time periods. When administered over different periods, the time difference varies depending on the administered active ingredient, formulation and administration method, however, for example, when the co-used drug is administered first, a method may be adopted wherein the compound of the present invention is administered within 1 minute to 3 days, preferably within 10 minutes to 1 day, more preferably still 15 minutes to 1 hour, after administration of the co-used drug. When the compound of the present invention is administered first, a method may be adopted wherein the co-used drug is administered within 1 minute to 1 day, preferably 10 minutes to 6 hours, more preferably 15 minutes to 1 hour, after the administration of the compound of the present invention.

EXAMPLES

The present invention will now be described in detail by reference to the following Examples, Test Examples and Preparation Examples, but the invention is in no way limited by these, and moreover changes may be made thereto within a range that do not deviate from the scope of the present invention.

In the following Examples, "room temperature" usually denotes about 10° C. to about 35° C. The ratios shown for mixed solvents denote the ratios by volume, unless otherwise stated in particular. % denotes wt. % unless otherwise stated in particular.

In HPLC (high performance liquid chromatography), a description of C18, denotes that octadecyl-bonded silica gel was used. The ratios for the eluting solvents denote the ratios by volume unless otherwise stated in particular.

The following abbreviations are used in the following Examples.
mp: Melting point
MS: Mass spectrum
[M+H]$^+$ (M−H)$^-$: Molecular ion peaks
M: Molar concentration
N: Normal
CDCl$_3$: Deuterated chloroform
DMSO-d$_6$: Deuterated dimethyl sulfoxide
$^1$H NMR: Proton nuclear magnetic resonance
LC/MS: Liquid chromatograph mass spectrometer
ESI: Electrospray Ionization
APCI: Atmospheric Pressure Chemical Ionization
SFC: Supercritical fluid chromatography THF: Tetrahydrofuran
DME: 1,2-dimethoxyethane
IPE: Diisopropyl ether
DMF: N,N-dimethylformamide
DMA: N,N-dimethylacetamide
NMP: N-methyl-2-pyrrolidone
DMSO: Dimethyl sulfoxide
CPBA: m-Chloroperbenzoic acid
TMSOTf: Trimethylsilyl triflate
DBU: 1,8-diazabicyclo[5.4.0]-7-undecene.

$^1$H NMR was measured with a Fourier transform NMR. ACD/SpecManager (brand name) etc., was used for the analysis. No description is provided for the extremely slight peaks of the protons of, for example, hydroxy groups and amino groups, etc.

The MS was measured using an LC/MS. The ionization method used was an ESI method or APCI method. The data described is the actual values (found). Usually the molecular ion peaks are seen, but when a compound has a t-butoxycarbonyl group, a peak after elimination of a tert-butoxycarbonyl group or tert-butyl group may be observed as a fragment ion. Moreover, in the case of a compound having a hydroxy group, a peak after the elimination of $H_2O$ may be observed. In the case of a salt, usually a fragment ion peak or the molecular ion peak of the compound is observed.

In the optical rotation $((\alpha)_D)$, the unit of the sample concentration (c) is g/100 mL.

For the elemental analysis values (Anal), theoretical values (Calcd) and the actual values (Found) are provided.

Example 1

Ethyl 6-((4-chloro-2,3-dihydro-1H-inden-1-yl)sulfonyl)cyclohex-1-ene-1-carboxylate (a mixture of 4 stereoisomers)

Step A

Sodium borohydride (1.7 g) was added with ice cooling to an ethanol solution (60 mL) of 4-chloroindan-1-one (5.0 g) and the mixture was stirred at room temperature for one hour. About half of the solvent was eliminated by distillation under reduced pressure, and water was added to the residue and extraction performed with ethyl acetate. The liquid extract was washed with saturated aqueous sodium chloride solution and was dried with sodium sulfate, and the solvent was eliminated by distillation under reduced pressure, and 4-chloroindan-1-ol (5.0 g) was obtained as a white solid.

$^1$H NMR (300 MHz, CDCl$_3$) δ 1.77 (1H, d, J=7.2 Hz), 1.91-2.03 (1H, m), 2.47-2.59 (1H, m), 2.79-2.90 (1H, m), 3.05-3.16 (1H, m), 5.25-5.32 (1H, m), 7.17-7.33 (3H, m).

Step B

Phosphorous tribromide (2.8 mL) was added at 0° C. to a diethyl ether solution (70 mL) of 4-chloroindan-1-ol (5.0 g) and the mixture was stirred at the same temperature for four hours. The reaction mixture was diluted with saturated aqueous sodium bicarbonate solution and extracted with ethyl acetate. The liquid extract was washed with saturated aqueous sodium chloride solution and was dried with magnesium sulfate, and the solvent was eliminated by distillation under reduced pressure, and 1-bromo-4-chloroindane (6.83 g) was obtained as a colorless oily substance.

$^1$H NMR (300 MHz, CDCl$_3$) δ 2.47-2.72 (2H, m), 2.92-3.05 (1H, m), 3.11-3.26 (1H, m), 5.57 (1H, dd, J=6.2, 2.5 Hz), 7.15-7.26 (2H, m), 7.31 (1H, d, J=7.6 Hz).

Step C

Potassium carbonate (7.74 g) was added at room temperature to a mixture of glutaraldehyde (5.6 M aqueous solution, 150 mL) and ethyl (diethoxyphosphoryl)acetate (115 mL), and the mixture was stirred at the same temperature for one hour. An aqueous solution (300 mL) of potassium carbonate (116 g) was added to the reaction mixture, and it was stirred overnight at the same temperature. Sodium chloride (100 g) was added to the reaction mixture and extraction was performed with ethyl acetate. The liquid extract was concentrated, and the residue was purified by silica gel column chromatography (ethyl acetate/hexane) and ethyl 6-hydroxycyclohex-1-ene-1-carboxylate (54.6 g) was obtained as a colorless oily substance.

$^1$H NMR (300 MHz, CDCl$_3$) δ 1.29-1.34 (3H, m), 1.54-1.62 (1H, m), 1.71-1.85 (3H, m), 2.10-2.30 (2H, m), 3.13 (1H, d, J=2.6 Hz), 4.24 (2H, q, J=6.9 Hz), 4.54 (1H, brs), 7.10 (1H, t, J=4.0 Hz).

Step D

N,N-dimethyl-4-aminopyridine (3.88 g) and acetic anhydride (90 mL) were successively added at room temperature to a pyridine solution (350 mL) of ethyl 6-hydroxycyclohex-1-ene-1-carboxylate (54.0 g), and the mixture was stirred at the same temperature for one hour. The reaction mixture was diluted with saturated aqueous sodium bicarbonate solution and extraction was performed with ethyl acetate. The liquid extract was washed with saturated aqueous sodium bicarbonate solution and saturated aqueous sodium chloride solution and was dried with magnesium sulfate, and the solvent was eliminated by distillation under reduced pressure. The residue was purified by silica gel column chromatography (ethyl acetate/hexane) and ethyl 6-acetoxycyclohex-1-ene-1-carboxylate (42.0 g) was obtained as a colorless oily substance.

MS: [M+H]$^+$213.2.

Step E

Triethylamine (30.3 mL) and potassium thioacetate (27.1 g) were successively added at room temperature to an ethanol solution (320 mL) of ethyl 6-acetoxycyclohex-1-ene-1-carboxylate (42.0 g), and the mixture stirred overnight at the same temperature. The reaction mixture was concentrated under reduced pressure, and water was added to the residue and extraction was performed with ethyl acetate. The liquid extract was washed with saturated aqueous sodium chloride solution and was dried with sodium sulfate, and the solvent was eliminated by distillation under reduced pressure. The residue was purified by silica gel column chromatography (ethyl acetate/hexane) and ethyl 6-(acetylsulfanyl)cyclohex-1-ene-1-carboxylate (37.1 g) was obtained as a colorless oily substance.

MS: [M+H]$^+$229.2.

Step F 4N hydrochloric acid (ethyl acetate solution, 203 mL) was added at room temperature to an ethanol solution (200 mL) of ethyl 6-(acetylsulfanyl)cyclohex-1-ene-1-carboxylate (37.0 g) and the mixture was stirred overnight at 50° C. The reaction mixture was concentrated under reduced pressure, and saturated aqueous sodium bicarbonate solution was added to the residue and extraction was performed with ethyl acetate. The liquid extract was washed with water and saturated aqueous sodium chloride solution and was dried with sodium sulfate, and the solvent was eliminated by distillation under reduced pressure. The residue was purified by silica gel column chromatography (ethyl acetate/hexane) and ethyl 6-sulfanylcyclohex-1-ene-1-carboxylate (21.0 g) was obtained as a colorless oily substance.

$^1$H NMR (300 MHz, CDCl$_3$) δ 1.31 (3H, t, J=7.0 Hz), 1.66-1.75 (1H, m), 1.85-1.97 (3H, m), 2.11 (1H, d, J=6.8 Hz), 2.14-2.38 (2H, m), 4.01-4.08 (1H, m), 4.18-4.28 (2H, m), 6.92-6.96 (1H, m).

Step G

DBU (0.18 mL) was added with ice cooling to a mixture of ethyl 6-sulfanylcyclohex-1-ene-1-carboxylate (200 mg), 1-bromo-4-chloroindane (249 mg) and DMF (4 mL), and the mixture was stirred at the same temperature for 20 minutes. The reaction mixture was diluted with water and extracted with ethyl acetate. The liquid extract was washed with water and saturated aqueous sodium chloride solution and was dried with magnesium sulfate, and the solvent was eliminated by distillation under reduced pressure. The residue was purified by silica gel column chromatography (ethyl acetate/hexane) and ethyl 6-((4-chloro-2,3-dihydro-1H-inden-1-yl)sulfanyl)cyclohex-1-ene-1-carboxylate (a mixture of 4 stereoisomers) (338 mg) was obtained as a colorless oily substance.

$^1$H NMR (300 MHz, CDCl$_3$) δ 1.28-1.34 (3H, m), 1.68-1.85 (2H, m), 1.88-2.04 (2H, m), 2.13-2.30 (2H, m), 2.30-2.45 (1H, m), 2.51-2.67 (1H, m), 2.87-2.98 (1H, m), 3.08-3.20 (1H, m), 3.97 (1H, d, J=14.4 Hz), 4.17-4.27 (2H, m), 4.50-4.60 (1H, m), 6.94-6.99 (1H, m), 7.09-7.21 (2H, m), 7.23-7.33 (1H, m).

Step H mCPBA (4.14 g, 72%) was added with ice cooling to a mixture of ethyl 6-((4-chloro-2,3-dihydro-1H-inden-1-yl)sulfanyl)cyclohex-1-ene-1-carboxylate (a mixture of 4 stereoisomers) (338 mg) and acetonitrile (4 mL), and the mixture was stirred at room temperature for one hour. The reaction mixture was diluted with saturated aqueous sodium bicarbonate solution and extracted with ethyl acetate. The liquid extract was washed with aqueous sodium chloride solution and was dried with magnesium sulfate, and the solvent was eliminated by distillation under reduced pressure. The residue was purified by silica gel column chromatography (ethyl acetate/hexane) and ethyl 6-((4-chloro-2,3-dihydro-1H-inden-1-yl)sulfonyl)cyclohex-1-ene-1-carboxylate (a mixture of 4 stereoisomers) (342 mg) was obtained as a colorless oily substance.

$^1$H NMR (300 MHz, CDCl$_3$) δ 1.30-1.40 (3H, m), 1.53-1.79 (2H, m), 1.94-2.15 (1H, m), 2.17-2.32 (1H, m), 2.35-2.52 (2.5H, m), 2.58-2.75 (1H, m), 2.86-3.09 (1.5H, m), 3.21-3.36 (1H, m), 4.22-4.31 (2H, m), 4.36-4.41 (0.5H, m), 4.59-4.64 (0.5H, m), 4.86-4.92 (1H, m), 7.15-7.24 (1H, m), 7.28-7.32 (1H, m), 7.38-7.45 (1H, m), 7.48 (0.5H, d, J=7.6 Hz), 7.62 (0.5H, d, J=7.6 Hz).

Example 2

Ethyl (2R,3R)-8-((4-chloro-2,3-dihydro-1H-inden-1-yl)sulfonyl)-2,3-bis(hydroxymethyl)-1,4-dioxaspiro[4.5]dec-6-ene-7-carboxylate (a mixture of 4 diastereomers)

Step A

Sodium borohydride (52.5 g) was added with ice cooling to a methanol solution (1000 mL) of dimethyl (4S,5S)-2,2-dimethyl-1,3-dioxolane-4,5-dicarboxylate (87 mL) and the mixture was stirred at the same temperature for one hour and at room temperature overnight. The reaction mixture was concentrated under reduced pressure, and then diluted with saturated aqueous sodium chloride solution and stirred at room temperature for one hour, and then extracted eight times with ethyl acetate. The liquid extracts were combined and dried with sodium sulfate, and the solvent was eliminated by distillation under reduced pressure ((4R,5R)-2,2-dimethyl-1,3-dioxolane-4,5-diyl)dimethanol (64.8 g) was obtained as a straw-colored oily substance.

$^1$H NMR (300 MHz, DMSO-d$_6$) δ 1.30 (6H, s), 3.40-3.58 (4H, m), 3.67-3.82 (2H, m), 4.81 (2H, t, J=5.7 Hz).

Step B

Amberlyst 15 hydrogen form (4.8 g, purchased from SIGMA-ALDRICH) was added at room temperature to a mixture of ((4R,5R)-2,2-dimethyl-1,3-dioxolane-4,5-diyl)dimethanol (86 g), methanol (121 mL) and water (1205 mL), and the mixture was stirred overnight at 60° C. The solids were eliminated by filtration, and the filtrate was concentrated under reduced pressure. Ethanol was added to the residue, and the mixture was concentrated to dryness. The obtained solids were brayed with mortar, and washed with liquid mixture of hexane/IPE=1/1, and (2R,3R)-butane-1,2,3,4-tetraol (51.7 g) was obtained.

$^1$H NMR (300 MHz, DMSO-d$_6$) δ 2.48-2.53 (2H, m), 3.28-3.43 (4H, m), 4.22 (2H, d, J=5.7 Hz), 4.35-4.48 (2H, m).

Step C

Benzoyl chloride (103 mL) was added at room temperature to NMP solution (1000 mL) of (2R,3R)-butane-1,2,3,4-tetraol (51.7 g) and the mixture was stirred at 50° C. for two hours. Water (1500 mL) was added to the reaction mixture and the solids formed were recovered by filtration and washed with water. The obtained solids were dissolved in ethyl acetate and washed with water and saturated aqueous sodium chloride solution and dried with magnesium sulfate. The solvent was eliminated by distillation under reduced pressure, and the obtained solids were recrystallized from ethyl acetate/hexane, and (2R,3R)-2,3-dihydroxybutane-1,4-diyl dibenzoate (77.3 g) was obtained.

MS, found: 353.0.

Step D

Chlorotrimethylsilane (62.8 mL) was added with ice cooling to a mixture of (2R,3R)-2,3-dihydroxybutane-1,4-diyl dibenzoate (77.3 g), N,N-dimethyl-4-aminopyridine (2.86 g), triethylamine (71.8 mL) and DMF (780 mL), and the mixture was stirred at the same temperature for one hour. The reaction mixture was diluted with saturated aqueous sodium bicarbonate solution and extracted with ethyl acetate. The liquid extract was washed with water and saturated aqueous sodium chloride solution and was dried with magnesium sulfate, and the solvent was eliminated by distillation under reduced pressure. The obtained solids were washed with hexane, and (2R,3R)-2,3-bis((trimethylsilyl)oxy)butane-1,4-diyl dibenzoate (105 g) was obtained.

MS, found: 475.2.

Step E

A THF solution (300 mL) of 1,4-dioxaspiro[4.5]decan-8-one (100 g) was added while heating under reflux to a mixture of diethyl carbonate (189 g), potassium t-butoxide (216 g) and THF (900 mL), and the mixture was stirred at the same temperature for five hours. The solids recovered by filtration were washed with ethyl acetate and dissolved in water (100 mL), and then added to a liquid mixture of water (50 mL) and acetic acid (50 mL) while ice cooling, and then extracted three times with ethyl acetate. The liquid extracts were combined and washed with water (twice), saturated aqueous sodium bicarbonate solution and saturated aqueous sodium chloride solution and dried with magnesium sulfate and filtered using silica gel. The filtrate was concentrated under reduced pressure, and ethyl 8-hydroxy-1,4-dioxaspiro[4.5]dec-7-ene-7-carboxylate (101 g) was obtained as an oily substance.

$^1$H NMR (300 MHz, DMSO-d$_6$) δ 1.13-1.21 (3H, m), 1.76 (2H, t, J=6.6 Hz), 2.33-2.42 (4H, m), 3.86-3.99 (6H, m), 12.14 (1H, s).

Step F

Trifluoromethanesulfonic anhydride (124 mL) was added at −78° C. to a mixture of ethyl 8-hydroxy-1,4-dioxaspiro [4.5]dec-7-ene-7-carboxylate (115 g), N-ethyl-N-(1-methylethyl) propan-2-amine (106 mL) and toluene (1008 mL), and the mixture was stirred at the same temperature for one hour. The reaction mixture was diluted with saturated aqueous sodium bicarbonate solution and was stirred at room temperature for 30 minutes, and thereafter, about half of the organic solvent was eliminated by distillation under reduced pressure, and the obtained mixture was extracted twice with ethyl acetate. The liquid extracts were combined and washed with water and saturated aqueous sodium chloride solution and dried with magnesium sulfate, and the solvent was eliminated by distillation under reduced pressure, and ethyl 8-(((trifluoromethyl)sulfonyl)oxy)-1,4-dioxaspiro[4.5]dec-7-ene-7-carboxylate (181 g) was obtained.

MS: [M+H]+ 361.0.

Step G

Potassium thioacetate (91 g) was added at room temperature to a DMSO (500 mL) solution of ethyl 8-(((trifluoromethyl)sulfonyl)oxy)-1,4-dioxaspiro[4.5]dec-7-ene-7-carboxylate (144 g) and the mixture was stirred at the same temperature for six hours. The reaction mixture was diluted with water and extracted with ethyl acetate. The liquid extract was washed with water and saturated aqueous sodium chloride solution and was dried with magnesium sulfate, and the solvent was eliminated by distillation under reduced pressure. The residue was purified by silica gel column chromatography (ethyl acetate/hexane) and ethyl 8-(acetylsulfanyl)-1,4-dioxaspiro[4.5]dec-7-ene-7-carboxylate (71.8 g) was obtained as a straw-colored oily substance.

MS, found: 309.0.

Step H 4N hydrochloric acid (ethyl acetate solution, 345 mL) was added with ice cooling to a THF (500 mL) solution of ethyl 8-(acetylsulfanyl)-1,4-dioxaspiro[4.5]dec-7-ene-7-carboxylate (79.1 g) and the mixture was stirred at room temperature for six hours, and then further 4N hydrochloric acid (ethyl acetate solution, 1036 mL) was added, and the mixture was stirred overnight at room temperature. The reaction mixture was concentrated down under reduced pressure to a volume of about 500 mL, and then diluted with water, and extraction was performed with ethyl acetate. The liquid extract was washed with water, saturated aqueous sodium bicarbonate solution and saturated aqueous sodium chloride solution and was dried with magnesium sulfate, and the solvent was eliminated by distillation under reduced pressure. The residue was purified by silica gel column chromatography (ethyl acetate/hexane) and ethyl 6-(acetylsulfanyl)-3-oxocyclohex-1-ene-1-carboxylate (59.1 g) was obtained as a straw-colored oily substance.

MS=(M−H)− 241.0.

Step I

Pyridinium p-toluenesulfonate (20.2 g) was added with ice cooling to a mixture of ethyl 6-(acetylsulfanyl)-3-oxocyclohex-1-ene-1-carboxylate (18.5 g), trimethoxymethane (40.5 g) and methanol (382 mL), and the mixture was stirred at room temperature for six hours. The reaction mixture was diluted with saturated aqueous sodium bicarbonate solution, and the organic solvent was eliminated by distillation under reduced pressure. The residue was extracted twice with ethyl acetate, and the extracts were combined and washed with water and saturated aqueous sodium chloride solution and was dried with sodium sulfate, and the solvent was eliminated by distillation under reduced pressure. A procedure wherein toluene was added to the residue and then eliminated by distillation under vacuum, was repeated several times, and ethyl 6-(acetylsulfanyl)-3,3-dimethoxycyclohex-1-ene-1-carboxylate (22.6 g) was thereby obtained.

$^1$H NMR (300 MHz, CDCl$_3$) δ 1.27 (3H, t, J=7.0 Hz), 1.70-1.83 (1H, m), 1.84-1.96 (1H, m), 1.98-2.08 (1H, m), 2.12-2.28 (1H, m), 2.32 (3H, s), 3.25 (3H, s), 3.30 (3H, s), 4.15-4.26 (2H, m), 4.63-4.70 (1H, m), 6.81-7.03 (1H, m).

Step J

TMSOTf (755 μL) was added with ice cooling to a mixture of ethyl 6-(acetylsulfanyl)-3,3-dimethoxycyclohex-1-ene-1-carboxylate (24 g), (2R,3R)-2,3-bis((trimethylsilyl) oxy)butane-1,4-diyl dibenzoate (39.5 g) and acetonitrile (550 mL), and the mixture was stirred at the same temperature for one hour. The reaction mixture was concentrated under reduced pressure, and the residue was purified by silica gel column chromatography (ethyl acetate/hexane). The obtained solids were washed with hexane and ethyl (2R,3R)-8-(acetylsulfanyl)-2,3-bis((benzoyloxy)methyl)-1, 4-dioxaspiro[4.5]dec-6-ene-7-carboxylate (a mixture of 2 diastereomers) (41.5 g) was obtained.

MS, found: 577.1.

Step K

Potassium carbonate (86 mg) was added with ice cooling to a mixture of ethyl (2R,3R)-8-(acetylsulfanyl)-2,3-bis ((benzoyloxy)methyl)-1,4-dioxaspiro[4.5]dec-6-ene-7-carboxylate (a mixture of 2 diastereomers) (115 mg), 1-bromo-4-chloroindane (48 mg) and methanol (4 mL), and the mixture was stirred at room temperature for three hours. The reaction mixture was diluted with 1N hydrochloric acid and extraction was performed with ethyl acetate/THF liquid mixture. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and ethyl (2R,3R)-8-((4-chloro-2,3-dihydro-1H-inden-1-yl) sulfanyl)-2,3-bis(hydroxymethyl)-1,4-dioxaspiro[4.5]dec-6-ene-7-carboxylate (a mixture of 4 diastereomers) (62.0 mg) was obtained as a colorless oily substance. MS, found: 477.4.

Step L mCPBA (66.7 mg, 74%) was added with ice cooling to an acetonitrile solution (2 mL) of ethyl (2R,3R)-8-((4-chloro-2,3-dihydro-1H-inden-1-yl)sulfanyl)-2,3-bis(hydroxymethyl)-1,4-dioxaspiro[4.5]dec-6-ene-7-carboxylate (a mixture of 4 diastereomers) (62.0 mg) and the mixture was stirred at room temperature for two hours. The reaction mixture was diluted with water and extracted with ethyl acetate. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and ethyl (2R,3R)-8-((4-chloro-2,3-dihydro-1H-inden-1-yl)sulfonyl)-2,3-bis(hydroxymethyl)-1,4-dioxaspiro[4.5]dec-6-ene-7-carboxylate (a mixture of 4 diastereomers) (57 mg) was obtained.

$^1$H NMR (400 MHz, CDCl$_3$) δ 1.30-1.41 (3H, m), 1.83-1.95 (1H, m), 2.07-2.15 (1H, m), 2.27-2.51 (3.5H, m), 2.59-2.71 (1H, m), 2.84-2.93 (0.5H, m), 2.96-3.11 (1H, m), 3.20-3.33 (1H, m), 3.68-3.77 (2H, m), 3.78-3.91 (2H, m), 3.98-4.04 (0.5H, m), 4.07-4.36 (5H, m), 4.55-4.60 (0.5H, m), 4.84-4.93 (1H, m), 6.92-6.97 (0.5H, m), 6.99-7.04 (0.5H, m), 7.16-7.23 (1H, m), 7.29-7.34 (1H, m), 7.45-7.50 (0.5H, m), 7.52-7.59 (0.5H, m).

Example 3

Ethyl (2S,3S)-8-((4-chloro-2,3-dihydro-1H-inden-1-yl)sulfonyl)-2,3-bis(hydroxymethyl)-1,4-dioxaspiro[4.5]dec-6-ene-7-carboxylate (a mixture of 4 diastereomers)

Step A

Amberlyst 15 hydrogen form (1.0 g, purchased from SIGMA-ALDRICH) was added at room temperature to the mixture of ((4S,5S)-2,2-dimethyl-1,3-dioxolane-4,5-diyl)dimethanol (30.0 g), methanol (28 mL) and water (280 mL), and the mixture was stirred overnight at 60° C. The solids were eliminated by filtration, and the filtrate was concentrated under reduced pressure. The obtained solids were washed with hexane, and (2S,3S)-butane-1,2,3,4-tetraol (22.1 g) was obtained.

$^1$H NMR (300 MHz, DMSO-$d_6$) δ 3.32-3.48 (6H, m), 4.21 (2H, d, J=5.3 Hz), 4.37-4.44 (2H, m).

Step B

Benzoyl chloride (39.8 mL) was added at room temperature to an NMP solution (200 mL) of (2S,3S)-butane-1,2,3,4-tetraol (19.0 g) and the mixture was stirred at 50° C. for two hours. The reaction mixture was cooled to room temperature, and thereafter, water (800 mL) was added, and the mixture was stirred at room temperature for two hours. The solids were recovered by filtration and dissolved in ethyl acetate and dried with sodium sulfate. The solvent was eliminated by distillation under reduced pressure, and the obtained solids were washed with ethyl acetate/hexane liquid mixture, and (2S,3S)-2,3-dihydroxybutane-1,4-diyl dibenzoate (31.6 g) was obtained.

MS, found: 353.1.

Step C

Chlorotrimethylsilane (16.3 mL) was added with ice cooling to a mixture of (2S,3S)-2,3-dihydroxybutane-1,4-diyl dibenzoate (20.0 g), N,N-dimethyl-4-aminopyridine (0.74 g), triethylamine (18.6 mL) and DMF (300 mL), and the mixture was stirred at the same temperature for two hours. The reaction mixture was diluted with saturated aqueous sodium bicarbonate solution and extracted with ethyl acetate. The liquid extract was washed with water and saturated aqueous sodium chloride solution and was dried with magnesium sulfate, and the solvent was eliminated by distillation under reduced pressure, and (2S,3S)-2,3-bis((trimethylsilyl)oxy)butane-1,4-diyl dibenzoate (22.5 g) was obtained as a white solid.

$^1$H NMR (300 MHz, CDCl$_3$) δ 0.15-0.19 (18H, m), 4.09-4.16 (2H, m), 4.34-4.43 (2H, m), 4.47-4.57 (2H, m), 7.42-7.51 (4H, m), 7.51-7.60 (2H, m), 8.03-8.08 (4H, m).

Step D

TMSOTf (176 μL) was added with ice cooling to a mixture of ethyl 6-(acetylsulfanyl)-3,3-dimethoxycyclohex-1-ene-1-carboxylate (5.61 g), (2S,3S)-2,3-bis((trimethylsilyl)oxy)butane-1,4-diyl dibenzoate (12.0 g) and acetonitrile (100 mL), and the mixture was stirred at the same temperature for one hour. The reaction mixture was concentrated under reduced pressure, and the residue was purified by silica gel column chromatography (ethyl acetate/hexane). The obtained solids were recrystallized from ethyl acetate/hexane and ethyl (2S,3S)-8-(acetylsulfanyl)-2,3-bis((benzoyloxy)methyl)-1,4-dioxaspiro[4.5]dec-6-ene-7-carboxylate (a mixture of 2 diastereomers) (10.1 g) was obtained.

MS, found: 577.1.

Step E

Potassium carbonate (202 mg) was added with ice cooling to a mixture of ethyl (2S,3S)-8-(acetylsulfanyl)-2,3-bis((benzoyloxy)methyl)-1,4-dioxaspiro[4.5]dec-6-ene-7-carboxylate (a mixture of 2 diastereomers) (270 mg), 1-bromo-4-chloroindane (113 mg) and methanol (8 mL), and the mixture was stirred at room temperature for three hours. The reaction mixture was diluted with 1N hydrochloric acid and extraction was performed with an ethyl acetate/THF liquid mixture. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and ethyl (2S,3S)-8-((4-chloro-2,3-dihydro-1H-inden-1-yl)sulfanyl)-2,3-bis(hydroxymethyl)-1,4-dioxaspiro[4.5]dec-6-ene-7-carboxylate (a mixture of 4 diastereomers) (177 mg) was obtained as a colorless oily substance.

MS, found: 477.3.

Step F mCPBA (205 mg, 72%) was added with ice cooling to an acetonitrile solution (4 mL) of ethyl (2S,3S)-8-((4-chloro-2,3-dihydro-1H-inden-1-yl)sulfanyl)-2,3-bis(hydroxymethyl)-1,4-dioxaspiro[4.5]dec-6-ene-7-carboxylate (a mixture of 4 diastereomers) (177 mg) and the mixture was stirred at 50° C. for three hours. The reaction mixture was diluted with water, and extracted with ethyl acetate. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and then separated and recovered twice using HPLC (C18, mobile phase: water/acetonitrile (0.1% TFA containing system)) and ethyl (2S,3S)-8-((4-chloro-2,3-dihydro-1H-inden-1-yl)sulfonyl)-2,3-bis(hydroxymethyl)-1,4-dioxaspiro[4.5]dec-6-ene-7-carboxylate (a mixture of 4 diastereomers) (26.0 mg) was obtained.

$^1$H NMR (300 MHz, CDCl$_3$) δ 1.32-1.38 (3H, m), 1.91-2.07 (2H, m), 2.39-2.61 (3H, m), 2.82-3.04 (2H, m), 3.22-3.32 (1H, m), 3.67-3.75 (2H, m), 3.81-3.90 (2H, m), 4.01-4.35 (6H, m), 4.54-4.92 (2H, m), 6.91-7.03 (1H, m), 7.17-7.23 (1H, m), 7.29-7.33 (1H, m), 7.47-7.58 (1H, m).

Example 4

Ethyl 6-((7-chloro-2,3-dihydro-1H-inden-1-yl)sulfonyl)-3-hydroxycyclohex-1-ene-1-carboxylate (racemate, low polarity)

Example 5

Ethyl 6-((7-chloro-2,3-dihydro-1H-inden-1-yl)sulfonyl)-3-hydroxycyclohex-1-ene-1-carboxylate (racemate, high polarity)

Step A

Sodium borohydride (3.41 g) was added with ice cooling to an ethanol solution (200 mL) of 7-chloroindan-1-one (10.0 g) and the mixture was stirred overnight at room temperature. About half of the solvent was eliminated by distillation under reduced pressure, and water was added to the residue and extraction was performed with ethyl acetate. The liquid extract was washed with saturated aqueous sodium chloride solution and was dried with sodium sulfate, and the solvent was eliminated by distillation under reduced pressure. The residue was purified by silica gel column chromatography (ethyl acetate/hexane) and 7-chloroindan-1-ol (8.82 g) was obtained as a straw-colored oily substance.

¹H NMR (400 MHz, CDCl₃) δ 2.06-2.16 (1H, m), 2.30 (1H, d, J=2.9 Hz), 2.37-2.47 (1H, m), 2.82-2.91 (1H, m), 3.15-3.24 (1H, m), 5.40-5.45 (1H, m), 7.14-7.23 (3H, m).
Step B Diethyl ether solution (10 mL) of phosphorous tribromide (5.43 mL) was added at 0° C. to a diethyl ether solution (200 mL) of 7-chloroindan-1-ol (8.82 g) and the mixture was stirred at the same temperature for two hours. The reaction mixture was diluted with water and extracted with ethyl acetate. The liquid extract was washed with saturated aqueous sodium chloride solution and was dried with magnesium sulfate, and the solvent was eliminated by distillation under reduced pressure, and 1-bromo-7-chloroindane (11.8 g) was obtained as a straw-colored oily substance.

¹H NMR (300 MHz, CDCl₃) δ 2.51-2.58 (2H, m), 2.87-2.96 (1H, m), 3.22-3.37 (1H, m), 5.56-5.62 (1H, m), 7.14-7.22 (3H, m).
Step C Sodium borohydride (0.24 g) was added with ice cooling to a mixture of ethyl 6-(acetylsulfanyl)-3-oxocyclohex-1-ene-1-carboxylate (1.56 g), cerium chloride (III) (2.88 g), ethanol (35 mL), and the mixture was stirred at the same temperature for three hours. The reaction mixture was diluted with water, and extracted with ethyl acetate. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and ethyl 3-hydroxy-6-sulfanylcyclohex-1-ene-1-carboxylate (single relative configuration) (361 mg) was obtained as a colorless oily substance.

¹H NMR (300 MHz, CDCl₃) δ 1.32 (3H, t, J=7.0 Hz), 1.75 (1H, brs), 1.84-1.93 (1H, m), 1.99-2.12 (3H, m), 2.19 (1H, d, J=7.2 Hz), 3.95-4.02 (1H, m), 4.25 (2H, q, J=7.2 Hz), 4.34-4.41 (1H, m), 6.76-6.79 (1H, m).
Step D Potassium carbonate (247 mg) was added with ice cooling to a mixture of ethyl 3-hydroxy-6-sulfanylcyclohex-1-ene-1-carboxylate (single relative configuration) (361 mg), 1-bromo-7-chloroindane (413 mg) and methanol (6 mL), and the mixture was stirred at the same temperature for two hours. The reaction mixture was diluted with 1N hydrochloric acid and extracted with ethyl acetate. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and ethyl 6-((7-chloro-2,3-dihydro-1H-inden-1-yl)sulfanyl)-3-hydroxycyclohex-1-ene-1-carboxylate (a mixture of 4 stereoisomers) (245 mg) obtained as a colorless oily substance.

MS, found: 375.1.
Step E mCPBA (646 mg, 72%) was added with ice cooling to an acetonitrile solution (8 mL) of ethyl 6-((7-chloro-2,3-dihydro-1H-inden-1-yl)sulfanyl)-3-hydroxycyclohex-1-ene-1-carboxylate (a mixture of 4 stereoisomers) (432 mg) and the mixture was stirred at room temperature for five hours. The reaction mixture was diluted with saturated aqueous sodium bicarbonate solution and extracted with ethyl acetate. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and a fraction of a low polarity compound and a fraction of a high polarity compound were recovered, and these were respectively concentrated, and ethyl 6-((7-chloro-2,3-dihydro-1H-inden-1-yl)sulfonyl)-3-hydroxycyclohex-1-ene-1-carboxylate (racemate) was obtained.

Low polarity compound (yield 37 mg) ¹H NMR (300 MHz, CDCl₃) δ 1.36 (3H, t, J=7.2 Hz), 1.83-2.14 (4H, m), 2.32-2.51 (2H, m), 2.82-2.99 (2H, m), 3.36-3.48 (1H, m), 4.27-4.35 (3H, m), 4.85-4.90 (1H, m), 5.06 (1H, d, J=7.9 Hz), 7.19-7.25 (4H, m).

High polarity compound (yield 57 mg) ¹H NMR (300 MHz, CDCl₃) δ 1.24 (3H, t, J=7.0 Hz), 1.87-2.16 (4H, m), 2.47-2.64 (2H, m), 2.70-2.80 (1H, m), 2.86-2.95 (1H, m), 3.45-3.59 (1H, m), 4.16-4.26 (2H, m), 4.30-4.39 (1H, m), 4.52-4.57 (1H, m), 5.10 (1H, d, J=7.9 Hz), 7.19-7.25 (4H, m).

Example 6

Ethyl (2R,3R,8R)-8-(((1S)-7-chloro-2,3-dihydro-1H-inden-1-yl)sulfonyl)-2,3-bis(hydroxymethyl)-1,4-dioxaspiro[4.5]dec-6-ene-7-carboxylate Step A Potassium carbonate (5.70 g) was added with ice cooling to a mixture of ethyl (2R,3R)-8-(acetylsulfanyl)-2,3-bis((benzoyloxy)methyl)-1,4-dioxaspiro[4.5]dec-6-ene-7-carboxylate (a mixture of 2 diastereomers) (7.63 g), 1-bromo-7-chloroindane (3.19 g) and methanol (100 mL), and the mixture was stirred at room temperature for one hour. The reaction mixture was diluted with 1N hydrochloric acid, and extraction was performed with an ethyl acetate/THF liquid mixture. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and ethyl (2R,3R)-8-((7-chloro-2,3-dihydro-1H-inden-1-yl)sulfanyl)-2,3-bis(hydroxymethyl)-1,4-dioxaspiro[4.5]dec-6-ene-7-carboxylate (a mixture of 4 diastereomers) (3.86 g) was obtained as a colorless solid.

MS, found: 477.1.
Step B mCPBA (4.68 g, 72%) was added with ice cooling to a mixture of ethyl (2R,3R)-8-((7-chloro-2,3-dihydro-1H-inden-1-yl)sulfanyl)-2,3-bis(hydroxymethyl)-1,4-dioxaspiro[4.5]dec-6-ene-7-carboxylate (a mixture of 4 diastereomers) (3.86 g), acetonitrile (60 mL) and DMF (30 mL) and the mixture was stirred at room temperature for four hours. The reaction mixture was diluted with saturated aqueous sodium bicarbonate solution and extracted with ethyl acetate. The liquid extract was washed with water and saturated aqueous sodium chloride solution and was dried with magnesium sulfate, and the solvent was eliminated by distillation under reduced pressure. The residue was purified by silica gel column chromatography (ethyl acetate/hexane) and ethyl (2R,3R)-8-((7-chloro-2,3-dihydro-1H-inden-1-yl)sulfonyl)-2,3-bis(hydroxymethyl)-1,4-dioxaspiro[4.5]dec-6-ene-7-carboxylate (a mixture of 4 diastereomers) (3.23 g) was obtained as a colorless oily substance.

MS, found: 504.1.
Step C

Ethyl (2R,3R)-8-((7-chloro-2,3-dihydro-1H-inden-1-yl)sulfonyl)-2,3-bis(hydroxymethyl)-1,4-dioxaspiro[4.5]dec-6-ene-7-carboxylate (a mixture of 4 diastereomers) (100 mg) was separated and recovered using HPLC (column=CHIRALPAK IC, 50 mmID×500 mmL, mobile phase: hexane/ethyl acetate=20/80), and the fractions from the first peak and the second peak were recovered, combined, and concentrated (50 mg). 30 mg of the residue was separated and recovered by HPLC (column=CHIRALPAK IC, 50 mmID×500 mmL, mobile phase: 2-propanol), and the fraction from the second peak was recovered and concentrated, and ethyl (2R,3R,8R)-8-(((1S)-7-chloro-2,3-dihydro-1H-inden-1-yl)sulfonyl)-2,3-bis(hydroxymethyl)-1,4-dioxaspiro[4.5]dec-6-ene-7-carboxylate (18 mg) was thereby obtained.

$^1$H NMR (300 MHz, CDCl$_3$) δ 1.22 (3H, t, J=7.0 Hz), 1.90-1.99 (2H, m), 2.14-2.32 (2H, m), 2.42-2.64 (3H, m), 2.71-2.80 (1H, m), 2.84-2.95 (1H, m), 3.43-3.57 (1H, m), 3.67-3.77 (2H, m), 3.80-3.93 (2H, m), 4.07-4.26 (4H, m), 4.57 (1H, d, J=4.2 Hz), 5.10 (1H, d, J=7.9 Hz), 6.97-7.00 (1H, m), 7.17-7.25 (3H, m).

The Compound of Example 6 can be synthesized using a method of synthesis as per following Step D to Step I.

Step D

Borane dimethyl sulfide complex (12.1 mL) was added with ice cooling under a nitrogen atmosphere to a THF solution (200 mL) of 1M (3aR)-1-methyl-3,3-diphenyltetrahydro-3H-pyrrolo[1,2-c][1,3,2]oxazaborole (toluene solution, 48.0 mL) and the mixture was stirred at the same temperature for 30 minutes. A THF solution (130 mL) of 7-chloroindan-1-one (20.0 g) was added with ice cooling to the reaction mixture, and the mixture was stirred at the same temperature for one hour. Methanol (48.6 mL) was added to the reaction mixture, and concentration was performed under reduced pressure. The residue was diluted with 1N hydrochloric acid and extraction was performed with a liquid mixture of ethyl acetate/THF. The aqueous phase was extracted with ethyl acetate, and the extracts were combined and washed with saturated aqueous sodium chloride solution and dried with sodium sulfate, and the solvent was eliminated by distillation under reduced pressure. The residue was filtered through silica gel, and elution performed with ethyl acetate. The solvent was eliminated by distillation under reduced pressure, and the residue was purified by silica gel column chromatography (ethyl acetate/hexane). The obtained solids were recrystallized from toluene/hexane, and washed with a mixed solvent of cool toluene/hexane, and (1S)-7-chloroindan-1-ol (11.1 g) was obtained. Optical purity 99.8% ee (analytic conditions; CHIRALCEL OD, 4.6 mmID×250 mmL, mobile phase: hexane/2-propanol=90/10, flow rate: 1.0 mL/min, column temperature: 30° C.)

$^1$H NMR (300 MHz, CDCl$_3$) δ 2.11 (1H, dddd, J=13.9, 8.6, 4.2, 3.2 Hz), 2.27 (1H, d, J=3.8 Hz), 2.42 (1H, ddt, J=14.1, 8.7, 6.9 Hz), 2.87 (1H, ddd, J=16.3, 9.0, 4.2 Hz), 3.20 (1H, dt, J=16.1, 7.8 Hz), 5.43 (1H, dt, J=6.8, 3.4 Hz), 7.11-7.24 (3H, m).

The compound of Step D can also be synthesized according to the synthesis method shown in Step D'.

(Step D')

To a suspension of 7-chloroindan-1-one (25.0 g), potassium formate (25.2 g), 2-propanol (1.242 mL) and water (186 mL) was added chloro(((1S,2S)-(+)-2-amino-1,2-diphenylethyl)(4-toluenesulfonyl)amide)(p-cymene)ruthenium(II) (0.955 g) at room temperature, and the mixture was stirred overnight at 50° C. under argon atmosphere. The obtained mixture was extracted with ethyl acetate, and the extract was washed with saturated brine, and dried over magnesium sulfate, and the solvent was evaporated under reduced pressure. The residue was purified by silica gel column chromatography (ethyl acetate/hexane). To the obtained oil was added hexane (20 mL), and the mixture was solidified in a freezer. Hexane (200 mL) was added thereto, and the mixture was stirred at room temperature for 1 hr. The resulting solid was collected by filtration, and washed with hexane. The obtained solid was recrystallized from toluene, and (1S)-7-chloroindan-1-ol (5.19 g) was obtained as a white solid. Optical purity 99.5% ee (analysis condition; column: CHIRALCEL ODH, 4.6 mmID×250 mmL, mobile phase: hexane/2-propanol=90/10, flow rate: 1.0 mL/min, column temperature: 30° C.). The mother liquor and washing were combined, and concentrated to dryness, and the obtained solid was recrystallized from hexane, and additional (1S)-7-chloroindan-1-ol (13.2 g) was obtained as a white solid. Optical purity 99.5% ee (analysis condition; column: CHIRALCEL ODH, 4.6 mmID×250 mmL, mobile phase: hexane/2-propanol=90/10, flow rate: 1.0 mL/min, column temperature: 30° C.).

Step E

Phosphorous tribromide (2.80 mL) was added at 10° C. to a diethyl ether solution (150 mL) of (1S)-7-chloroindan-1-ol (5.0 g) and the mixture was stirred at the same temperature for two hours. The reaction mixture was diluted with saturated aqueous sodium bicarbonate solution and extracted with ethyl acetate. The liquid extract was washed with saturated aqueous sodium chloride solution and was dried with magnesium sulfate, and the solvent was eliminated by distillation under reduced pressure, and (1R)-1-bromo-7-chloroindane (6.13 g) was obtained as a colorless oily substance.

$^1$H NMR (300 MHz, CDCl$_3$) δ 2.52-2.59 (2H, m), 2.87-2.97 (1H, m), 3.22-3.37 (1H, m), 5.57-5.62 (1H, m), 7.15-7.23 (3H, m).

Step F

Potassium carbonate (11.9 g) was added with ice cooling to a methanol solution (281 mL) of ethyl (2R,3R)-8-(acetylsulfanyl)-2,3-bis((benzoyloxy)methyl)-1,4-dioxaspiro[4.5]dec-6-ene-7-carboxylate (a mixture of 2 diastereomer) (15.6 g) and the mixture was stirred at the same temperature for one hour. 1N hydrochloric acid (215 mL) was added to the reaction mixture and extraction was performed with ethyl acetate. The liquid extract was washed with saturated aqueous sodium chloride solution and was dried with sodium sulfate, and the solvent was eliminated by distillation under reduced pressure. The residue was purified by silica gel column chromatography (ethyl acetate/hexane) and ethyl (2R,3R)-2,3-bis(hydroxymethyl)-8-sulfanyl-1,4-dioxaspiro[4.5]dec-6-ene-7-carboxylate (a mixture of 2 diastereomers) (6.39 g) was obtained as a straw-colored oily substance.

$^1$H NMR (300 MHz, CDCl$_3$) δ 1.32 (3H, t, J=7.2 Hz), 1.81-2.03 (3H, m), 2.07-2.36 (4H, m), 3.66-4.32 (9H, m), 6.47-6.63 (1H, m).

Step G

Ethyl (2R,3R)-2,3-bis(hydroxymethyl)-8-sulfanyl-1,4-dioxaspiro[4.5]dec-6-ene-7-carboxylate (a mixture of 2 diastereomers) (7.50 g) was crystallized from toluene (5 mL) and pulverized in a mixed solvent of toluene/IPE=10/1. The solids were recovered by filtration, and ethyl (2R,3R,8R)-2,3-bis(hydroxymethyl)-8-sulfanyl-1,4-dioxaspiro[4.5]dec-6-ene-7-carboxylate (1.82 g) was obtained as a white solid.

$^1$H NMR (300 MHz, CDCl$_3$) δ 1.32 (3H, t, J=7.2 Hz), 1.83-2.32 (7H, m), 3.65-4.34 (9H, m), 6.58 (1H, s).

Step H

A THF solution (19 mL) of DBU (2.28 g) was added with ice cooling to a mixture of ethyl (2R,3R,8R)-2,3-bis(hydroxymethyl)-8-sulfanyl-1,4-dioxaspiro[4.5]dec-6-ene-7-carboxylate (3.50 g), (1R)-1-bromo-7-chloroindane (3.99 g) and THF (38 mL), and the mixture was stirred at the same temperature for one hour. The reaction mixture was diluted with water and extracted with ethyl acetate. The liquid extract was washed with saturated aqueous sodium chloride solution and was dried with sodium sulfate, and the solvent was eliminated by distillation under reduced pressure. The residue was purified by silica gel column chromatography (ethyl acetate/hexane). The obtained oil was kept in a freezer for 3 days, and crystallized from acetonitrile using the solid partially formed, and the solids recovered by filtration were recrystallized from acetonitrile/hexane, and ethyl (2R,3R,8R)-8-(((1S)-7-chloro-2,3-dihydro-1H-inden-1-yl)sulfanyl)-2,3-bis(hydroxymethyl)-1,4-dioxaspiro[4.5]dec-6-ene-7-carboxylate (2.60 g) was obtained as a white solid.

$^1$H NMR (400 MHz, CDCl$_3$) δ 1.30 (3H, t, J=7.2 Hz), 1.82-1.96 (3H, m), 2.02-2.40 (4H, m), 2.45-2.58 (1H, m), 2.89 (1H, dd, J=16.3, 8.2 Hz), 3.23-3.36 (1H, m), 3.64-3.76 (2H, m), 3.79-3.95 (3H, m), 4.05-4.33 (4H, m), 4.68 (1H, d, J=6.8 Hz), 6.54 (1H, s), 7.08-7.17 (3H, m).

Step I mCPBA (3.10 g, 70%) was added with ice cooling to a mixture of ethyl (2R,3R,8R)-8-(((1S)-7-chloro-2,3-dihydro-1H-inden-1-yl)sulfanyl)-2,3-bis(hydroxymethyl)-1,4-dioxaspiro[4.5]dec-6-ene-7-carboxylate (2.60 g), acetonitrile (20 mL) and DMF (20 mL), and the mixture was stirred overnight at room temperature. The reaction mixture was diluted with water and extracted with ethyl acetate. The liquid extract was washed with water, saturated aqueous sodium bicarbonate solution and saturated aqueous sodium chloride solution and was dried with sodium sulfate, and the solvent was eliminated by distillation under reduced pressure. The residue was purified by silica gel column chromatography (ethyl acetate/hexane) and the residue was crystallized from ethyl acetate/hexane. The solids recovered by filtration were recrystallized from ethyl acetate/heptane, and ethyl (2R,3R,8R)-8-(((1S)-7-chloro-2,3-dihydro-1H-inden-1-yl)sulfonyl)-2,3-bis(hydroxymethyl)-1,4-dioxaspiro[4.5]dec-6-ene-7-carboxylate (1.69 g) was obtained as a white solid.

Example 7

Ethyl (2S,3S,8R)-8-(((1S)-7-chloro-2,3-dihydro-1H-inden-1-yl)sulfonyl)-2,3-bis(hydroxymethyl)-1,4-dioxaspiro[4.5]dec-6-ene-7-carboxylate Step A Potassium carbonate (3.74 g) was added with ice cooling to a mixture of ethyl (2S,3S)-8-(acetylsulfanyl)-2,3-bis((benzoyloxy)methyl)-1,4-dioxaspiro[4.5]dec-6-ene-7-carboxylate (a mixture of 2 diastereomers) (5.0 g), 1-bromo-7-chloroindane (2.09 g) and methanol (80 mL), and the mixture was stirred at room temperature for one hour. The reaction mixture was diluted with 1N hydrochloric acid, and extraction was performed with ethyl acetate/THF liquid mixture. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and ethyl (2S,3S)-8-((7-chloro-2,3-dihydro-1H-inden-1-yl)sulfanyl)-2,3-bis(hydroxymethyl)-1,4-dioxaspiro[4.5]dec-6-ene-7-carboxylate (a mixture of 4 diastereomers) (2.16 g) was obtained as a colorless solid.

MS, found: 477.1.

Step B mCPBA (2.84 g, 72%) was added at room temperature to a mixture of ethyl (2S,3S)-8-((7-chloro-2,3-dihydro-1H-inden-1-yl)sulfanyl)-2,3-bis(hydroxymethyl)-1,4-dioxaspiro[4.5]dec-6-ene-7-carboxylate (2.16 g), acetonitrile (30 mL) and DMF (30 mL), and the mixture was stirred at room temperature for five hours. The reaction mixture was diluted with saturated aqueous sodium bicarbonate solution and extracted with ethyl acetate. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and ethyl (2S,3S)-8-((7-chloro-2,3-dihydro-1H-inden-1-yl)sulfonyl)-2,3-bis(hydroxymethyl)-1,4-dioxaspiro[4.5]dec-6-ene-7-carboxylate (a mixture of 4 diastereomers) (1.60 g) was obtained as a colorless solid.

MS, found: 509.1.

Step C

Ethyl (2S,3S)-8-((7-chloro-2,3-dihydro-1H-inden-1-yl)sulfonyl)-2,3-bis(hydroxymethyl)-1,4-dioxaspiro[4.5]dec-6-ene-7-carboxylate (a mixture of 4 diastereomers) (800 mg) was separated and recovered by HPLC (column=CHIRALPAK IC, 50 mmID×500 mmL, mobile phase: hexane/ethyl acetate=40/60), and the fractionated fraction from the fourth peak was recovered and concentrated, and ethyl (2S,3S,8R)-8-(((1S)-7-chloro-2,3-dihydro-1H-inden-1-yl)sulfonyl)-2,3-bis(hydroxymethyl)-1,4-dioxaspiro[4.5]dec-6-ene-7-carboxylate (196 mg) was obtained.

$^1$H NMR (300 MHz, CDCl$_3$) δ 1.21 (3H, t, J=7.0 Hz), 1.86-2.05 (3H, m), 2.15-2.28 (1H, m), 2.41-2.62 (3H, m), 2.71-2.81 (1H, m), 2.85-2.95 (1H, m), 3.44-3.57 (1H, m), 3.67-3.77 (2H, m), 3.81-3.91 (2H, m), 3.99-4.06 (1H, m), 4.10-4.26 (3H, m), 4.57 (1H, d, J=4.9 Hz), 5.08 (1H, d, J=8.3 Hz), 6.90-6.93 (1H, m), 7.17-7.25 (3H, m).

Example 8

(1-methylcyclopropyl)methyl (2S,3S)-8-((7-chloro-2,3-dihydro-1H-inden-1-yl)sulfonyl)-2,3-bis(hydroxymethyl)-1,4-dioxaspiro[4.5]dec-6-ene-7-carboxylate (a mixture of 4 diastereomers)

Step A 0.75M barium hydroxide octahydrate aqueous solution (23.7 mL) was added to an acetonitrile solution (60 mL) of ethyl (2S,3S)-8-((7-chloro-2,3-dihydro-1H-inden-1-yl)sulfanyl)-2,3-bis(hydroxymethyl)-1,4-dioxaspiro[4.5]dec-6-ene-7-carboxylate (a mixture of 4 diastereomers) (2.7 g) and the mixture was stirred at 60° C. for two hours. The reaction mixture was diluted with 1N hydrochloric acid and extracted with ethyl acetate. The organic phase was extracted with 1N aqueous sodium hydroxide solution and was washed with ethyl acetate. The aqueous phase was made acidic (pH=3 to 4) with 2N hydrochloric acid and extracted with ethyl acetate. The liquid extract was washed with saturated aqueous sodium chloride solution and was dried with magnesium sulfate, and the solvent was eliminated by distillation under reduced pressure, and (2S,3S)-8-((7-chloro-2,3-dihydro-1H-inden-1-yl)sulfanyl)-2,3-bis(hydroxymethyl)-1,4-dioxaspiro[4.5]dec-6-ene-7-carboxylic acid (a mixture of 4 diastereomers) (2.45 g) was obtained as a pale yellow solid.

MS, found: 449.1.

Step B

Diethyl diazene-1,2-dicarboxylate (40% toluene solution, 632 mg) was added with ice cooling to a mixture of (2S,3S)-8-((7-chloro-2,3-dihydro-1H-inden-1-yl)sulfanyl)-2,3-bis(hydroxymethyl)-1,4-dioxaspiro[4.5]dec-6-ene-7-carboxylic acid (a mixture of 4 diastereomers) (310 mg), (1-methylcyclopropyl)methanol (96 μL), triphenylphosphine (381 mg) and THF (6 mL), and the mixture was stirred overnight while warming to room temperature. The reaction mixture was diluted with water, and extracted with ethyl acetate. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and (1-methylcyclopropyl)methyl (2S,3S)-8-((7-chloro-2,3-dihydro-1H-inden-1-yl)sulfanyl)-2,3-bis(hydroxymethyl)-1,4-dioxaspiro[4.5]dec-6-ene-7-carboxylate (a mixture of 4 diastereomers) (206 mg) was obtained as a colorless solid.

MS, found: 518.2.

Step C mCPBA (219 mg, 72%) was added with ice cooling to a mixture of (1-methylcyclopropyl)methyl (2S,3S)-8-((7-chloro-2,3-dihydro-1H-inden-1-yl)sulfanyl)-2,3-bis(hydroxymethyl)-1,4-dioxaspiro[4.5]dec-6-ene-7-carboxylate (a mixture of 4 diastereomers) (206 mg), acetonitrile (1.5 mL) and DMF (3 mL), and the mixture was stirred at room temperature for four hours. The reaction mixture was diluted with saturated aqueous sodium bicarbonate solution and extracted with ethyl acetate. The liquid extract was washed with water and saturated aqueous sodium chloride solution and was dried with magnesium sulfate, and the solvent was eliminated by distillation under reduced pressure. The residue was purified by silica gel column chromatography (ethyl acetate/hexane) and (1-methylcyclopropyl)methyl (2S,3S)-8-((7-chloro-2,3-dihydro-1H-inden-1-yl)sulfonyl)-2,3-bis(hydroxymethyl)-1,4-dioxaspiro[4.5]dec-6-ene-7-carboxylate (a mixture of 4 diastereomers) (75 mg) was obtained.

$^1$H NMR (300 MHz, CDCl$_3$) δ 0.33-0.57 (4H, m), 1.08-1.22 (3H, m), 1.77-2.08 (4H, m), 2.14-2.30 (1.5H, m), 2.35-2.53 (2H, m), 2.57-2.64 (0.5H, m), 2.71-2.99 (2H, m), 3.38-3.55 (1H, m), 3.66-3.76 (2H, m), 3.80-3.91 (2H, m), 4.00-4.11 (2H, m), 4.15-4.25 (1H, m), 4.53-4.57 (0.5H, m), 4.91-4.99 (0.5H, m), 5.03-5.13 (1H, m), 6.91-7.04 (1H, m), 7.16-7.25 (3H, m).

Example 14

Ethyl (2R,3R,8R)-8-(((1S)-7-chloro-5-fluoro-2,3-dihydro-1H-inden-1-yl)sulfonyl)-2,3-bis(hydroxymethyl)-1,4-dioxaspiro[4.5]dec-6-ene-7-carboxylate Step A Borane dimethyl sulfide complex (15.0 mL) was added with ice cooling under a nitrogen atmosphere to a THF solution (100 mL) of (3aR)-1-methyl-3,3-diphenyltetrahydro-3H-pyrrolo [1,2-c][1,3,2]oxazaborole (3.0 g) and the mixture was stirred at the same temperature for one hour. A THF solution (20 mL) of 7-chloro-5-fluoroindan-1-one (5.0 g) was added at −78° C. to the reaction mixture, and the mixture was stirred overnight while warming to room temperature. The reaction mixture was diluted with ice cooling with methanol, and the reaction mixture was concentrated under reduced pressure. The residue was purified by silica gel column chromatography (ethyl acetate/hexane) and (1S)-7-chloro-5-fluoroindan-1-ol (4.87 g) was obtained as a straw-colored solid.

$^1$H NMR (300 MHz, CDCl$_3$) δ 2.08-2.21 (2H, m), 2.37-2.50 (1H, m), 2.80-2.91 (1H, m), 3.13-3.26 (1H, m), 5.35-5.41 (1H, m), 6.84-6.97 (2H, m).

Step B

Phosphorous tribromide (505 μL) was added at −78° C. to a diethyl ether solution (20 mL) of (1S)-7-chloro-5-fluoroindan-1-ol (1.0 g) and the mixture was stirred for two hours while warming to 0° C. The reaction mixture was diluted with saturated aqueous sodium bicarbonate solution and extracted with ethyl acetate. The liquid extract was washed with saturated aqueous sodium chloride solution and was dried with magnesium sulfate, and the solvent was eliminated by distillation under reduced pressure, and (1R)-1-bromo-7-chloro-5-fluoroindan (1.33 g) was obtained as a straw-colored oily substance.

$^1$H NMR (300 MHz, CDCl$_3$) δ 2.54-2.62 (2H, m), 2.86-2.95 (1H, m), 3.22-3.36 (1H, m), 5.51-5.57 (1H, m), 6.85-6.99 (2H, m).

Step C

DBU (0.16 mL) was added with ice cooling to a mixture of ethyl (2R,3R,8R)-2,3-bis(hydroxymethyl)-8-sulfanyl-1,4-dioxaspiro[4.5]dec-6-ene-7-carboxylate (286 mg), (1R)-1-bromo-7-chloro-5-fluoroindan (305 mg) and THF (6 mL), and the mixture was stirred at room temperature for one hour. The reaction mixture was diluted with water and extracted with ethyl acetate. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and ethyl (2R,3R,8R)-8-(((1S)-7-chloro-5-fluoro-2,3-dihydro-1H-inden-1-yl)sulfanyl)-2,3-bis(hydroxymethyl)-1,4-dioxaspiro[4.5]dec-6-ene-7-carboxylate (450 mg) was obtained as a colorless oily substance.

MS, found: 495.1.

Step D mCPBA (506 mg, 72%) was added with ice cooling to a mixture of ethyl (2R,3R,8R)-8-(((1S)-7-chloro-5-fluoro-2,3-dihydro-1H-inden-1-yl)sulfanyl)-2,3-bis(hydroxymethyl)-1,4-dioxaspiro[4.5]dec-6-ene-7-carboxylate (454 mg), acetonitrile (4 mL) and DMF (4 mL), and the mixture was stirred at room temperature for six hours. The reaction mixture was diluted with saturated aqueous sodium bicarbonate solution and extracted with ethyl acetate. The liquid extract was washed with water and saturated aqueous sodium chloride solution and was dried with magnesium sulfate, and the solvent was eliminated by distillation under reduced pressure. The residue was purified by silica gel column chromatography (ethyl acetate/hexane) and then crystallized from ethyl acetate/hexane. The solids recovered by filtration were recrystallized twice from ethyl acetate/hexane, and ethyl (2R,3R,8R)-8-(((1S)-7-chloro-5-fluoro-2,3-dihydro-1H-inden-1-yl)sulfonyl)-2,3-bis(hydroxymethyl)-1,4-dioxaspiro[4.5]dec-6-ene-7-carboxylate (64 mg) was obtained.

$^1$H NMR (300 MHz, CDCl$_3$) δ 1.27 (3H, t, J=7.2 Hz), 1.88-2.00 (2H, m), 2.13-2.27 (2H, m), 2.37-2.66 (3H, m), 2.68-2.77 (1H, m), 2.83-2.94 (1H, m), 3.43-3.57 (1H, m), 3.67-3.76 (2H, m), 3.80-3.93 (2H, m), 4.07-4.30 (4H, m), 4.51-4.55 (1H, m), 5.09 (1H, d, J=7.9 Hz), 6.89-7.01 (3H, m).

Example 15

Ethyl (2S,3S,8R)-8-(((1S)-7-chloro-5-fluoro-2,3-dihydro-1H-inden-1-yl)sulfonyl)-2,3-bis(hydroxymethyl)-1,4-dioxaspiro[4.5]dec-6-ene-7-carboxylate Step A Ethyl (2S,3S)-8-(acetylsulfanyl)-2,3-bis((benzoyloxy)methyl)-1,4-dioxaspiro[4.5]dec-6-ene-7-carboxylate (a mixture of 2 diastereomers) (3.0 g) was separated and recovered using HPLC (column=CHIRALPAK IA, 50 mmID×500 mmL, mobile phase: hexane/ethanol=50/50) and the first peak fraction was concentrated, and ethyl (2S,3S,8R)-8-

(acetylsulfanyl)-2,3-bis((benzoyloxy)methyl)-1,4-dioxaspiro[4.5]dec-6-ene-7-carboxylate (1.36 g) was obtained as a white solid.

MS, found: 577.2.

Step B

Potassium carbonate (632 mg) was added with ice cooling to a mixture of ethyl (2S,3S,8R)-8-(acetylsulfanyl)-2,3-bis((benzoyloxy)methyl)-1,4-dioxaspiro[4.5]dec-6-ene-7-carboxylate (846 mg), methanol (8 mL) and THF (8 mL), and the mixture was stirred at the same temperature for one hour. Chlorotrimethylsilane (1.35 mL) was added to the reaction mixture, and the mixture was diluted with saturated aqueous sodium chloride solution and extracted with ethyl acetate. The liquid extract was dried with sodium sulfate, and the solvent was eliminated by distillation under reduced pressure. The residue was purified by silica gel column chromatography (ethyl acetate/hexane) and ethyl (2S,3S,8R)-2,3-bis(hydroxymethyl)-8-sulfanyl-1,4-dioxaspiro[4.5]dec-6-ene-7-carboxylate (368 mg) was obtained as a colorless oily substance.

MS=(M−H)−303.0.

Step C

DBU (94 µL) was added with ice cooling to a mixture of ethyl (2S,3S,8R)-2,3-bis(hydroxymethyl)-8-sulfanyl-1,4-dioxaspiro[4.5]dec-6-ene-7-carboxylate (173 mg), (1R)-1-bromo-7-chloro-5-fluoroindan (184 mg) and THF (2 mL), and the mixture was stirred at room temperature for 30 minutes. The reaction mixture was diluted with water, and extracted with ethyl acetate. The liquid extract was washed with saturated aqueous sodium chloride solution and was dried with sodium sulfate, and the solvent was eliminated by distillation under reduced pressure. The residue was purified by silica gel column chromatography (ethyl acetate/hexane) and ethyl (2S,3S,8R)-8-(((1S)-7-chloro-5-fluoro-2,3-dihydro-1H-inden-1-yl)sulfanyl)-2,3-bis(hydroxymethyl)-1,4-dioxaspiro[4.5]dec-6-ene-7-carboxylate (145 mg) was obtained as a colorless oily substance.

MS, found: 495.1.

Step D mCPBA (227 mg, 70%) was added with ice cooling to a mixture of ethyl (2S,3S,8R)-8-(((1S)-7-chloro-5-fluoro-2,3-dihydro-1H-inden-1-yl)sulfanyl)-2,3-bis(hydroxymethyl)-1,4-dioxaspiro[4.5]dec-6-ene-7-carboxylate (145 mg), acetonitrile (1 mL) and DMF (0.5 mL), and the mixture was stirred at room temperature for one hour. The reaction mixture was diluted with saturated aqueous sodium thiosulfate solution and extracted with ethyl acetate. The liquid extract was washed with saturated aqueous sodium chloride solution and was dried with sodium sulfate, and the solvent was eliminated by distillation under reduced pressure. The residue was purified by silica gel column chromatography (ethyl acetate/hexane) and then was separated and recovered using HPLC (column=CHIRALPAK IA, 50 mmID×500 mmL, mobile phase: hexane/ethanol=20/80) and the obtained fraction was concentrated. The residue was purified by silica gel column chromatography (ethyl acetate/hexane) and ethyl (2S,3S,8R)-8-(((1S)-7-chloro-5-fluoro-2,3-dihydro-1H-inden-1-yl)sulfonyl)-2,3-bis(hydroxymethyl)-1,4-dioxaspiro[4.5]dec-6-ene-7-carboxylate (31 mg) was obtained.

$^1$H NMR (300 MHz, CDCl$_3$) δ 1.27 (3H, t, J=7.2 Hz), 1.87-1.96 (1H, m), 2.12-2.29 (1H, m), 2.33-2.47 (1H, m), 2.49-2.66 (2H, m), 2.68-2.80 (1H, m), 2.89 (1H, dd, J=16.2, 8.7 Hz), 3.42-3.60 (1H, m), 3.67-3.78 (2H, m), 3.81-3.91 (2H, m), 3.98-4.08 (1H, m), 4.14-4.34 (3H, m), 4.52 (1H, d, J=4.9 Hz), 5.08 (1H, d, J=7.9 Hz), 6.88-6.94 (2H, m), 6.98 (1H, dd, J=8.7, 1.9 Hz).

Example 16

Ethyl (2R,3R,8R)-8-((8-chloro-1,2,3,4-tetrahydronaphthalen-1-yl)sulfonyl)-2,3-bis(hydroxymethyl)-1,4-dioxaspiro[4.5]dec-6-ene-7-carboxylate (single diastereomer, the first peak)

Example 17

Ethyl (2R,3R,8R)-8-((8-chloro-1,2,3,4-tetrahydronaphthalen-1-yl)sulfonyl)-2,3-bis(hydroxymethyl)-1,4-dioxaspiro[4.5]dec-6-ene-7-carboxylate (single diastereomer, the second peak)

Step A

A mixture of 3,4-dihydronaphthalen-1(2H)-one (5.90 g), O-methylhydroxylamine hydrochloride (5.06 g), pyridine (4 mL) and ethanol (80 mL) was heated under reflux for two hours and 30 minutes. The reaction mixture was concentrated under reduced pressure, and the residue was diluted with 1N hydrochloric acid, and extracted with ethyl acetate. The liquid extract was washed with water and saturated aqueous sodium chloride solution and was dried with magnesium sulfate, and the solvent was eliminated by distillation under reduced pressure. The residue was purified by silica gel column chromatography (ethyl acetate/hexane) and N-methoxy-3,4-dihydronaphthalen-1(2H)-imine (6.96 g) was obtained as a colorless oily substance.

$^1$H NMR (300 MHz, DMSO-d$_6$) δ 1.68-1.81 (2H, m), 2.63-2.73 (4H, m), 3.90 (3H, s), 7.14-7.23 (2H, m), 7.24-7.32 (1H, m), 7.77-7.88 (1H, m).

Step B

Palladium (II) acetate (106 mg) was added at room temperature to a mixture of N-methoxy-3,4-dihydronaphthalen-1(2H)-imine (1.65 g), N-chlorosuccinimide (1.32 g) and acetic acid (60 mL), and the mixture was stirred at 90° C. for 30 minutes. The reaction mixture was concentrated under reduced pressure, and the residue was diluted with 2N aqueous sodium hydroxide solution and extraction was performed with ethyl acetate. The liquid extract was washed with water and saturated aqueous sodium chloride solution and was dried with magnesium sulfate, and the solvent was eliminated by distillation under reduced pressure. The residue was purified by silica gel column chromatography (ethyl acetate/hexane) and 8-chloro-N-methoxy-3,4-dihydronaphthalen-1(2H)-imine (1.78 g) was obtained as a colorless oily substance.

MS: [M+H]$^+$210.1.

Step C

A mixture of 8-chloro-N-methoxy-3,4-dihydro-naphthalen-1(2H)-imine (1.78 g), 6N hydrochloric acid (30 mL) and DME (20 mL) was heated under reflux for three hours. The reaction mixture was extracted with ethyl acetate. The liquid extract was washed with water and saturated aqueous sodium chloride solution and was dried with magnesium sulfate, and the solvent was eliminated by distillation under reduced pressure. The residue was purified by silica gel column chromatography (ethyl acetate/hexane) and 8-chloro-3,4-dihydronaphthalen-1(2H)-one (1.34 g) was obtained as a colorless oily substance.

$^1$H NMR (300 MHz, DMSO-d$_6$) δ 1.94-2.07 (2H, m), 2.62 (2H, t, J=6.6 Hz), 2.96 (2H, t, J=6.2 Hz), 7.29-7.41 (2H, m), 7.43-7.51 (1H, m).

Step D

Sodium borohydride (0.63 g) was added with ice cooling to an ethanol solution (50 mL) of 8-chloro-3,4-dihydronaphthalen-1(2H)-one (2.0 g) and the mixture was stirred overnight at room temperature. About half of the solvent was eliminated by distillation under reduced pressure, and water was added to the residue, and extraction was performed with ethyl acetate. The liquid extract was washed with saturated aqueous sodium chloride solution and was dried with sodium sulfate, and the solvent was eliminated by distillation under reduced pressure. The residue was purified by silica gel column chromatography (ethyl acetate/hexane) and 8-chloro-1,2,3,4-tetrahydronaphthalen-1-ol (2.03 g) was obtained as a colorless solid.

$^1$H NMR (300 MHz, CDCl$_3$) δ 1.73-1.84 (2H, m), 1.91-2.03 (1H, m), 2.15-2.24 (1H, m), 2.36 (1H, dd, J=3.8, 1.1 Hz), 2.64-2.77 (1H, m), 2.81-2.91 (1H, m), 5.06-5.11 (1H, m), 7.02-7.07 (1H, m), 7.14 (1H, t, J=7.7 Hz), 7.21-7.25 (1H, m).

Step E 8-chloro-1,2,3,4-tetrahydronaphthalen-1-ol (2.03 g) was added at 0° C. to a diethyl ether solution (50 mL) of phosphorous tribromide (1.05 mL) and the mixture was stirred at the same temperature for two hours. The reaction mixture was diluted with water, and extracted with ethyl acetate. The liquid extract was washed with saturated aqueous sodium chloride solution and was dried with magnesium sulfate, and the solvent was eliminated by distillation under reduced pressure, and 1-bromo-8-chloro-1,2,3,4-tetrahydronaphthalene (2.54 g) was obtained as a straw-colored oily substance.

MS=(M–H)–244.8.

Step F

DBU (0.125 mL) was added with ice cooling to a mixture of ethyl (2R,3R,8R)-2,3-bis(hydroxymethyl)-8-sulfanyl-1,4-dioxaspiro[4.5]dec-6-ene-7-carboxylate (230 mg), 1-bromo-8-chloro-1,2,3,4-tetrahydronaphthalene (186 mg) and THF (6 mL), and the mixture was stirred at the same temperature for one hour. The reaction mixture was diluted with water and extracted with ethyl acetate. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and ethyl (2R,3R,8R)-8-((8-chloro-1,2,3,4-tetrahydronaphthalen-1-yl)sulfanyl)-2,3-bis(hydroxymethyl)-1,4-dioxaspiro[4.5]dec-6-ene-7-carboxylate (a mixture of 2 diastereomers) (269 mg) was obtained as a colorless solid.

MS, found: 491.2.

Step G mCPBA (302 mg, 72%) was added with ice cooling to a mixture of ethyl (2R,3R,8R)-8-((8-chloro-1,2,3,4-tetrahydronaphthalen-1-yl)sulfanyl)-2,3-bis(hydroxymethyl)-1,4-dioxaspiro[4.5]dec-6-ene-7-carboxylate (a mixture of 2 diastereomers) (269 mg), acetonitrile (3 mL) and DMF (3 mL), and the mixture was stirred overnight at room temperature. The reaction mixture was diluted with saturated aqueous sodium bicarbonate solution and extracted with ethyl acetate. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and then separated and recovered using HPLC (column=CHIRALPAK AD, 50 mmID×500 mmL, mobile phase: hexane/2-propanol=75/25). The fractions from the first peak and the second peak were each concentrated, and ethyl (2R,3R,8R)-8-((8-chloro-1,2,3,4-tetrahydronaphthalen-1-yl)sulfonyl)-2,3-bis(hydroxymethyl)-1,4-dioxaspiro[4.5]dec-6-ene-7-carboxylate (as single diastereomers) was obtained.

The first peak (yield 98.5 mg) $^1$H NMR (300 MHz, CDCl$_3$) δ 1.18 (3H, t, J=7.0 Hz), 1.57-1.67 (1H, m), 1.87-1.99 (2H, m), 2.11-2.34 (4H, m), 2.49-2.74 (4H, m), 3.05-3.16 (1H, m), 3.66-3.75 (2H, m), 3.80-3.92 (2H, m), 4.06-4.21 (4H, m), 4.56 (1H, d, J=4.2 Hz), 5.20 (1H, dd, J=7.6, 2.6 Hz), 6.96-6.98 (1H, m), 7.07-7.12 (1H, m), 7.20 (1H, t, J=7.7 Hz), 7.26-7.29 (1H, m).

The second peak (yield 45.5 mg) $^1$H NMR (300 MHz, CDCl$_3$) δ 1.37 (3H, t, J=7.2 Hz), 1.65-1.74 (1H, m), 1.84-2.10 (5H, m), 2.23-2.37 (2H, m), 2.63-2.75 (2H, m), 3.01-3.14 (1H, m), 3.66-3.75 (2H, m), 3.79-3.93 (2H, m), 4.00-4.23 (3H, m), 4.27-4.36 (2H, m), 4.87 (1H, d, J=4.9 Hz), 5.27 (1H, dd, J=6.4, 1.9 Hz), 6.93-6.97 (1H, m), 7.11 (1H, d, J=7.6 Hz), 7.18-7.24 (1H, m), 7.27-7.31 (1H, m).

Example 18

Ethyl (6R)-6-(((1S)-7-chloro-2,3-dihydro-1H-inden-1-yl)sulfonyl)cyclohex-1-ene-1-carboxylate Step A DBU (0.37 mL) was added with ice cooling to a mixture of ethyl 6-sulfanylcyclohex-1-ene-1-carboxylate (0.42 g), (1R)-1-bromo-7-chloro-5-fluoroindan (0.63 g) and THF (5 mL), and the mixture was stirred at the same temperature for one hour. The reaction mixture was diluted with water and extracted with ethyl acetate. The liquid extract was washed with saturated aqueous sodium chloride solution and was dried with sodium sulfate, and the solvent was eliminated by distillation under reduced pressure. The residue was purified by silica gel column chromatography (ethyl acetate/hexane) and then was separated and recovered using HPLC (C18, mobile phase: water/acetonitrile (system containing 0.1% TFA) and the first peak fraction was concentrated, and ethyl (6R)-6-(((1S)-7-chloro-2,3-dihydro-1H-inden-1-yl)sulfanyl)cyclohex-1-ene-1-carboxylate (270 mg) was obtained as a colorless oily substance.

MS, found: 359.0.

Step B mCPBA (494 mg, 70%) was added with ice cooling to a mixture of ethyl (6R)-6-(((1S)-7-chloro-2,3-dihydro-1H-inden-1-yl)sulfanyl)cyclohex-1-ene-1-carboxylate (270 mg) and acetonitrile (3 mL), and the mixture was stirred at room temperature for one hour. The reaction mixture was diluted with saturated aqueous sodium thiosulfate solution and extracted with ethyl acetate. The liquid extract was washed with saturated aqueous sodium bicarbonate solution (twice) and saturated aqueous sodium chloride solution and then was dried with magnesium sulfate, and the solvent was eliminated by distillation under reduced pressure. The residue was purified by silica gel column chromatography (ethyl acetate/hexane) and then recrystallized from ethyl acetate/IPE. The obtained solids were separated and recovered using SFC (column=CHIRALPAK AD-H, 20 mmID×250 mmL, mobile phase: carbon dioxide/2-propanol=90/10) and the obtained fraction was concentrated under reduced pressure, and ethyl (6R)-6-(((1S)-7-chloro-2,3-dihydro-1H-inden-1-yl)sulfonyl)cyclohex-1-ene-1-carboxylate (176 mg) was obtained as a pale-brown solid.

$^1$H NMR (300 MHz, CDCl$_3$) δ 1.25 (3H, t, J=7.2 Hz), 1.64-1.84 (2H, m), 1.96-2.34 (2H, m), 2.39-2.67 (3H, m), 2.76 (1H, dd, J=14.2, 7.4 Hz), 2.89 (1H, dd, J=16.1, 8.9 Hz), 3.43-3.61 (1H, m), 4.09-4.30 (2H, m), 4.59 (1H, d, J=5.7 Hz), 5.11 (1H, d, J=7.9 Hz), 7.14-7.25 (3H, m), 7.39 (1H, t, J=4.0 Hz).

Example 19

Ethyl (2S,3S,8R)-8-(((1S)-8-chloro-1,2,3,4-tetrahydronaphthalen-1-yl)sulfonyl)-2,3-bis(hydroxymethyl)-1,4-dioxaspiro[4.5]dec-6-ene-7-carboxylate Step A Under a nitrogen atmosphere, borane dimethyl sulfide complex (2.91 mL) was added at −78° C. to a mixture of (3aR)-1-methyl-3,3-diphenyltetrahydro-3H-pyrrolo[1,2-c][1,3,2]oxazaborole (0.61 g), 8-chloro-3,4-dihydronaphthalen-1(2H)-one (1.0 g), and THF (30 mL), and it was stirred overnight while warming to room temperature. Methanol was added with ice cooling to the reaction mixture, and the mixture concentrated down and the residue was purified by silica gel column chromatography (ethyl acetate/hexane). The obtained solids were recrystallized from toluene/hexane, and (1S)-8-chloro-1,2,3,4-tetrahydronaphthalen-1-ol (0.69 g) was obtained as a colorless solid.

$^{1}$H NMR (300 MHz, CDCl$_{3}$) δ 1.73-1.84 (2H, m), 1.91-2.04 (1H, m), 2.15-2.24 (1H, m), 2.36 (1H, dd, J=3.8, 1.1 Hz), 2.64-2.77 (1H, m), 2.81-2.91 (1H, m), 5.06-5.11 (1H, m), 7.03-7.07 (1H, m), 7.14 (1H, t, J=7.6 Hz), 7.21-7.25 (1H, m).

Step B

Phosphorous tribromide (118 μL) was added at −10° C. to a diethyl ether solution (4 mL) of (1S)-8-chloro-1,2,3,4-tetrahydronaphthalen-1-ol (230 mg) and the mixture was stirred at the same temperature for 30 minutes. The reaction mixture was diluted with saturated aqueous sodium bicarbonate solution and extracted with ethyl acetate. The liquid extract was washed with saturated aqueous sodium chloride solution and was dried with sodium sulfate, and the solvent was eliminated by distillation under reduced pressure, and (1R)-1-bromo-8-chloro-1,2,3,4-tetrahydronaphthalene (196 mg) was obtained as a brown oily substance.

$^{1}$H NMR (300 MHz, CDCl$_{3}$) δ 1.88-2.02 (1H, m), 2.03-2.13 (1H, m), 2.23-2.41 (1H, m), 2.41-2.53 (1H, m), 2.79-3.07 (2H, m), 5.68 (1H, brs), 7.01 (1H, d, J=7.6 Hz), 7.10-7.18 (1H, m), 7.19-7.25 (1H, m).

Step C

DBU (0.15 mL) was added with ice cooling to a mixture of ethyl (2S,3S,8R)-2,3-bis(hydroxymethyl)-8-sulfanyl-1,4-dioxaspiro[4.5]dec-6-ene-7-carboxylate (368 mg), (1R)-1-bromo-8-chloro-1,2,3,4-tetrahydronaphthalene (196 mg) and THF (3 mL), and the mixture was stirred at the same temperature for one hour. The reaction mixture was diluted with water and extracted with ethyl acetate. The liquid extract was dried with sodium sulfate, and the solvent was eliminated by distillation under reduced pressure. The residue was purified by silica gel column chromatography (ethyl acetate/hexane) and ethyl (2S,3S,8R)-8-(((1S)-8-chloro-1,2,3,4-tetrahydronaphthalen-1-yl)sulfanyl)-2,3-bis(hydroxymethyl)-1,4-dioxaspiro[4.5]dec-6-ene-7-carboxylate (279 mg) was obtained as a colorless oily substance.

MS, found: 491.2.

Step D mCPBA (367 mg, 70%) was added with ice cooling to a mixture of ethyl (2S,3S,8R)-8-(((1S)-8-chloro-1,2,3,4-tetrahydronaphthalen-1-yl)sulfanyl)-2,3-bis(hydroxymethyl)-1,4-dioxaspiro[4.5]dec-6-ene-7-carboxylate (279 mg) and acetonitrile (5 mL), and the mixture was stirred at room temperature for three hours. The reaction mixture was diluted with saturated aqueous sodium thiosulfate solution and extracted with ethyl acetate. The liquid extract was washed with saturated aqueous sodium chloride solution, dried with magnesium sulfate, and the solvent was eliminated by distillation under reduced pressure. The residue was purified by silica gel column chromatography (ethyl acetate/hexane) and then separated and recovered using SFC (column=CHIRALCEL OJ-H, 20 mmID×250 mmL, mobile phase: carbon dioxide/methanol=86/14) and the obtained fraction was concentrated under reduced pressure. The residue was crystallized from ethyl acetate/heptane, and ethyl (2S,3S,8R)-8-(((1S)-8-chloro-1,2,3,4-tetrahydronaphthalen-1-yl)sulfonyl)-2,3-bis(hydroxymethyl)-1,4-dioxaspiro[4.5]dec-6-ene-7-carboxylate (47 mg) was obtained.

$^{1}$H NMR (300 MHz, CDCl$_{3}$) δ 1.18 (3H, t, J=7.2 Hz), 1.57-1.70 (1H, m), 1.84-1.97 (2H, m), 2.00-2.09 (1H, m), 2.09-2.39 (3H, m), 2.46-2.55 (1H, m), 2.56-2.74 (3H, m), 3.02-3.18 (1H, m), 3.64-3.77 (2H, m), 3.80-3.93 (2H, m), 3.97-4.24 (4H, m), 4.55 (1H, d, J=5.3 Hz), 5.19 (1H, dd, J=7.6, 2.3 Hz), 6.86-6.92 (1H, m), 7.06-7.13 (1H, m), 7.16-7.24 (1H, m), 7.28 (1H, s).

Example 20

Ethyl 3-(((1S)-7-chloro-2,3-dihydro-1H-inden-1-yl)sulfonyl)-3,6-dihydro-2H-pyran-4-carboxylate (a single diastereomer)

Step A

While keeping the internal temperature at 20° C. or less using ice cooling, (3R,4S)-tetrahydrofuran-3,4-diol (45.0 g) was added dropwise to an aqueous solution (220 mL) of sodium periodate (97.0 g), and the mixture was then stirred overnight at room temperature. Sodium bicarbonate (7.26 g) and ethyl(diethoxyphosphoryl)acetate (60.6 mL) were added at room temperature to the reaction mixture, and the mixture was stirred at the same temperature for three hours. Sodium bicarbonate (84.0 g) was added to the reaction mixture, and the mixture was stirred overnight at an internal temperature of 50° C. The reaction mixture was cooled to room temperature, and then the solids were eliminated by filtration. The solids were washed with THF, and the washings were combined with the filtrate. Sodium chloride was added to the mixture and extraction performed with ethyl acetate. The aqueous phase was extracted twice further with an ethyl acetate/THF liquid mixture, and the extracts were combined and dried with magnesium sulfate, and the solvent was eliminated by distillation under reduced pressure. The residue was purified by silica gel column chromatography (ethyl acetate/hexane) and ethyl 3-hydroxy-3,6-dihydro-2H-pyran-4-carboxylate (25.8 g) was obtained as a straw-colored oily substance.

$^{1}$H NMR (300 MHz, CDCl$_{3}$) δ 1.33 (3H, t, J=7.2 Hz), 2.79 (1H, d, J=4.9 Hz), 3.72 (1H, dd, J=11.9, 3.2 Hz), 3.95 (1H, dd, J=11.7, 3.0 Hz), 4.18-4.43 (5H, m), 7.04-7.08 (1H, m).

Step B

Triethylamine (31.2 mL) was added with ice cooling to a THF (300 mL) solution of ethyl 3-hydroxy-3,6-dihydro-2H-pyran-4-carboxylate (25.8 g) and the mixture was stirred at the same temperature for ten minutes. Methanesulfonyl chloride (14.5 mL) was added to the reaction mixture and the mixture was stirred at the same temperature for 30 minutes. The reaction mixture was diluted with ice cooled 1N hydrochloric acid and extracted with ethyl acetate. The liquid extract was washed with saturated aqueous sodium chloride solution and was dried with sodium sulfate, and the solvent was eliminated by distillation under reduced pressure. To a mixture of the residue and toluene (400 mL), were successively added thioacetic acid (12.6 mL) and triethylamine (26.7 mL) under ice cooling and the mixture was stirred at the same temperature for 30 minutes. The reaction mixture was diluted with 1N hydrochloric acid and extracted with ethyl acetate. The liquid extract was washed with saturated aqueous sodium chloride solution and was dried with magnesium sulfate, and the solvent was eliminated by distillation under reduced pressure. The residue was purified by silica gel column chromatography (ethyl acetate/hexane) and ethyl 3-(acetylsulfanyl)-3,6-dihydro-2H-pyran-4-carboxylate (24.7 g) was obtained as a straw-colored oily substance.

$^1$H NMR (300 MHz, CDCl$_3$) δ 1.28 (3H, t, J=7.0 Hz), 2.34 (3H, s), 3.85 (1H, dd, J=11.9, 2.5 Hz), 4.00 (1H, dd, J=12.1, 1.1 Hz), 4.17-4.31 (3H, m), 4.37-4.46 (1H, m), 4.52 (1H, brs), 7.05-7.09 (1H, m).

Step C 4N hydrochloric acid (ethyl acetate solution, 70 mL) was added at room temperature to an ethanol solution (70 mL) of ethyl 3-(acetylsulfanyl)-3,6-dihydro-2H-pyran-4-carboxylate (24.7 g) and the mixture was stirred at 45° C. for 16 hours. The reaction mixture was concentrated under reduced pressure, and the residue was purified by silica gel column chromatography (ethyl acetate/hexane) and ethyl 3-sulfanyl-3,6-dihydro-2H-pyran-4-carboxylate (19.5 g) was obtained as a straw-colored oily substance.

$^1$H NMR (300 MHz, CDCl$_3$) δ 1.32 (3H, t, J=7.2 Hz), 2.23 (1H, d, J=9.1 Hz), 3.67-3.75 (1H, m), 3.85-3.93 (1H, m), 4.01 (1H, dd, J=11.7, 1.9 Hz), 4.22-4.32 (3H, m), 4.37-4.47 (1H, m), 6.82-6.86 (1H, m).

Step D

DBU (0.34 mL) was added with ice cooling to a mixture of ethyl 3-sulfanyl-3,6-dihydro-2H-pyran-4-carboxylate (0.43 g), (1R)-1-bromo-7-chloroindane (0.63 g) and THF (5 mL), and the mixture was stirred at the same temperature for one hour. The reaction mixture was diluted with water and extracted with ethyl acetate. The liquid extract was washed with saturated aqueous sodium chloride solution and was dried with sodium sulfate, and the solvent was eliminated by distillation under reduced pressure. The residue was purified by silica gel column chromatography (ethyl acetate/hexane) and ethyl 3-(((1S)-7-chloro-2,3-dihydro-1H-inden-1-yl)sulfanyl)-3,6-dihydro-2H-pyran-4-carboxylate (a mixture of 2 diastereomers) (0.32 g) was obtained as a colorless oily substance.

$^1$H NMR (300 MHz, CDCl$_3$) δ 1.23-1.40 (3H, m), 2.23-2.60 (2H, m), 2.77-2.96 (1H, m), 3.20-3.42 (1H, m), 3.70 (0.6H, brs), 3.75-3.92 (1.4H, m), 4.05 (0.6H, dd, J=11.7, 1.5 Hz), 4.16-4.33 (3.4H, m), 4.34-4.47 (1H, m), 4.53 (0.4H, d, J=6.4 Hz), 4.79 (0.6H, d, J=6.8 Hz), 6.85-6.92 (0.6H, m), 6.94-6.99 (0.4H, m), 7.06-7.21 (3H, m).

Step E mCPBA (0.58 g, 70%) was added with ice cooling to a mixture of ethyl 3-(((1S)-7-chloro-2,3-dihydro-1H-inden-1-yl)sulfanyl)-3,6-dihydro-2H-pyran-4-carboxylate (a mixture of 2 diastereomers) (0.32 g) and acetonitrile (3 mL), and the mixture was stirred at room temperature for one hour. The reaction mixture was diluted with saturated aqueous sodium thiosulfate solution and extracted with ethyl acetate. The liquid extract was washed with saturated aqueous sodium bicarbonate solution (twice) and saturated aqueous sodium chloride solution and was dried with sodium sulfate, and the solvent was eliminated by distillation under reduced pressure. The residue was purified by silica gel column chromatography (ethyl acetate/hexane) and the high polarity fraction was concentrated under reduced pressure. Of the obtained residue, 100 mg was separated and recovered using SFC (column=CHIRALPAK AD-H, 20 mmID×250 mmL, mobile phase: carbon dioxide/methanol=77/23) and the first peak fraction was concentrated down under reduced pressure. The residue was purified by silica gel column chromatography (ethyl acetate/hexane) and ethyl 3-(((1S)-7-chloro-2,3-dihydro-1H-inden-1-yl)sulfonyl)-3,6-dihydro-2H-pyran-4-carboxylate (a single diastereomer) (36 mg) was obtained.

$^1$H NMR (300 MHz, CDCl$_3$) δ 1.31 (3H, t, J=7.2 Hz), 2.35-2.52 (1H, m), 2.67 (1H, dd, J=14.2, 7.4 Hz), 2.87 (1H, dd, J=15.9, 8.7 Hz), 3.40-3.57 (1H, m), 3.79 (1H, dd, J=12.7, 3.2 Hz), 4.23-4.41 (4H, m), 4.52-4.63 (1H, m), 4.80-4.88 (1H, m), 5.24 (1H, d, J=7.6 Hz), 7.15-7.25 (4H, m).

Example 21

Ethyl (2R,3R,8R)-8-(((1S)-7-chloro-2,3-dihydro-1H-inden-1-yl)sulfonyl)-2,3-bis(methoxymethyl)-1,4-dioxaspiro[4.5]dec-6-ene-7-carboxylate Step A Sodium hydride (1.26 g, 60% oil) was added with ice cooling to a mixture of ethyl (2R,3R,8R)-8-(((1S)-7-chloro-2,3-dihydro-1H-inden-1-yl)sulfanyl)-2,3-bis(hydroxymethyl)-1,4-dioxaspiro[4.5]dec-6-ene-7-carboxylate (5.72 g), iodomethane (7.14 g) and DMF (50 mL), and the mixture was stirred at the same temperature for one hour. The reaction mixture was diluted with water and extracted with ethyl acetate. The liquid extract was washed with water and saturated aqueous sodium chloride solution and was washed with magnesium sulfate, and the solvent was eliminated by distillation under reduced pressure. The residue was purified by silica gel column chromatography (ethyl acetate/hexane) and ethyl (2R,3R,8R)-8-(((1S)-7-chloro-2,3-dihydro-1H-inden-1-yl)sulfanyl)-2,3-bis(methoxymethyl)-1,4-dioxaspiro[4.5]dec-6-ene-7-carboxylate (5.91 g) was obtained as a straw-colored oily substance.

MS, found: 532.2.

Step B mCPBA (7.15 g, 65%) was added with ice cooling to a mixture of ethyl (2R,3R,8R)-8-(((1S)-7-chloro-2,3-dihydro-1H-inden-1-yl)sulfanyl)-2,3-bis(methoxymethyl)-1,4-dioxaspiro[4.5]dec-6-ene-7-carboxylate (5.91 g), DMF (50 mL) and acetonitrile (50 mL), and the mixture stirred overnight at room temperature. The reaction mixture was diluted with saturated aqueous sodium bicarbonate solution and extracted with ethyl acetate. The liquid extract was washed with water and saturated aqueous sodium chloride solution and was dried with magnesium sulfate, and the solvent was eliminated by distillation under reduced pressure. The residue was purified by silica gel column chromatography (ethyl acetate/hexane) and was crystallized from ethanol/hexane, and the solids were recovered by filtration. The obtained solids were recrystallized from ethyl acetate/heptane, and ethyl (2R,3R,8R)-8-(((1S)-7-chloro-2,3-dihydro-1H-inden-1-yl)sulfonyl)-2,3-bis(methoxymethyl)-1,4-dioxaspiro[4.5]dec-6-ene-7-carboxylate (3.47 g) was obtained as a white solid.

¹H NMR (300 MHz, CDCl₃) δ 1.19 (3H, t, J=7.2 Hz), 1.85-2.01 (1H, m), 2.15-2.35 (1H, m), 2.39-2.62 (3H, m), 2.76 (1H, dd, J=14.4, 7.6 Hz), 2.88 (1H, dd, J=16.2, 8.7 Hz), 3.40 (3H, s), 3.42 (3H, s), 3.44-3.66 (5H, m), 3.98-4.07 (1H, m), 4.08-4.27 (3H, m), 4.49-4.58 (1H, m), 5.07 (1H, d, J=8.3 Hz), 7.05 (1H, s), 7.13-7.25 (3H, m).

According to the methods shown in the Examples or methods analogous thereto, the compounds of Examples 9-13 in following tables were produced. The compounds of Examples are shown in the following Table. MS in the table means actual value.

TABLE 1

| Example number | IUPAC Name | Structure | MS |
| --- | --- | --- | --- |
| 1 | Ethyl 6-((4-chloro-2,3-dihydro-1H-inden-1-yl)sulfonyl)cyclohex-1-ene-1-carboxylate | 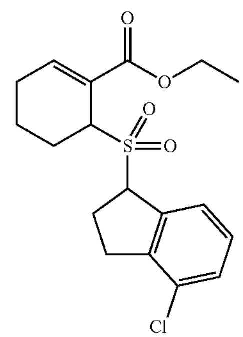 [SMILES: CCOC(=O)C1=CCCCC1S(=O)(=O)C1CCc2c(Cl)cccc21] | 368.9 |
| 2 | Ethyl (2R,3R)-8-((4-chloro-2,3-dihydro-1H-inden-1-yl)sulfonyl)-2,3-bis(hydroxymethyl)-1,4-diazaspiro[4.5]dec-6-ene-7-carboxylate | 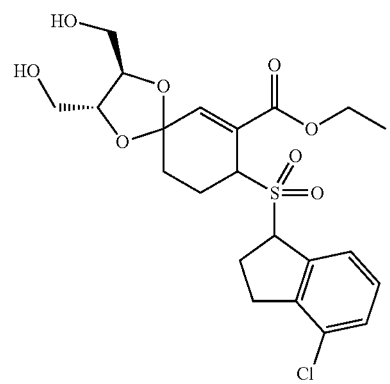 [SMILES: CCOC(=O)C1=CC2(CCC1S(=O)(=O)C1CCc3c(Cl)cccc31)O[C@H](CO)[C@@H](CO)O2] | 484.9 |
| 3 | Ethyl (2S,3S)-8-((4-chloro-2,3-dihydro-1H-inden-1-yl)sulfonyl)-2,3-bis(hydroxymethyl)-1,4-dioxospiro[4.5]dec-6-ene-7-carboxylate | 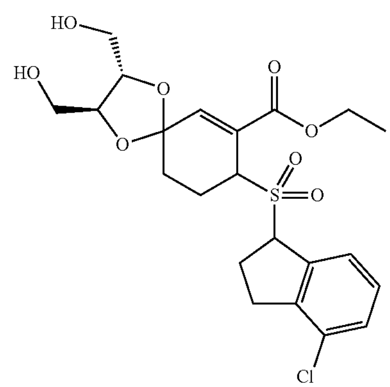 [SMILES: CCOC(=O)C1=CC2(CCC1S(=O)(=O)C1CCc3c(Cl)cccc31)O[C@@H](CO)[C@H](CO)O2] | 485.1 |
| 4 | Ethyl 6-((7-chloro-2,3-dihydro-1H-inden-1-yl)sulfonyl)-3-hydroxycyclohex-1-ene-1-carboxylate | 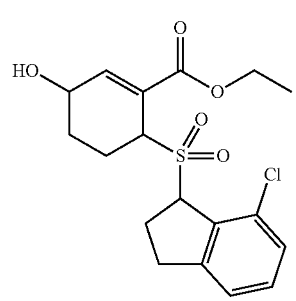 [SMILES: CCOC(=O)C1=CC(O)CCC1S(=O)(=O)C1CCc2cccc(Cl)c21] | 384.9 |

TABLE 1-continued

| Example number | IUPAC Name | Structure | MS |
|---|---|---|---|
| 5 | Ethyl 6-((7-chloro-2,3-dihydro-1H-inden-1-yl)sulfonyl)-3-hydroxycyclohex-1-ene-1-carboxylate | 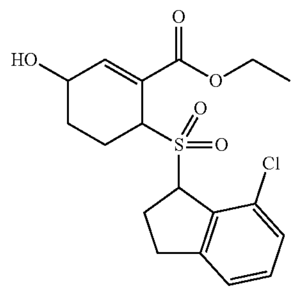 [SMILES: CCOC(=O)C1=CC(O)CCC1S(=O)(=O)C1CCc2cccc(Cl)c21] | 384.9 |
| 6 | Ethyl (2R, 3R, 8R)-8-(((1S)-7-chloro-2,3-dihydro-1H-inden-1-yl)sulfonyl)-2,3-bis(hydroxymethyl)-1,4-dioxaspiro[4.5]dec-6-ene-7-carboxylate | 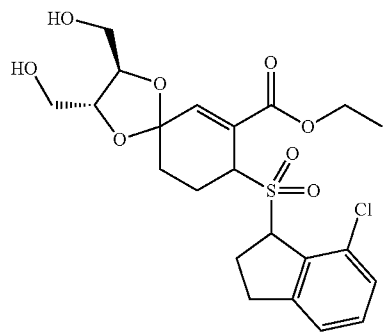 [SMILES: CCOC(=O)C1=CC2(CCC1S(=O)(=O)C1CCc3cccc(Cl)c31)O[C@H](CO)[C@@H](CO)O2] | 485.0 |
| 7 | Ethyl (2R, 3S, 8R)-8-(((1S)-7-chloro-2,3-dihydro-1H-inden-1-yl)sulfonyl)-2,3-bis(hydroxymethyl)-1,4-dioxaspiro[4.5]dec-6-ene-7-carboxylate | 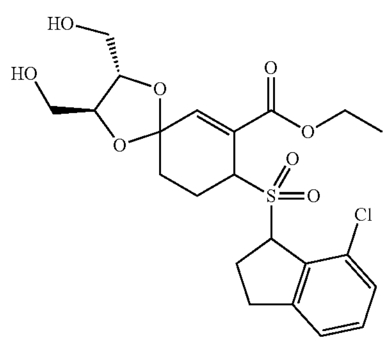 [SMILES: CCOC(=O)C1=CC2(CCC1S(=O)(=O)C1CCc3cccc(Cl)c31)O[C@@H](CO)[C@H](CO)O2] | 485.0 |
| 8 | (1-methylcyclopropyl)methyl (2S, 3S)-8-((7-chloro-2,3-dihydro-1H-inden-1-yl)sulfonyl)-2,3-bis(hydroxymethyl)-1,4-dioxaspiro[4.5]dec-6-ene-7-carboxylate | 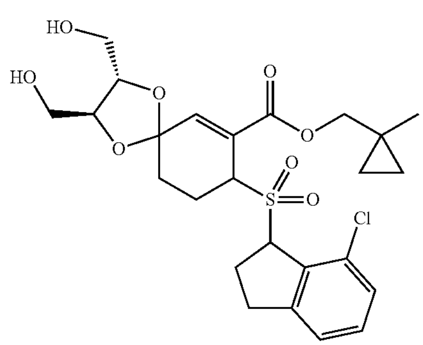 [SMILES: CC1(COC(=O)C2=CC3(CCC2S(=O)(=O)C2CCc4cccc(Cl)c42)O[C@@H](CO)[C@H](CO)O3)CC1] | 525.1 |

TABLE 1-continued

| Example number | IUPAC Name | Structure | MS |
|---|---|---|---|
| 9 | Ethyl (2S, 3S)-8-((7-chloro-4-fluoro-2,3-dihydro-1H-inden-1-yl)sulfonyl)-2,3-bis(hydroxymethyl)-1,4-dioxaspiro[4.5]dec-6-ene-7-carboxylate | 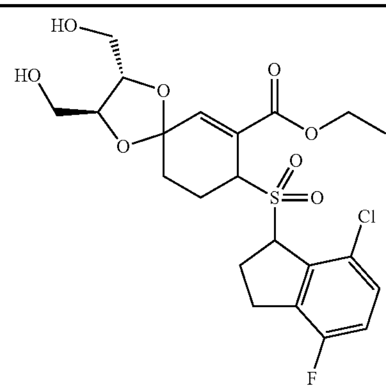 | 503.1 |
| 10 | Ethyl (2S, 3S)-8-((7-chloro-6-fluoro-2,3-dihydro-1H-inden-1-yl)sulfonyl)-2,3-bis(hydroxymethyl)-1,3-dioxaspiro[4.5]dec-6-ene-7-carboxylate | 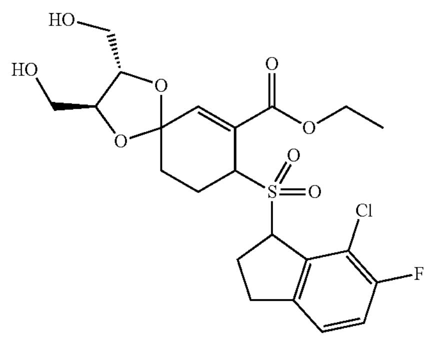 [SMILES: CCOC(=O)C1=CC2(CCC1S(=O)(=O)C1CCc3ccc(F)c(Cl)c31)O[C@@H](CO)[C@H](CO)O2] | 503.0 |
| 11 | Ethyl (2S, 3S)-8-((7-bromo-5-fluoro-2,3-dihydro-1H-inden-1-yl)sulfonyl)-2,3-bis(hydroxymethyl)-1,4-dioxaspiro[4.5]dec-6-ene-7-carboxylate | 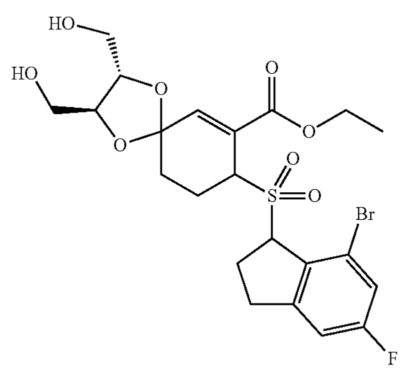 [SMILES: CCOC(=O)C1=CC2(CCC1S(=O)(=O)C1CCc3cc(F)cc(Br)c31)O[C@@H](CO)[C@H](CO)O2] | 546.9 |
| 12 | Ethyl (2S, 3S)-8-((7-bromo-2,3-dihydro-1H-inden-1-yl)sulfonyl)-2,3-bis(hydroxymethyl)-1,4-dioxaspiro[4.5]dec-6-ene-7-carboxylate | 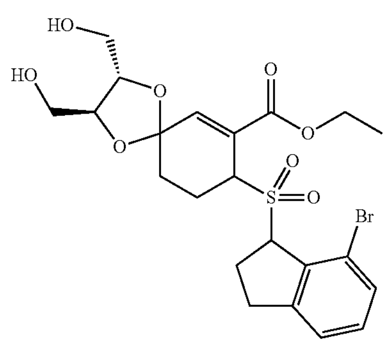 [SMILES: CCOC(=O)C1=CC2(CCC1S(=O)(=O)C1CCc3cccc(Br)c31)O[C@@H](CO)[C@H](CO)O2] | 531.0 |

TABLE 1-continued

| Example number | IUPAC Name | Structure | MS |
|---|---|---|---|
| 13 | Ethyl (2S, 3S)-2,3-bis(hydroxymethyl)-8-(((7-methyl-2,3-dihydro-1H-inden-1-yl)sulfonyl)-1,4-dioxaspiro[4.5]dec-6-ene-7-carboxylate | 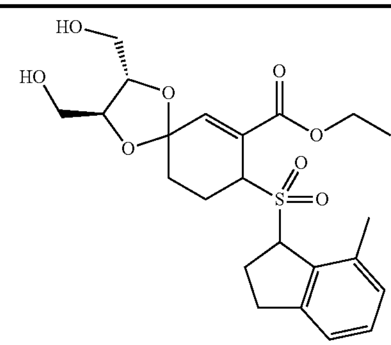 | |
| 14 | Ethyl (2R, 3R, 8R)-8-(((1S)-7-chloro-5-fluoro-2,3-dihydro-1H-inden-1-yl)sulfonyl)-2,3-bis(hydroxymethyl)-1,4-dioxaspiro[4.5]dec-6-ene-7-carboxylate | 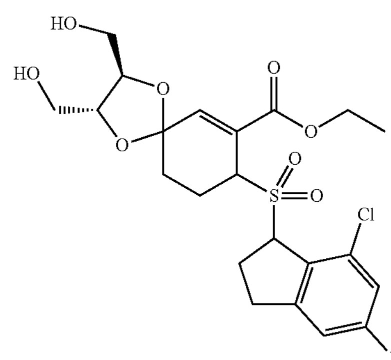 | 503.0 |
| 15 | Ethyl (2R, 3R, 8R)-8-(((1S)-7-chloro-5-fluoro-2,3-dihydro-1H-inden-1-yl)sulfonyl)-2,3-bis(hydroxymethyl)-1,4-dioxaspiro[4.5]dec-6-ene-7-carboxylate | 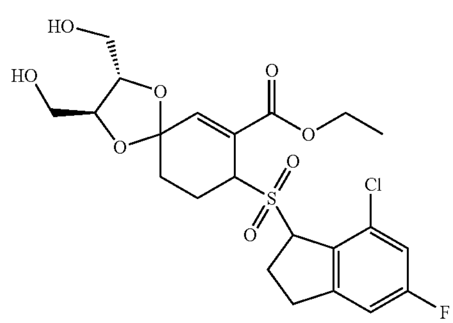 [SMILES: CCOC(=O)C1=CC2(CCC1S(=O)(=O)C1CCc3cc(F)cc(Cl)c31)O[C@@H](CO)[C@H](CO)O2] | 503.0 |
| 16 | Ethyl (2R, 3R, 8R)-8-(8-chloro-1,2,3,4-tetrahydronaphthalen-1-yl)sulfonyl)-2,3-bis(hydroxymethyl)-1,4-dioxaspiro[4.5]dec-6-ene-7-carboxylate | 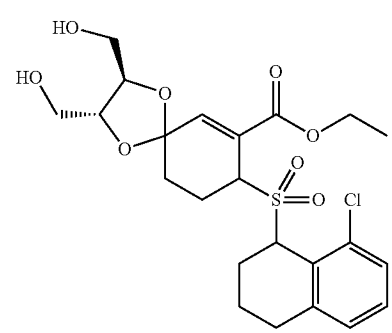 [SMILES: CCOC(=O)C1=CC2(CCC1S(=O)(=O)C1CCCc3cccc(Cl)c31)O[C@H](CO)[C@@H](CO)O2] | 499.1 |

TABLE 1-continued

| Example number | IUPAC Name | Structure | MS |
|---|---|---|---|
| 17 | Ethyl (2R, 3R, 8R)-8-(8-chloro-1,2,3,4-tetrahydronaphthalen-1-yl)sulfonyl)-2,3-bis(hydroxymethyl)-1,4-dioxaspiro[4.5]dec-6-ene-7-carboxylate | 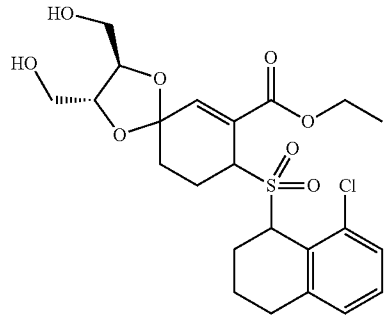 [SMILES: CCOC(=O)C1=CC2(CCC1S(=O)(=O)C1CCCc3cccc(Cl)c31)O[C@H](CO)[C@@H](CO)O2] | 499.0 |
| 18 | Ethyl (6R)-6-(((1S)-7-chloro-2,3-dihydro-1H-inden-1-yl)sulfonyl)cyclohex-1-ene-1-carboxylate | 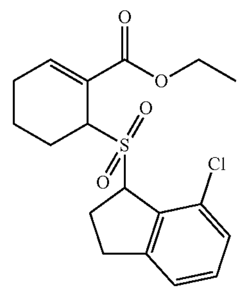 [SMILES: CCOC(=O)C1=CCCCC1S(=O)(=O)C1CCc2cccc(Cl)c21] | 369.1 |
| 19 | Ethy (2S, 3S, 8R)-8-(((1S)-8-chloro-1,2,3,4-tetrahydronaphthalen-1-yl)sulfonyl)-2,3-bis(hydroxymethyl)-1,4-dioxaspiro[4.5]dec-6-ene-7-carboxylate | 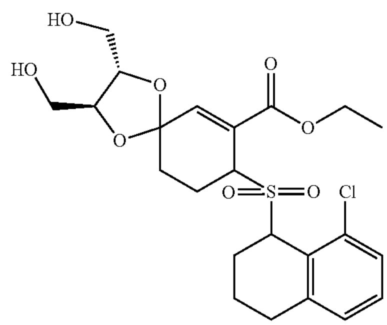 [SMILES: CCOC(=O)C1=CC2(CCC1S(=O)(=O)C1CCCc3cccc(Cl)c31)O[C@@H](CO)[C@H](CO)O2] | 499.1 |
| 20 | Ethyl 3-(((1S)-7-chloro-2,3-dihydro-1H-inden-1-yl)sulfonyl)-3,6-dihydro-2H-pyran-4-carboxylate | 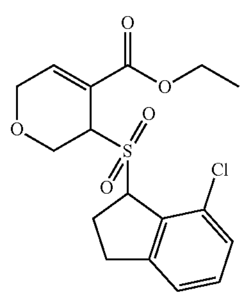 [SMILES: CCOC(=O)C1=CCOCC1S(=O)(=O)C1CCc2cccc(Cl)c21] | 371.0 |
| 21 | Ethyl (2R, 3R, 8R)-8-(((1S)-7-chloro-2,3-dihydro-1H-inden-1-yl)sulfonyl)-2,3-bis(methoxymethyl)-1,4-dioxaspiro[4.5]dec-6-ene-7-carboxylate | 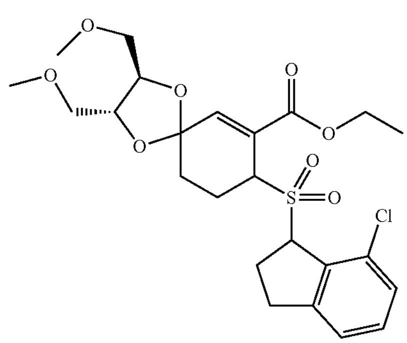 [SMILES: CCOC(=O)C1=CC2(CCC1S(=O)(=O)C1CCc3cccc(Cl)c31)O[C@H](COC)[C@@H](COC)O2] | 515.1 |

The NMR of the compound of Example 13 is shown below.

$^1$H NMR (300 MHz, CDCl$_3$) δ 1.28-1.37 (3H, m), 2.07-2.30 (2H, m), 2.33-2.43 (3H, m), 2.46-2.67 (4H, m), 2.76-2.92 (2H, m), 3.33-3.47 (1H, m), 3.61-3.86 (4H, m), 3.98-4.11 (1H, m), 4.15-4.37 (4H, m), 4.64-4.77 (1H, m), 4.78-4.90 (0.25H, m), 5.03-5.09 (0.5H, m), 5.30 (0.25H, d, J=7.9 Hz), 7.00-7.25 (4H, m).

Test Example 1: Inhibitory Effect with Respect to NO Production

The inhibitory effect on TLR4 was determined using the inhibition rate due to the test compound with respect to NO production as a result of addition of lipopolysaccharide (LPS) using murine macrophage cell line RAW264.7. The cells were adjusted to 2×10$^6$ cells/mL using RPM1-1640 culture medium (phenol red free) supplemented with 10% inactivated bovine fetal serum, and were plated on 384 well plate so as to contain 6×10$^4$ cells/30 μL per well. Thereafter the cells were cultured at 37° C. overnight under 5% CO$_2$/95% air. The test compound dissolved in DMSO was diluted 200 times using RPM1-1640 culture medium and adjusted so as to form a compound concentration of 500 nM. The prepared test compound 10 μL (final concentration 100 nM) was added to the cells, and LPS (Sigma) and mouse interferon γ (Wako Pure Chemicals) were added in amounts of 10 μL so as to form final concentrations of 1.25 ng/mL and 0.2 ng/mL respectively. The cells were further cultured overnight, and then the nitrite ion (stable NO metabolite) concentration in the culture supernatant was measured as an index of NO production. The nitrite ion concentration was assayed by adding 10 μL of 20 μg/mL 2,3-diamino naphthalene (DAN) dissolved in 0.2N HCl to 20 μL culture supernatant, incubating at room temperature for ten minutes, and then adding 10 μL of 0.5N NaOH, and measuring the fluorescent value at 460 nm (excitation wavelength 355 nm) using an EnVision plate reader (Perkin Elmer). The NO production inhibition rate (%) was calculated using the value without the addition of stimulating agent as control of 100% inhibition, and the value without the addition of the compound as control of 0% inhibition. The results thereof are shown in Table 2.

TABLE 2

| Compound No. | NO production inhibitory effect at 100 nM (% inhibition) |
| --- | --- |
| 1 | 96 |
| 2 | 99 |
| 3 | 110 |
| 4 | 110 |
| 5 | 100 |
| 6 | 103 |
| 7 | 105 |
| 8 | 99 |
| 9 | 110 |
| 10 | 100 |
| 11 | 110 |
| 12 | 100 |
| 13 | 100 |
| 14 | 107 |
| 15 | 106 |
| 16 | 108 |
| 17 | 86 |
| 18 | 104 |
| 19 | 107 |
| 20 | 104 |
| 21 | 112 |

Test Example 2: Effect with Respect to Blood TNF-α Concentration Elevation by LPS Stimulation Various kinds of cytokines are produced in vivo accompanying inflammatory response and abnormal immunity or the like. Therefore, the action of test compound with respect to blood TNFα concentration rise was investigated using laboratory animals.

Female BALB/c mice (6 weeks old) were purchased, and, after preliminary rearing for about 1 week, the mice were divided into groups of four animals. The test compound was dissolved in 10% captisol aqueous solution and was intravenously administered to the test group at a dose of 3 mg/kg. Solvent was administered to control group in the same way. LPS (5 mg/kg) was administered intraperitoneally to the test group and the control group one hour after the administration of the test compound or solvent, and blood was sampled one hour later. The serum was separated from the obtained blood, and the TNFα concentration in the serum was measured using an assay kit made by R&D Systems Inc. The inhibition rates of the test group with respect to the control group are shown in Table 3.

TABLE 3

| Compound No. | Blood TNFα inhibition rate (% inhibition) |
| --- | --- |
| 6 | 93.1 |

Test Example 3: Action on Liver Injury by Galactosamine/LPS Stimulation

The action on liver injury by Galactosamine/LPS stimulation was evaluated by elevation of blood alanine transaminase (ALT) amount as an index. Galactosamine (700 mg/kg) and LPS (5 μg/kg) were administered intraperitoneally to BALB/c mice (female, 7 weeks old, Japan Charles River). After 8 hr, the blood was collected in the presence of heparin. The obtained blood was centrifuged (4° C., 10000× rpm, 10 min), and the blood plasma was collected, and the ALT amount in the blood plasma was measured by 7180 type Hitachi automated analytical apparatus (Hitachi High-Technologies Corporation). Compound 6 was dissolved in 10% captisol solution (0.3, 1, 3 mg/kg), and the solution was administered intravenously to the mice in the tail vein 1 hr before Galactosamine/LPS administration. The mean±standard errors of the ALT amount in the blood plasma of each group were shown in Table 4.

TABLE 4

| | Non-stimu-lation | Galactosamine/LPS stimulation | | | |
| --- | --- | --- | --- | --- | --- |
| | | | Compound No. 6 (mg/kg) | | |
| | Vehicle | Vehicle | 0.3 | 1 | 3 |
| ALT (IU/L) | 83 ± 4 | 1021 ± 185### | 570 ± 94 | 361 ± 60** | 104 ± 10*** |

Sample number = 5 (non-stimulation group) or 10 (Galactosamine/LPS stimulation group),
P < 0.001 vs. Non-stimulation/Vehicle group (Aspin-Welch t test),
P < 0.005, *P < 0.0005 vs. Galactosamine/LPS stimulation-Vehicle group (One-tailed Shirley-Williams test)

As shown in Table 4, Compound 6 (0.3, 1, 3 mg/kg) dose-dependently and significantly inhibited the increase in the ALT amount in the blood plasma due to Galactosamine/LPS stimulation. As is clear from the results, it is suggested that Compound 6 has effect on the prophylaxis or treatment of liver injury.

Test Example 4: Inhibitory Effect on TNFα Production from HMGB-1 Stimulated-Human Kupffer Cell TLR4 signal inhibitory activity in human Kupffer cell was evaluated as an inhibition rate of the test compound for TNFα produced by addition of HMGB-1 (SHINO-TEST), using human primary Kupffer cells (Cat# HUKCCS, Lot#HK8226) purchase from GIBCO. Cell suspension prepared in RPMI 1640-Gluta MAX™ medium supplemented with 10% inactivated bovine fetal serum was plated in 96-well I-type collagen-coated plate so as to contain $3.1 \times 10^4$ cells/100 μL/well. Then, the cells were cultured for 6 hr at 37° C. under 5% $CO_2$/95% air to be adhered to the bottom of the plate. The non-adhered cells were rinsed off with PBS, and the test compound dissolved in DMSO was added to the adhered cells (final concentration: 1, 10, 100 nM), and the mixture was cultured for 1 hr. Then, HMGB-1 was added thereto (final concentration: 10 μg/mL), and the mixture was incubated for additional 24 hr. TNFα production amount contained in the culture supernatant was quantified by ELISA method (R&D systems). TNFα production inhibition rate (%) was calculated using the value under the HMGB-1-free condition as control of 100% inhibition and the value under the compound-free condition as control of 0% inhibition. The results are shown in Table 5.

TABLE 5

| Compound No. | Compound concentration (nM) | TNFα production inhibition rate (% inhibition) |
|---|---|---|
| 6 | 1 | 45 |
|   | 10 | 82 |
|   | 100 | 85 |

Test Example 5: Evaluation of Analgesic Action on Oxaliplatin Induced-Neuropathic Pain Model Mouse Oxaliplatin was diluted with saline by the predetermined concentration, and administered intraperitoneally to mice (C57BL/6N, male, 8 weeks old) at 0.3 mg/kg. The test compound was dissolved in 10% captisol or 10% captisol containing 0.1% N-methyl-2-pyrrolidone. The compound was administered intravenously (0.1-10 mg/kg body weight) to the mice immediately before intraperitoneal administration of various anticancer drugs. The pain threshold was measured 1 week after oxaliplatin administration. The pain threshold was evaluated as a weighted value (gram) showing pseudo-escape reaction, when the footpad of the right hind limb was pressed using balance type pressurizing device (Ugo Basile). The results are shown in Table 6. The values in the table show the mean±standard errors of the weighted values.

TABLE 6

|  |  |  |
|---|---|---|
| Normal |  | 322.0 ± 22.0 |
| Vehicle |  | 83.3 ± 23.0 |
| Compound No. 6 | 1 mg/kg | 190.0 ± 46.1 |
|  | 3 mg/kg | 153.3 ± 46.1 |
|  | 10 mg/kg | 310.0 ± 45.6# |
| Normal |  | 273.3 ± 11.2 |
| Vehicle |  | 116.7 ± 20.3 |
| Compound No. 14 | 0.1 mg/kg | 208.0 ± 33.8 |
|  | 0.3 mg/kg | 215.0 ± 21.6 |
|  | 1 mg/kg | 310.0 ± 33.8# |
| Normal |  | 323.3 ± 32.0 |
| Vehicle |  | 121.7 ± 16.0 |
| Compound No. 21 | 0.1 mg/kg | 160.0 ± 29.7 |
|  | 0.3 mg/kg | 265.0 ± 58.5 |
|  | 1 mg/kg | 285.0 ± 19.3# |

Shirley-Williams;
$p < 0.01$ vs vehicle

Pharmaceutical Preparation Example 1 (Production of Capsule)

| 1) Compound of Example 1 | 30 mg |
|---|---|
| 2) Finely powdered cellulose | 10 mg |
| 3) Lactose | 19 mg |
| 4) Magnesium stearate | 1 mg |
| Total | 60 mg |

1), 2), 3) and 4) are mixed, and packed into a gelatin capsule.

Pharmaceutical Preparation Example 2 (Production of Tablets)

| 1) Compound of Example 1 | 30 g |
|---|---|
| 2) Lactose | 50 g |
| 3) Corn starch | 15 g |
| 4) Carboxymethylcellulose calcium | 44 g |
| 5) Magnesium stearate | 1 g |
| 1000 tablets, total | 140 g |

The total quantities of 1), 2) and 3) and 30 g of 4) are kneaded with water, the kneaded mixture is then subjected to vacuum drying and granulation. To said granular powder is admixed 14 g of 4) and 1 g of 5) and the mixture subjected to tableting using a tableting machine. In this way, 1000 tablets containing 30 mg of compound of Example 1 per tablet are obtained.

INDUSTRIAL APPLICABILITY

The compounds of the present invention have TLR4 signaling inhibitory action and are useful as agents for the prevention and treatment of autoimmune diseases and/or inflammatory diseases, or diseases such as chemotherapy-induced peripheral neuropathy (CIPN), chemotherapy-induced neuropathic pain (CINP), liver injury, ischemia-reperfusion injury (IRI) and the like.

What is claimed is:

1. A compound represented by the following formula (I) or a salt thereof

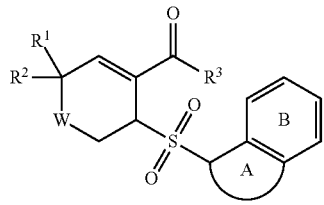

(I)

wherein,

Ring A is cyclopentene or cyclohexene;

Ring B is a benzene ring optionally substituted by 1 to 3 substituent(s) selected from the group consisting of a halogen atom and a $C_{1-6}$ alkyl group;

as to $R^1$ and $R^2$, (1) $R^1$ and $R^2$ are both hydrogen atoms, or (2) one of $R^1$ and $R^2$ is a hydrogen atom, and the other is a hydroxy group, or $R^1$ and $R^2$ may bond together to form a 3- to 8-membered monocyclic non-aromatic heterocycle, which is optionally substituted by 1 to 3 $C_{1-6}$ alkyl group(s) optionally substituted by 1 to 3 substituent(s) selected from the group consisting of a hydroxy group and a $C_{1-6}$ alkoxy group;

W is $CH_2$ or O; and $R^3$ is a $C_{1-6}$ alkoxy group optionally substituted by 1 to 3 $C_{3-10}$ cycloalkyl group(s) optionally substituted by 1 to 3 $C_{1-6}$ alkyl group(s).

2. A compound which is ethyl (2R,3R,8R)-8-(((1S)-7-chloro-2,3-dihydro-1H-inden-1-yl)sulfonyl)-2,3-bis(methoxymethyl)-1,4-dioxaspiro[4.5]dec-6-ene-7-carboxylate.

3. A pharmaceutical composition comprising the compound or salt of claim 1, and pharmacologically acceptable carrier.

4. A method of inhibiting toll-like receptor 4 in a mammal, which comprises administering an effective amount of the compound or salt of claim 1 to the mammal.

* * * * *